US010478566B2

(12) United States Patent
Gunn et al.

(10) Patent No.: US 10,478,566 B2
(45) Date of Patent: Nov. 19, 2019

(54) HUBER SAFETY NEEDLE

(71) Applicant: Medical Components, Inc., Harleysville, PA (US)

(72) Inventors: Matthew Gunn, Wayne, PA (US); Kurt Shimer, East Norriton, PA (US); Timothy M. Schweikert, West Chester, PA (US); Mark S. Fisher, Sellersville, PA (US); Kevin Sanford, Chalfont, PA (US)

(73) Assignee: Medical Components, Inc., Harleysville, PA (US)

( * ) Notice: Subject to any disclaimer, the term of this patent is extended or adjusted under 35 U.S.C. 154(b) by 9 days.

(21) Appl. No.: 14/840,447

(22) Filed: Aug. 31, 2015

(65) Prior Publication Data

US 2016/0058954 A1 Mar. 3, 2016

Related U.S. Application Data

(60) Provisional application No. 62/043,906, filed on Aug. 29, 2014.

(51) Int. Cl.
*A61M 5/32* (2006.01)

(52) U.S. Cl.
CPC ........ *A61M 5/3202* (2013.01); *A61M 5/3243* (2013.01); *A61M 5/3275* (2013.01);
(Continued)

(58) Field of Classification Search
CPC .............. A61M 5/3202; A61M 5/3243; A61M 5/3275; A61M 2005/3268;
(Continued)

(56) References Cited

U.S. PATENT DOCUMENTS 4,627,843 A 12/1986 Raines
4,735,618 A 4/1988 Hagen
(Continued)

FOREIGN PATENT DOCUMENTS

CN 1878584 A 12/2006
CN 101415453 A 4/2009
(Continued)

OTHER PUBLICATIONS

International Search Report and Written Opinion for PCT/US2015/047700 dated Nov. 5, 2015.

*Primary Examiner* — Nathan R Price
*Assistant Examiner* — Courtney B Fredrickson

(57) ABSTRACT

A Huber safety needle assembly including a body, configured to receive a needle. The body further including an upper portion having a first gripping portion coupled thereto, a lower portion having a second gripping portion coupled to thereto, and a hinge mechanism. The needle having a needle tip configured to be received in the body. The hinge mechanism is configured to operably transition the body between a closed configuration and an open configuration. The closed configuration allowing at least a portion of the needle, including the needle tip, to extend below the bottom surface of the lower portion of the body. The open configuration allowing the needle tip to be securely received within the lower portion such that it does not extend below the bottom surface of the lower portion.

13 Claims, 46 Drawing Sheets

(52) U.S. Cl.
CPC .............. *A61M 2005/3247* (2013.01); *A61M 2005/3267* (2013.01)

(58) Field of Classification Search
CPC .. A61M 2005/3267; A61M 2005/3247; A61M 2005/1581
See application file for complete search history.

(56) References Cited

U.S. PATENT DOCUMENTS

| | | |
|---|---|---|
| 4,737,144 A | 4/1988 | Choksi |
| 4,887,998 A | 12/1989 | Martin et al. |
| 4,978,344 A | 12/1990 | Dombrowski et al. |
| 5,037,401 A | 8/1991 | DeCamp |
| 5,059,180 A | 10/1991 | McLees |
| 5,171,303 A | 12/1992 | DeCamp |
| 5,300,046 A | 4/1994 | Scarfone et al. |
| 5,322,517 A | 6/1994 | Sircom et al. |
| 5,328,482 A | 7/1994 | Sircom et al. |
| 5,382,240 A | 1/1995 | Lam |
| 5,429,636 A | 7/1995 | Shikhman et al. |
| 5,507,730 A | 4/1996 | Haber et al. |
| 5,531,704 A | 7/1996 | Knotek |
| 5,611,781 A | 3/1997 | Sircom et al. |
| 5,662,610 A | 9/1997 | Sircom |
| 5,693,022 A | 12/1997 | Haynes |
| 5,697,907 A | 12/1997 | Gaba |
| 5,743,883 A | 4/1998 | Visconti |
| 5,823,997 A * | 10/1998 | Thorne ............... A61M 5/283 604/110 |
| 5,879,337 A | 3/1999 | Kuracina et al. |
| 5,925,020 A | 7/1999 | Nestell |
| 5,951,522 A | 9/1999 | Rosato et al. |
| 5,951,525 A | 9/1999 | Thorne et al. |
| 5,957,892 A * | 9/1999 | Thorne ............... A61M 5/3275 604/162 |
| 5,997,504 A | 12/1999 | Bell |
| 6,001,080 A | 12/1999 | Kuracina et al. |
| 6,015,397 A * | 1/2000 | Elson ............... A61M 5/3275 604/192 |
| 6,117,108 A | 9/2000 | Woehr et al. |
| 6,161,630 A | 12/2000 | Stump et al. |
| 6,254,575 B1 | 7/2001 | Thorne, Jr. et al. |
| 6,261,259 B1 | 7/2001 | Bell |
| 6,280,420 B1 | 8/2001 | Ferguson et al. |
| 6,287,278 B1 | 9/2001 | Woehr et al. |
| 6,443,929 B1 | 9/2002 | Kuracina et al. |
| 6,488,667 B1 | 12/2002 | Murphy |
| 6,537,255 B1 | 3/2003 | Raines |
| 6,592,556 B1 * | 7/2003 | Thorne ............... A61M 5/3275 604/110 |
| 6,595,955 B2 | 7/2003 | Ferguson et al. |
| 6,613,015 B2 | 9/2003 | Sandstrom et al. |
| 6,616,630 B1 | 9/2003 | Woehr et al. |
| 6,623,462 B2 | 9/2003 | Guzzo et al. |
| 6,629,959 B2 | 10/2003 | Kuracina et al. |
| 6,663,604 B1 | 12/2003 | Huet |
| 6,676,633 B2 | 1/2004 | Smith et al. |
| 6,719,721 B1 | 4/2004 | Okazaki et al. |
| 6,719,731 B2 | 4/2004 | Parmigiani |
| 6,752,791 B2 | 6/2004 | Murphy et al. |
| 6,796,962 B2 | 9/2004 | Ferguson et al. |
| 6,796,968 B2 | 9/2004 | Ferguson et al. |
| 6,824,530 B2 | 11/2004 | Wagner et al. |
| 6,860,871 B2 | 3/2005 | Kuracina et al. |
| 6,878,136 B2 | 4/2005 | Fleury et al. |
| 6,884,224 B2 | 4/2005 | Dalton |
| 6,902,546 B2 | 6/2005 | Ferguson |
| 6,918,894 B2 | 7/2005 | Fleury et al. |
| 6,926,693 B2 | 8/2005 | Enns |
| 6,932,803 B2 | 8/2005 | Newby |
| 6,939,331 B2 | 9/2005 | Ohshima |
| 6,949,086 B2 | 9/2005 | Ferguson et al. |
| 6,969,372 B1 | 11/2005 | Halseth |
| 6,984,213 B2 | 1/2006 | Homer et al. |
| 6,997,902 B2 | 2/2006 | Thorne et al. |
| 7,004,927 B2 | 2/2006 | Ferguson et al. |
| 7,008,402 B2 | 3/2006 | Ferguson et al. |
| 7,029,461 B2 | 4/2006 | Ferguson et al. |
| 7,097,637 B2 | 8/2006 | Triplett et al. |
| 7,125,397 B2 | 10/2006 | Woehr et al. |
| 7,125,398 B2 | 10/2006 | Garcia, Jr. |
| 7,144,389 B2 | 12/2006 | Ferguson et al. |
| 7,179,244 B2 | 2/2007 | Smith et al. |
| 7,198,618 B2 | 4/2007 | Ferguson et al. |
| 7,214,211 B2 | 5/2007 | Woehr et al. |
| 7,226,434 B2 | 6/2007 | Carlyon et al. |
| 7,264,613 B2 | 9/2007 | Woehr et al. |
| 7,291,135 B2 | 11/2007 | Ono |
| 7,341,573 B2 | 3/2008 | Ferguson et al. |
| 7,347,842 B2 | 3/2008 | Thorne et al. |
| 7,357,784 B2 | 4/2008 | Ferguson |
| 7,413,562 B2 | 8/2008 | Ferguson et al. |
| 7,422,573 B2 | 9/2008 | Wilkinson et al. |
| 7,438,703 B2 | 10/2008 | Barrus et al. |
| 7,455,664 B2 | 11/2008 | Fleury et al. |
| 7,458,954 B2 | 12/2008 | Ferguson et al. |
| 7,534,231 B2 | 5/2009 | Kuracina et al. |
| 7,549,979 B2 | 6/2009 | Enns et al. |
| 7,569,044 B2 | 8/2009 | Triplett et al. |
| 7,608,057 B2 | 10/2009 | Woehr et al. |
| 7,611,485 B2 | 11/2009 | Ferguson |
| 7,611,487 B2 | 11/2009 | Woehr et al. |
| 7,618,395 B2 | 11/2009 | Ferguson |
| 7,625,360 B2 | 12/2009 | Woehr et al. |
| 7,717,888 B2 | 5/2010 | Vaillancourt et al. |
| 7,758,544 B2 | 7/2010 | Solomon et al. |
| 7,762,992 B2 | 7/2010 | Triplett et al. |
| 7,776,016 B1 | 8/2010 | Halseth |
| 7,858,774 B2 | 12/2010 | Ionescu et al. |
| 7,927,314 B2 | 4/2011 | Kuracina et al. |
| 8,002,746 B2 | 8/2011 | Erskine |
| 8,142,446 B2 | 3/2012 | Shan |
| 8,152,770 B2 | 4/2012 | Reid |
| D686,316 S | 7/2013 | Baid |
| 8,496,626 B2 | 7/2013 | Hiraoka et al. |
| D687,548 S | 8/2013 | Hayashi |
| 8,500,703 B2 | 8/2013 | Lambert |
| 8,574,197 B2 | 11/2013 | Halseth et al. |
| 8,834,422 B2 | 9/2014 | Walker et al. |
| D716,444 S | 10/2014 | Khalaj |
| D731,641 S | 6/2015 | Du |
| 9,248,234 B2 | 2/2016 | Barron |
| 2001/0039401 A1 | 11/2001 | Ferguson et al. |
| 2002/0099338 A1 | 7/2002 | Young |
| 2002/0173749 A1 | 11/2002 | Wagner et al. |
| 2003/0114797 A1 | 6/2003 | Vaillancourt et al. |
| 2003/0163097 A1 | 8/2003 | Fleury et al. |
| 2003/0163098 A1 | 8/2003 | Fleury et al. |
| 2004/0049159 A1 | 3/2004 | Barrus et al. |
| 2004/0082922 A1 | 4/2004 | Fleury et al. |
| 2004/0087912 A1 | 5/2004 | Swenson |
| 2004/0138613 A1 | 7/2004 | Reid |
| 2004/0147881 A1 | 7/2004 | Hyun |
| 2004/0167477 A1 | 8/2004 | Wilkinson et al. |
| 2004/0220528 A1 | 11/2004 | Garcia, Jr. |
| 2005/0080386 A1 | 4/2005 | Reid |
| 2005/0107748 A1 * | 5/2005 | Thorne ............... A61M 5/158 604/263 |
| 2006/0047252 A1 | 3/2006 | Ono |
| 2006/0064061 A1 | 3/2006 | Solomon et al. |
| 2006/0074387 A1 | 4/2006 | Thorne et al. |
| 2006/0129106 A1 | 6/2006 | Ferguson et al. |
| 2007/0010622 A1 | 1/2007 | Naito et al. |
| 2007/0106222 A1 | 5/2007 | Bennett |
| 2007/0282275 A1 | 12/2007 | Ferguson et al. |
| 2008/0097304 A1 | 4/2008 | Thorne |
| 2008/0119795 A1 | 5/2008 | Erskine |
| 2008/0171986 A1 | 7/2008 | Baid |
| 2008/0208139 A1 | 8/2008 | Scheurer et al. |
| 2008/0262434 A1 | 10/2008 | Vaillancourt |
| 2009/0062744 A1 | 3/2009 | Weilbacher et al. |
| 2009/0137958 A1 | 3/2009 | Erskine |
| 2009/0163875 A1 | 6/2009 | Hiraoka et al. |

(56) References Cited

U.S. PATENT DOCUMENTS

| | | |
|---|---|---|
| 2009/0249605 A1 | 10/2009 | Erskine |
| 2009/0299302 A1 | 12/2009 | Lambert |
| 2010/0082002 A1 | 4/2010 | Baid |
| 2010/0137815 A1 | 6/2010 | Kuracina et al. |
| 2010/0280413 A1 | 11/2010 | Ferguson et al. |
| 2011/0166526 A1 | 7/2011 | Kuracina et al. |
| 2011/0220274 A1 | 9/2011 | Erskine |
| 2011/0276013 A1* | 11/2011 | Saitoh .................. A61M 5/158 604/263 |
| 2012/0012332 A1 | 1/2012 | Rooks |
| 2012/0123332 A1 | 5/2012 | Erskine |
| 2014/0296795 A1 | 10/2014 | Adams et al. |
| 2016/0074596 A1 | 3/2016 | Mantsch et al. |

FOREIGN PATENT DOCUMENTS

| | | |
|---|---|---|
| EP | 1116493 A1 | 7/2001 |
| EP | 1186313 A1 | 3/2002 |
| EP | 1 430 921 A2 | 6/2004 |
| EP | 2 016 964 A1 | 1/2009 |
| EP | 2609953 | 7/2013 |
| EP | 2827924 A1 | 1/2015 |
| GB | 1233302 | 5/1971 |
| JP | 2003044975 A | 2/2003 |
| JP | 2003076520 A | 3/2003 |
| JP | 2003195227 A | 7/2003 |
| JP | 2003275310 A | 9/2003 |
| JP | 2003299735 A | 10/2003 |
| JP | 2004-195227 A | 7/2004 |
| JP | 2008013112 A | 1/2008 |
| JP | 2008212645 A | 9/2008 |
| JP | 2009142658 A | 7/2009 |
| JP | 2010207634 A | 9/2010 |
| JP | 2011053640 A | 3/2011 |
| JP | 2011115615 A | 6/2011 |
| JP | 2013138853 A | 7/2013 |
| JP | 2015134156 A | 7/2015 |
| WO | 99/07424 A1 | 2/1999 |
| WO | 02/087672 A1 | 11/2002 |
| WO | 2005049109 | 6/2005 |
| WO | 2005/120624 A1 | 12/2005 |
| WO | 2006/085176 A1 | 8/2006 |
| WO | 2006/096633 A1 | 9/2006 |
| WO | 2006/096634 A1 | 9/2006 |
| WO | 2006/096635 A1 | 9/2006 |
| WO | 2006/096636 A1 | 9/2006 |
| WO | 2010/101573 A1 | 9/2010 |
| WO | 2013/139476 A1 | 9/2013 |

* cited by examiner

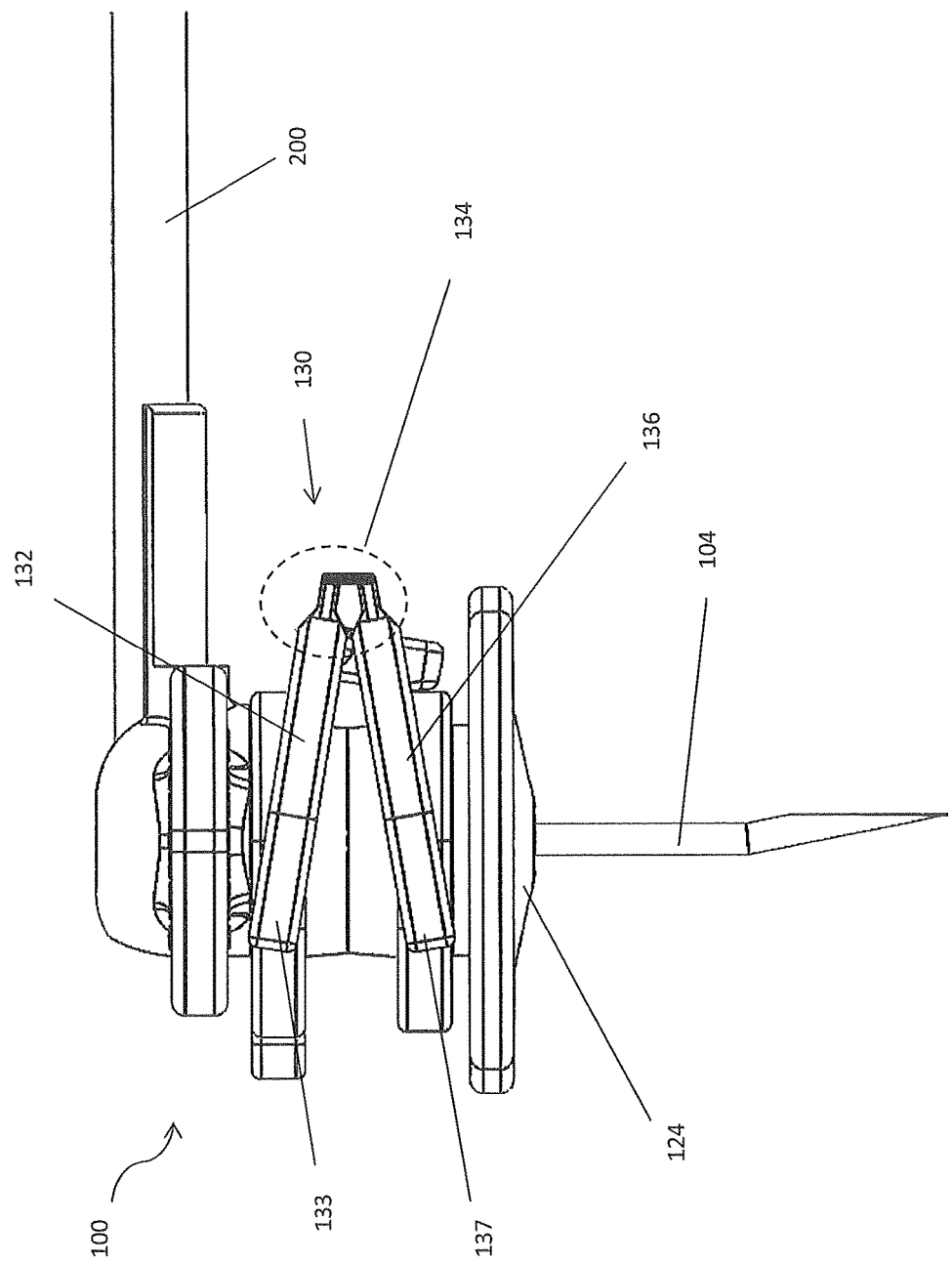

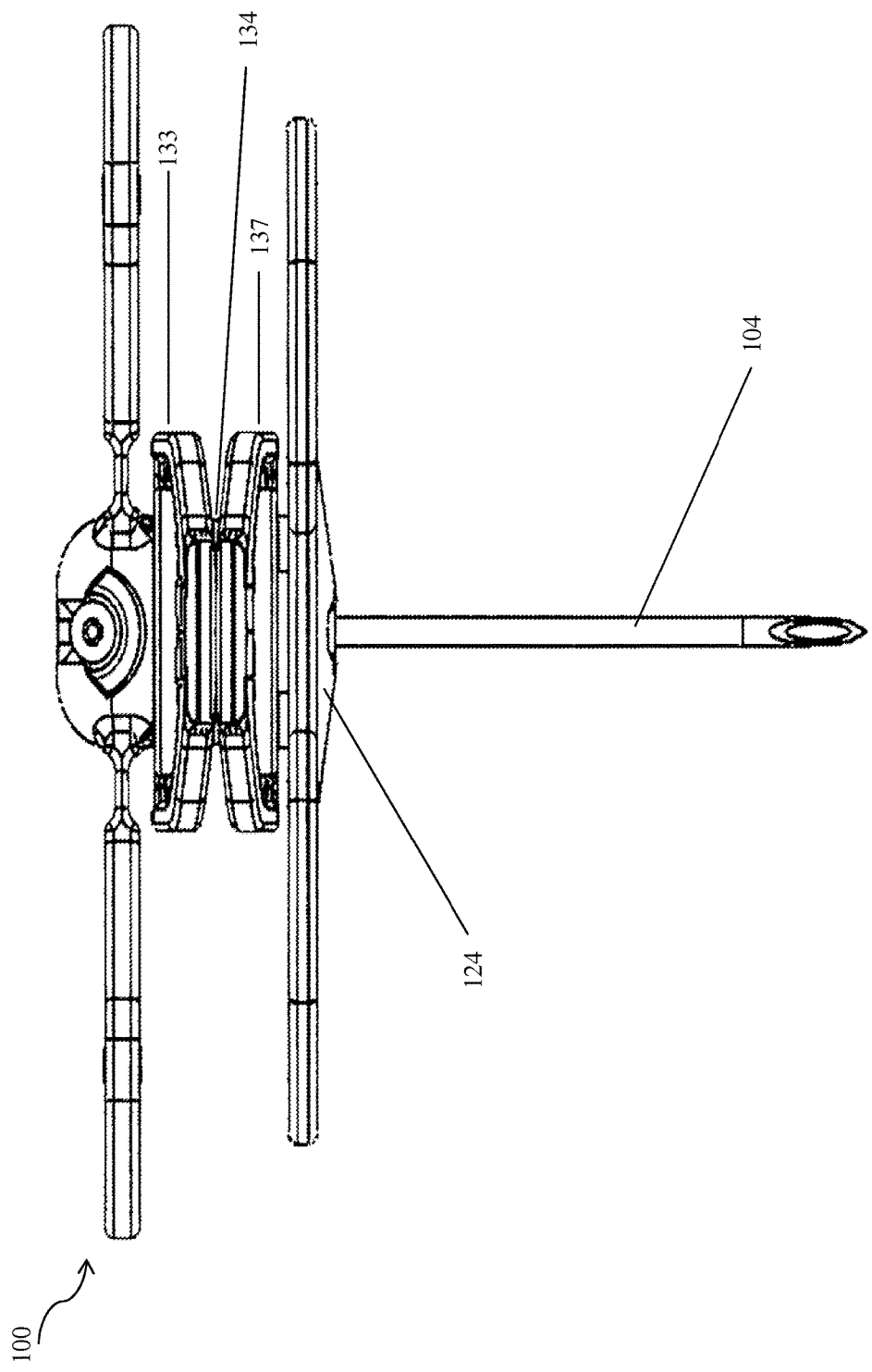

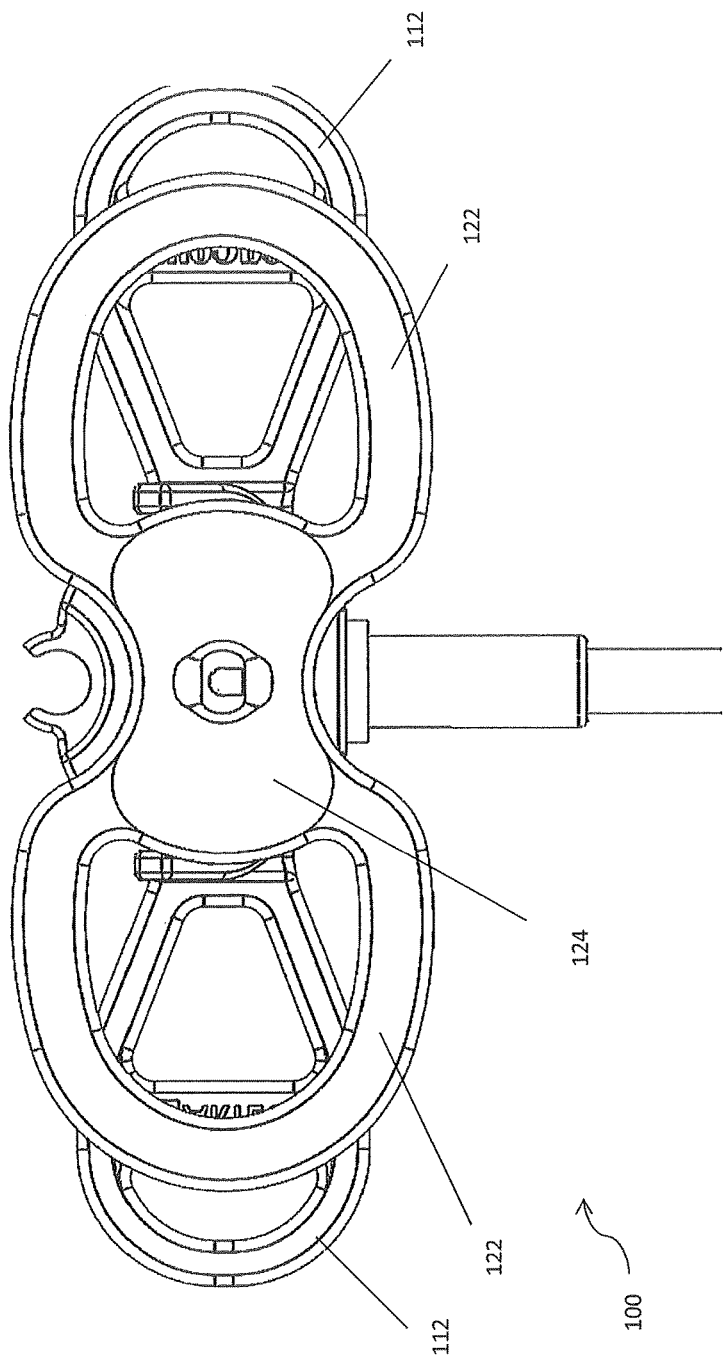

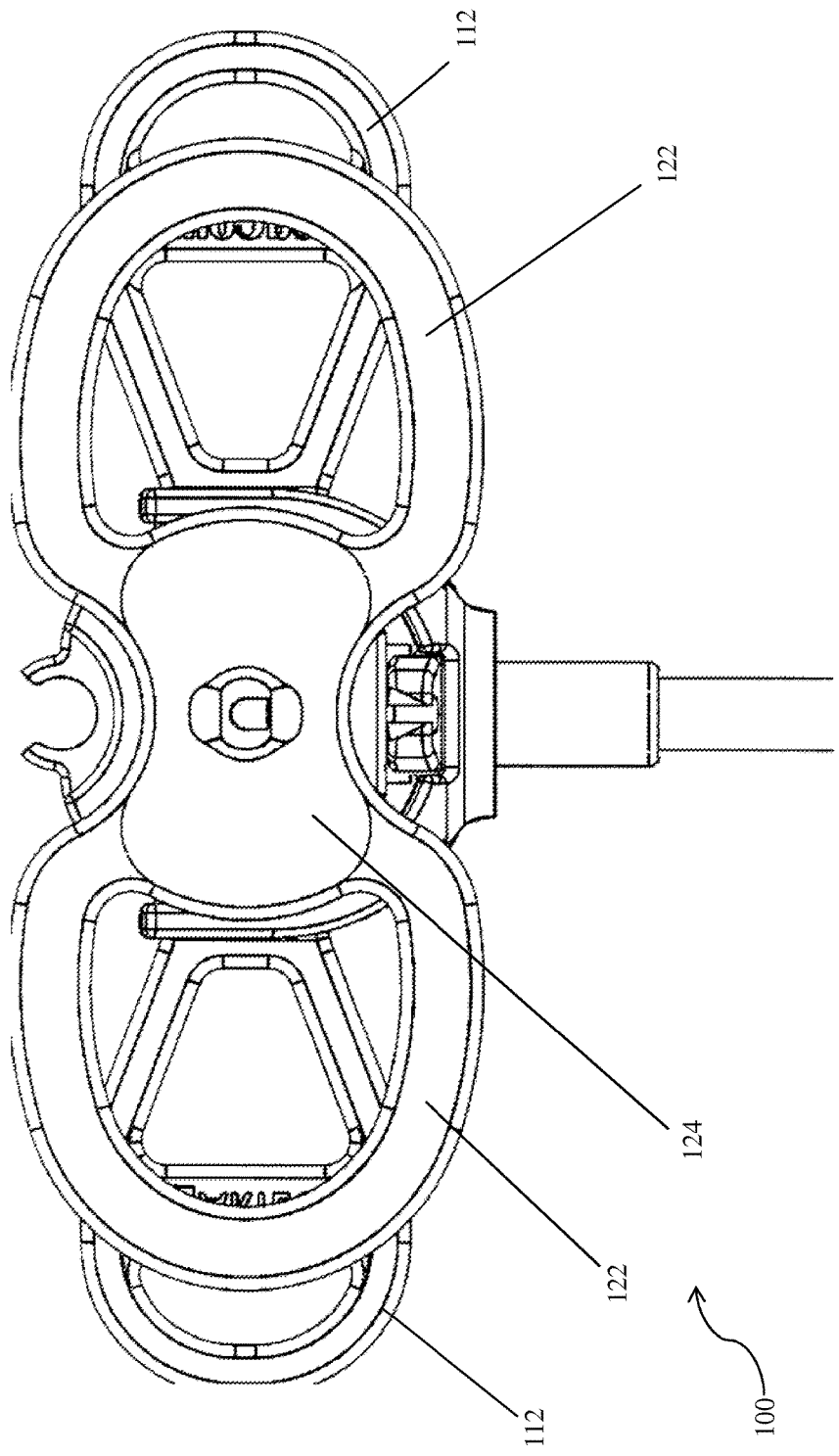

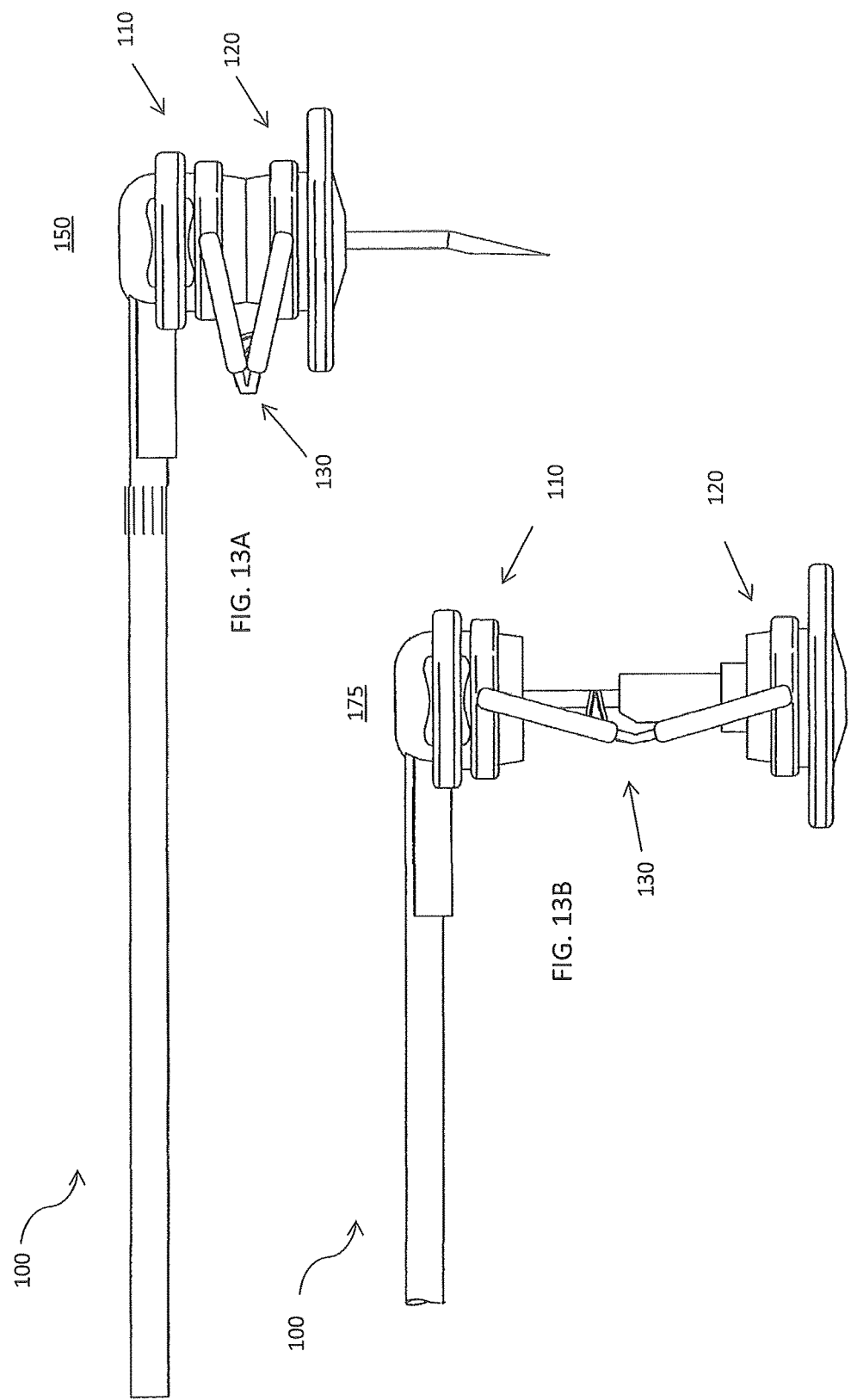

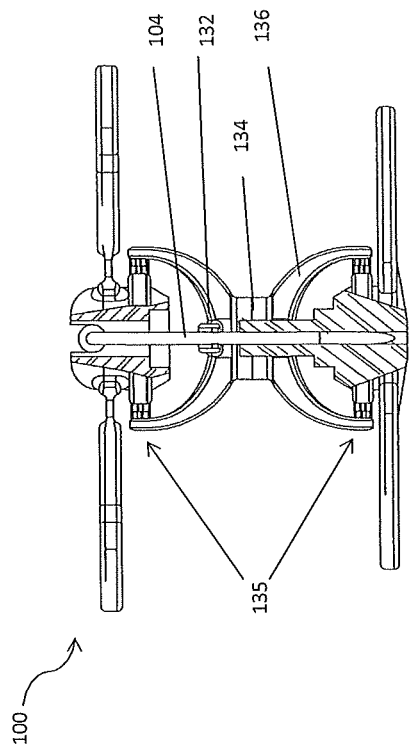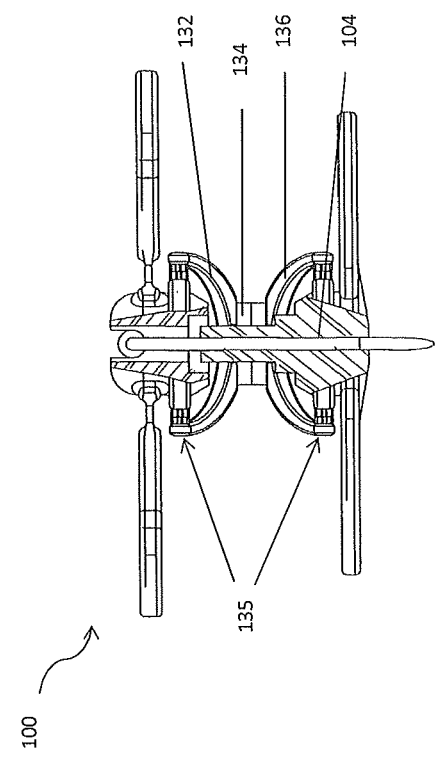

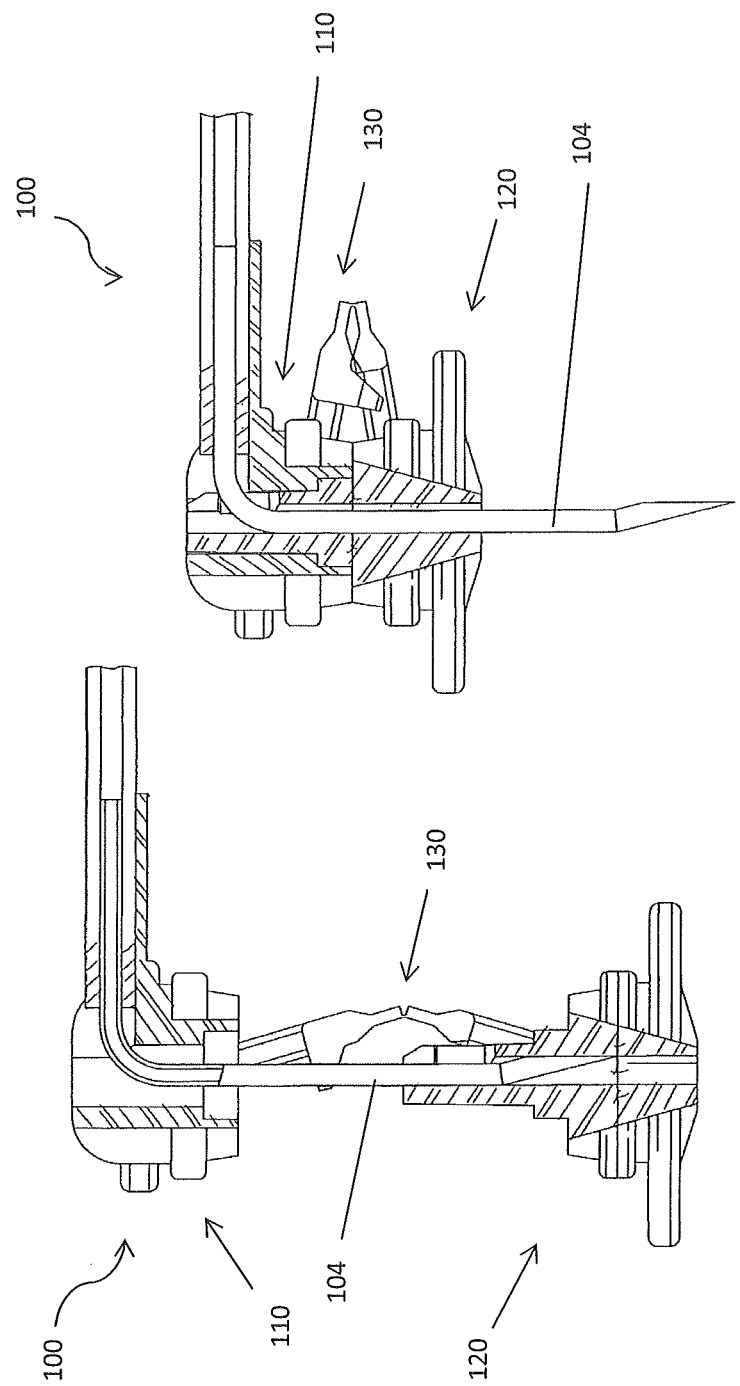

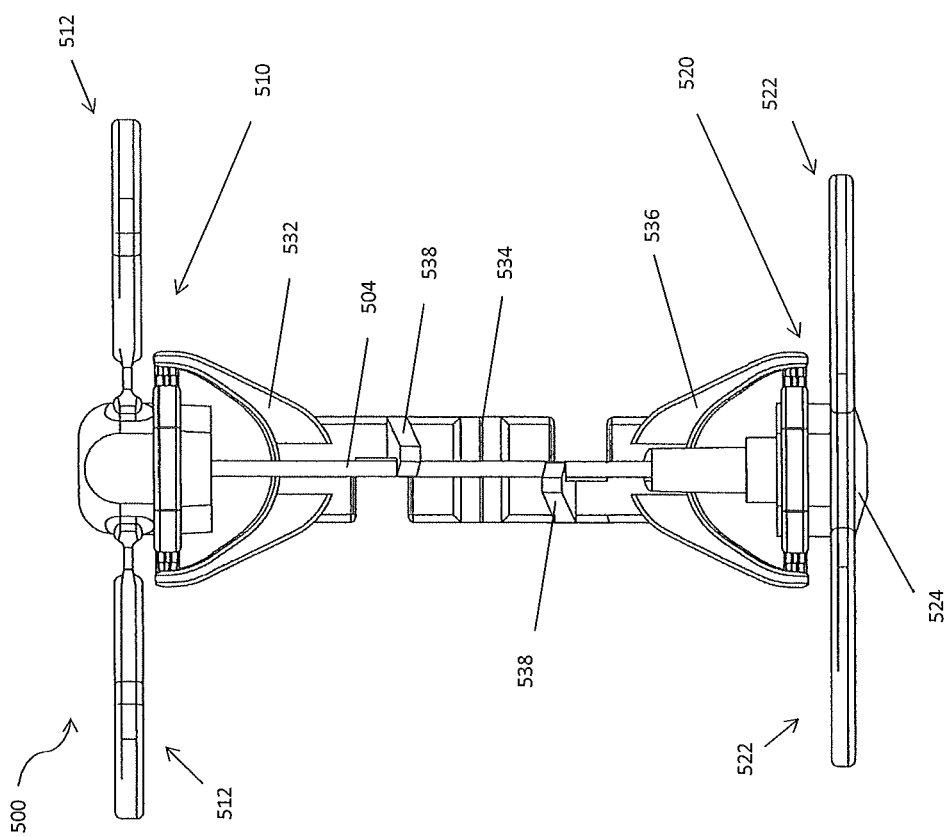

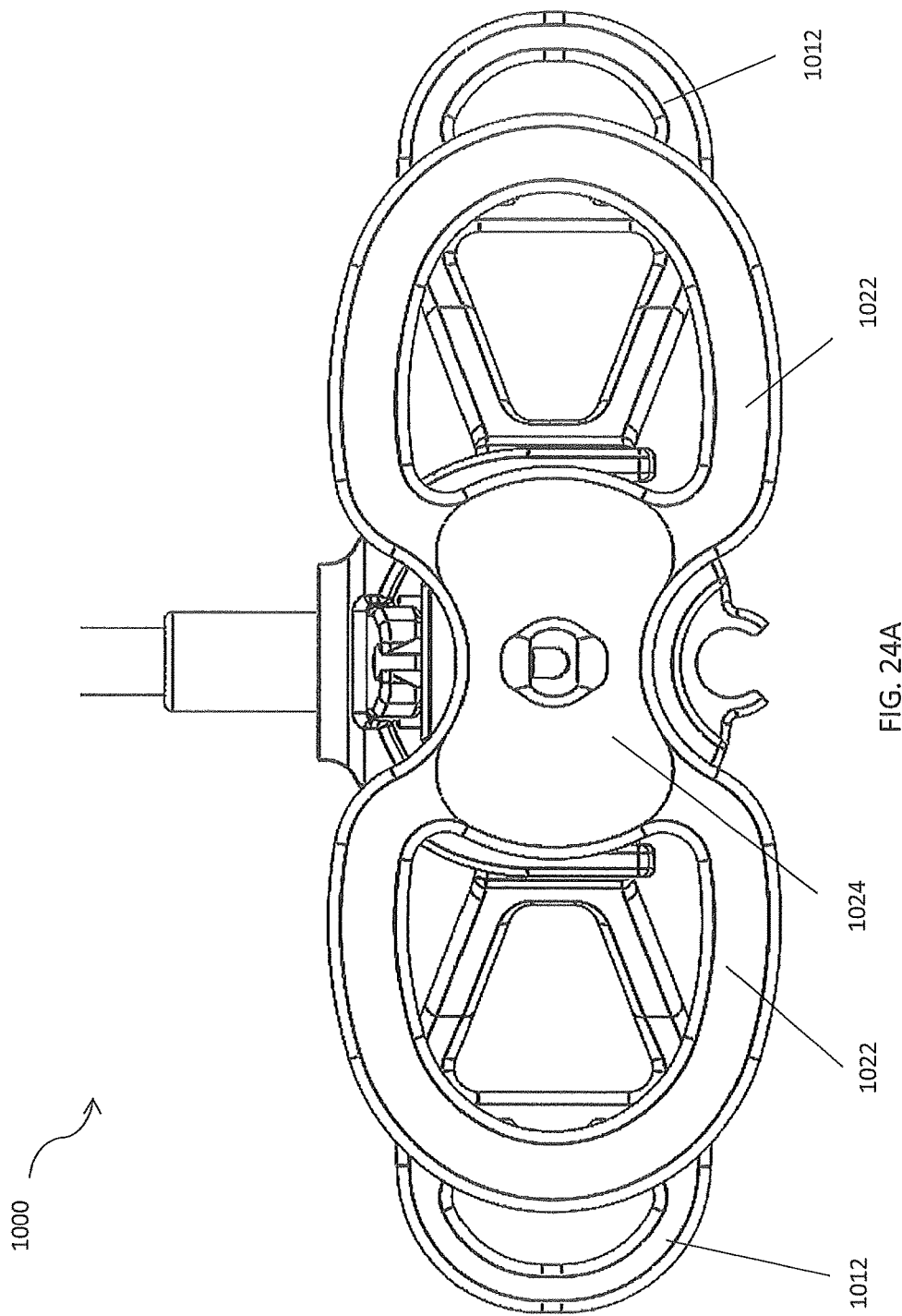

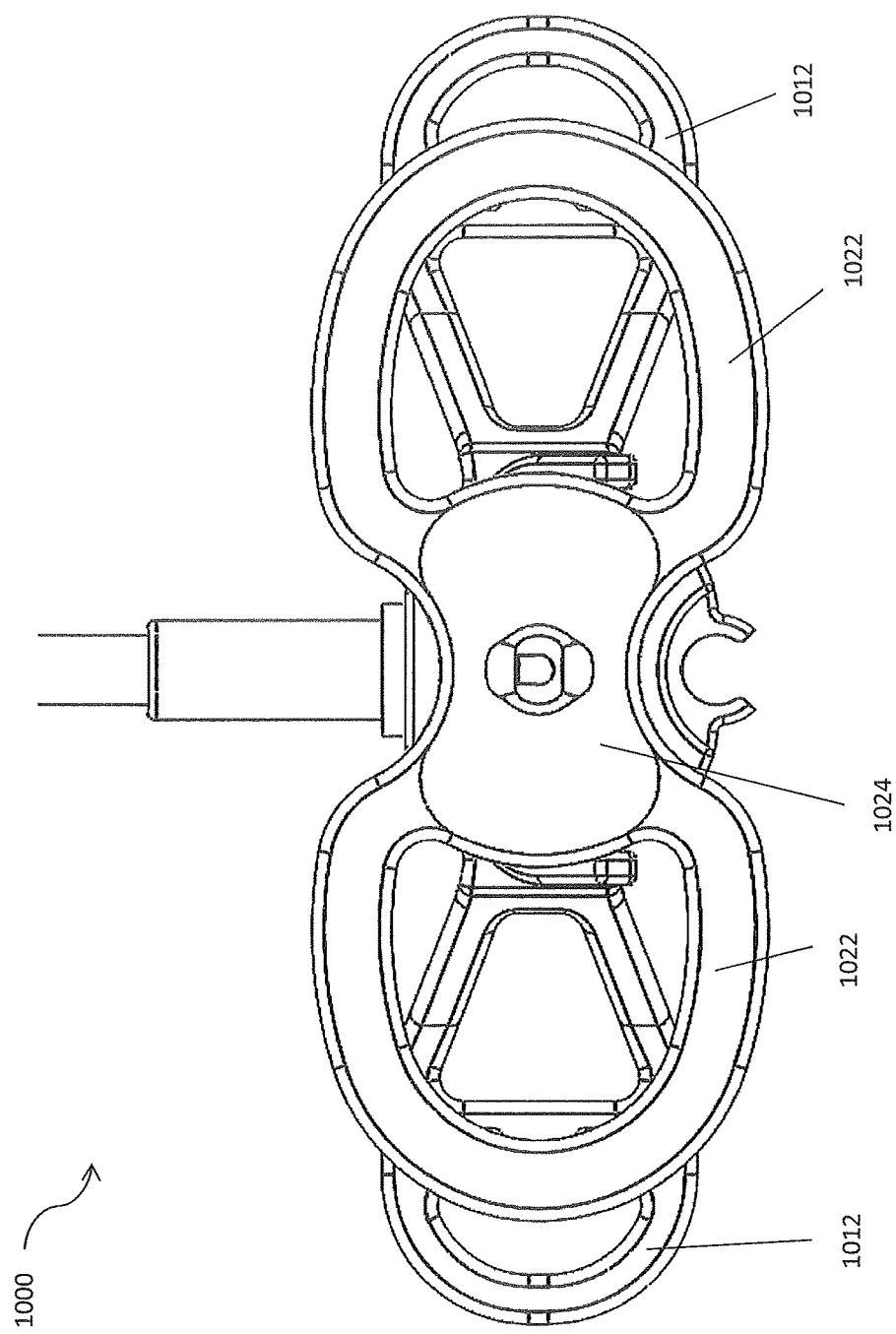

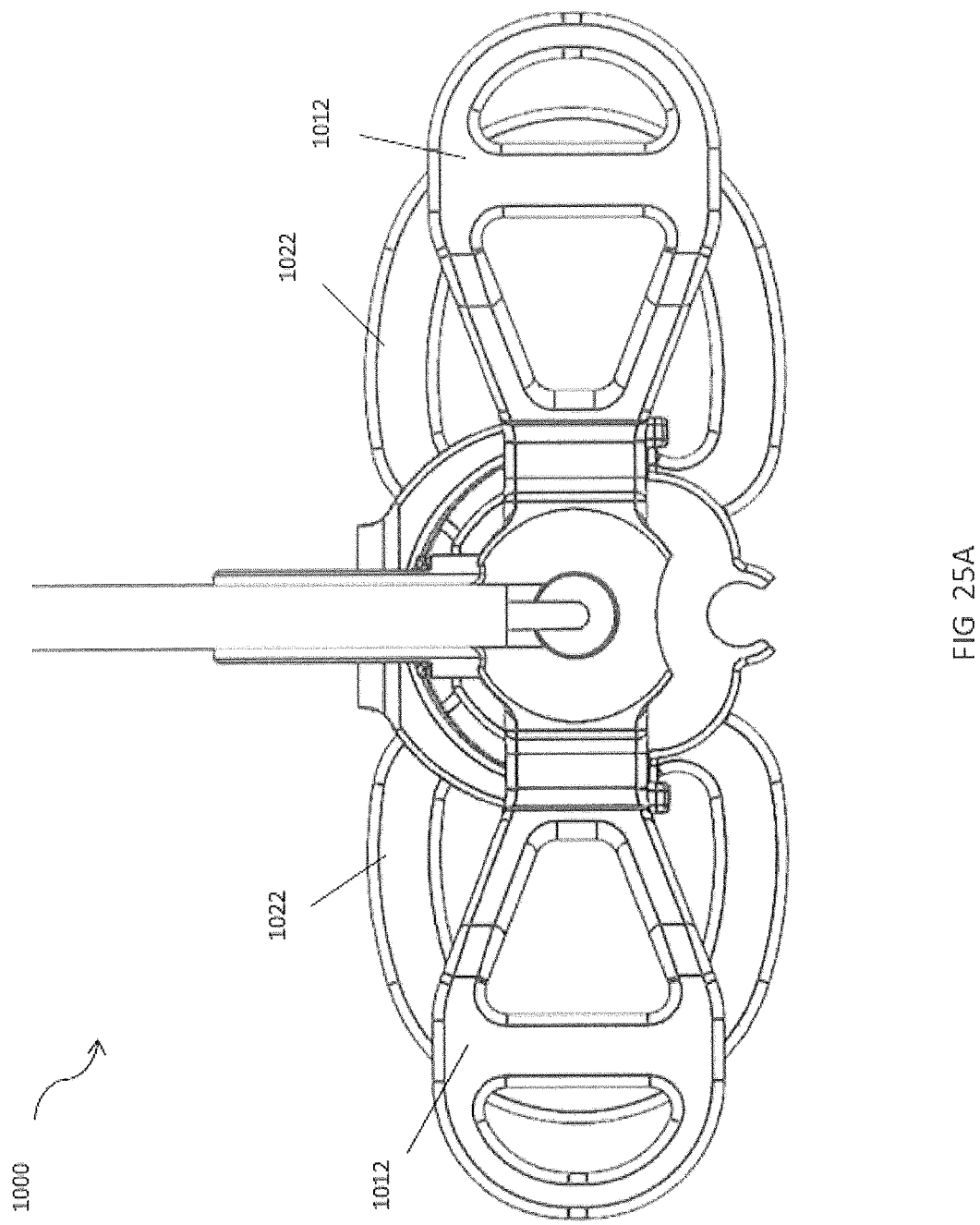

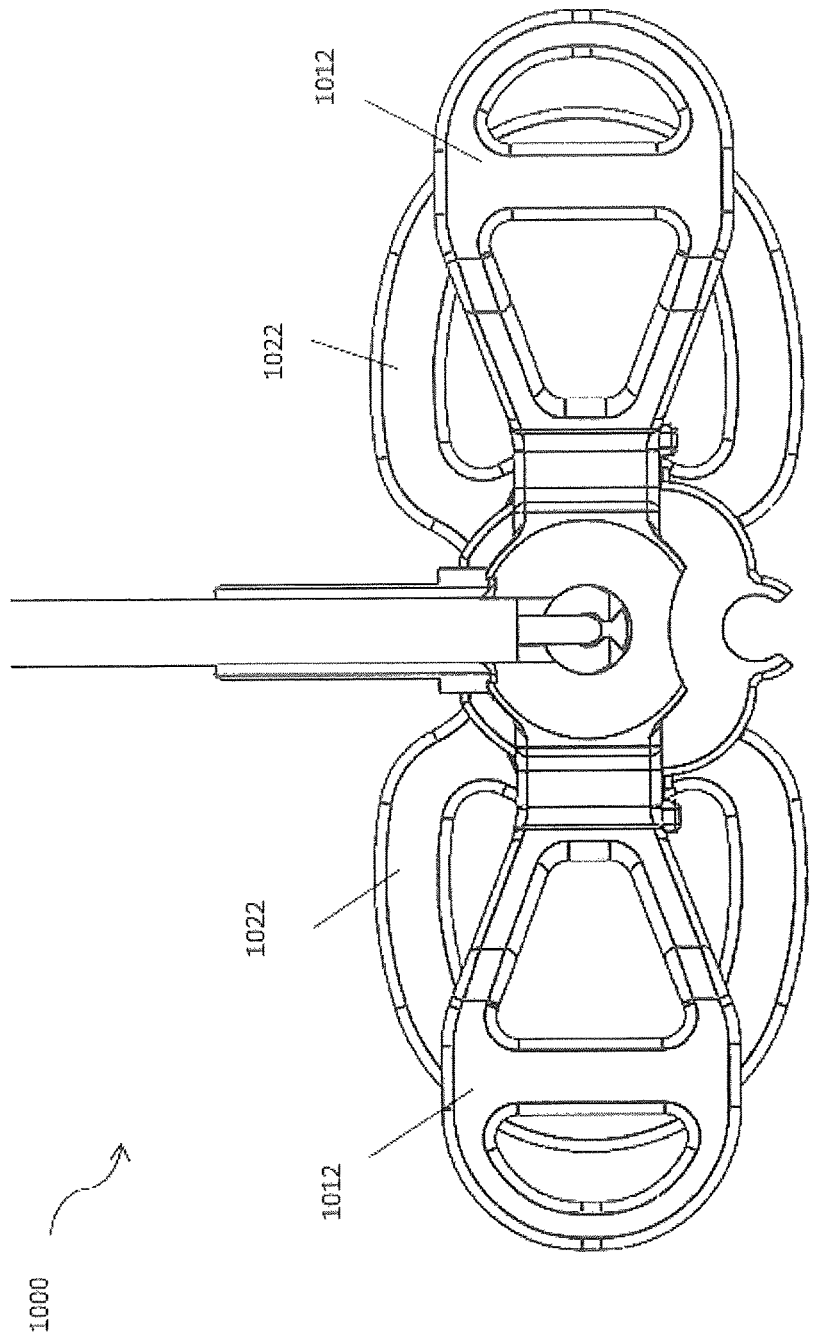

HUBER SAFETY NEEDLE

CROSS-REFERENCE TO RELATED APPLICATIONS

This patent application claims the benefit of U.S. Provisional Patent Application No. 62/043,906, filed on Aug. 29, 2014, which is hereby incorporated by reference in its entirety.

FIELD

The subject matter herein generally relates to Huber needles. More specifically, the subject matter herein relates to Huber safety needles.

BACKGROUND

Known Huber needles are widely used in hospitals and alternate care sites. These needles are often used in conjunction with implanted ports. Such Huber needles provide a non-coring needle that is used to administer chemotherapy, IV fluids, medications, total parenteral nutrition, or to transfuse blood products through implanted ports. The implanted ports contain a self-sealing septum that seals around the needle, holds the needle in place, and allows for multiple accessing by a Huber needle.

The known Huber needle is designed for safety of the patient; however, they present a considerable risk to the user of such Huber needles. The known Huber needle, if improperly used, exposes the user to blood borne pathogens or the drug or medication being administered through the Huber needle. Known Huber needles require two hands to extract the needle from the implanted port. One hand is used to stabilize the implanted port, while the other hand is used to withdraw the needle. The force required to withdraw the needle from the self-sealing septum of the implanted port can cause the needle to rebound and thus a needlestick injury to the user. Such a needle stick injury can result in transfer of a bloodborne pathogen, such as Hepatitis or HIV. Also, healthcare workers that prepare hazardous drugs, mix drugs, or administer drugs are at risk for exposure to the drug. Even when drugs are carefully handled, exposure can result from inhalation or direct skin contact with the drug.

BRIEF SUMMARY

In an exemplary embodiment, a Huber safety needle assembly can include a body having an upper portion, a lower portion, and a hinge mechanism. The assembly can further include a needle having a needle tip and configured to be received in the body. A first gripping portion can be coupled to the upper portion and a second gripping portion coupled to the lower portion. The hinge mechanism can be configured to operably transition the body between a closed configuration and an open configuration, the closed configuration allowing at least a portion of the needle including the needle tip to extend below the bottom surface of the lower portion of the body and the open configuration allowing the needle tip to be securely received within the lower portion such that it does not extend below the bottom surface of the lower portion.

The hinge mechanism can include an upper portion, a middle portion, and a lower portion and have a plurality of pivot points. The upper portion of the hinge mechanism can couple the hinge mechanism to the upper portion of the body and the lower portion of the hinge mechanism can couple the hinge mechanism to the lower portion of the body. The plurality of pivot points can be a first pivot point, a second pivot point, and a third pivot point, the first pivot point being at least one rotatable pin configured for coupling the upper portion of the hinge mechanism to the upper portion of the body, the second pivot point being a thinned area of material configured to allow the material to bend at the middle portion, and the third pivot point being at least one rotatable pin configured for coupling the lower portion of the hinge mechanism to the lower portion of the body.

The hinge mechanism may include at least one attachment point configured to secure the hinge mechanism to the needle in the open configuration. The at least one attachment point may be a snap fit. Furthermore, the at least one attachment point can be a protrusion extending from the hinge mechanism that may be configured to allow passing the needle in one direction thereby securing the needle after transitioning from the closed configuration to the open configuration.

The upper and lower gripping portions may be positioned on each side of the needle assembly keeping a transition force in axial alignment with the needle when transitioning the needle assembly between the closed and open configurations.

The needle assembly may be configured to non-retractably transition from the closed configuration to the open configuration. Furthermore, the body may be configured to matingly receive a catheter. The catheter can be in fluid communication with the body and the needle.

In some embodiments, at least the first pivot point and the second pivot point can be in a same plane as the needle. In other embodiments, the first pivot point and the second pivot point can be offset from a plane of the needle.

The lower portion may have an aperture formed therein configured to allow the needle to extend through the lower portion. In addition, a skin plate may be disposed on the lower portion.

BRIEF DESCRIPTION OF THE DRAWINGS

Implementations of the present technology will now be described, by way of example only, with reference to the attached figures, wherein:

FIGS. 3A-3B are right side views of example embodiments of a Huber safety needle in a closed configuration, showing a short hinge version and a long hinge version, respectively;

FIGS. 4A-4B are rear views of example embodiments of a Huber safety needle in a closed configuration, showing a short hinge version and a long hinge version, respectively;

FIGS. 5A-5B are bottom views of example embodiments of a Huber safety needle in a closed configuration, showing a short hinge version and a long hinge version, respectively;

FIGS. 11A-11B are bottom views of example embodiments of a Huber safety needle in an open configuration, showing a short hinge version and a long hinge version, respectively;

FIGS. 13A-13B are left side views of example embodiments of a Huber safety needle in a closed configuration and an open configuration, respectively;

FIGS. 14A-14B are front cross-sectional views of example embodiments of a Huber safety needle in a closed configuration and an open configuration, respectively;

FIGS. 15A-15B are right side cross-sectional views of example embodiments of a Huber safety needle in a closed configuration and an open configuration, respectively;

FIG. 17 is a front view of an example second embodiment of a Huber safety needle in an open configuration;

FIGS. 24A-24B are bottom views of example third embodiments of a Huber safety needle with the upper gripping portion in a first configuration, showing the assembly in a closed configuration and open configuration, respectively;

FIGS. 25A-25B are top views of example third embodiments of a Huber safety needle with the upper gripping portion in a first configuration, showing the assembly in a closed configuration and open configuration, respectively;

FIGS. 25A-25B are top views of example third embodiments of a Huber safety needle with the upper gripping portion in a first configuration, showing the assembly in a closed configuration and open configuration, respectively; and, FIGS. 26A-26C are isometric views of example third embodiments of a Huber safety needle with the upper gripping portion in a second configuration, showing the assembly in a closed configuration in FIGS. 26A-26B and in an open configuration in FIG. 26C.

DETAILED DESCRIPTION

Figure 1A:
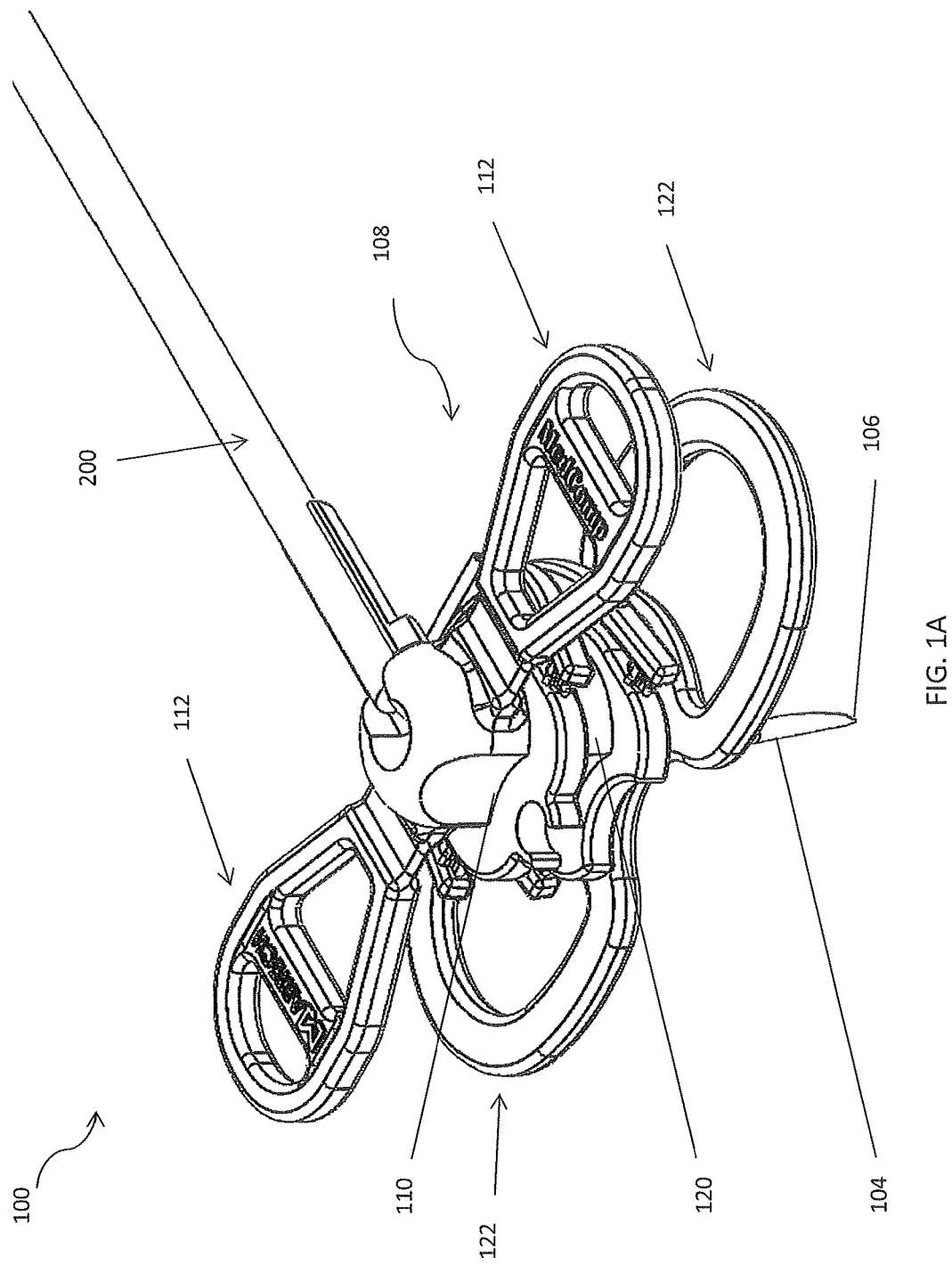
FIGS. 1A-1B are isometric views of example embodiments of a Huber safety needle in a closed configuration, showing a short hinge version and a long hinge version, respectively.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like.

The present disclosure is described in relation to a Huber safety needle assembly 100. The Huber safety needle assembly 100 can include an upper portion 110 and a lower portion 120. The upper portion 110 can secure a needle 104 having a long, beveled tip 106. The lower portion 120 can include a protective sheath and a skin plate 124. In at least one embodiment, the sheath can be referred to as a lower hub. The Huber safety needle assembly 100 can further include a hinge mechanism 130 configured to operably couple the upper portion 110 and the lower portion 120, the hinge mechanism 130 further configured to transition the assembly between an open configuration 175 and a closed configuration 150.

In the closed configuration 150, the Huber safety needle assembly 100 can be configured to expose the needle 104 and the needle tip 106 from the protective sheath, thus allowing delivery of medical treatment. The upper portion 110 and the lower portion 120 can be touching or substantially close to touching, such that the needle 104 extends below the bottom surface of the lower portion 110.

In the open configuration 175, the Huber safety needle assembly 100 is configured to non-retractably extend over the needle tip 106, such that the needle tip is substantially within the sheath or lower hub, thus preventing accidental needlestick and transfer of biological material between an administering technician and a patient. In at least one embodiment, the lower portion 120 is configured to non-retractably extend over the needle tip 106. The upper portion 110 and the lower portion 120 can be displaced from each other relative to a longitudinal axis extending the through the needle 104. The displacement of the lower portion 110 away from the upper portion 120 non-retractably extends the lower portion 120 over the needle tip 106.

The Huber needle assembly can include a body 108 configured to provide mechanical support and protection the needle 104. The body 108 can have any desired shape that provides a hollow portion configured to receive the needle 104. In at least one embodiment, the body 108 of the Huber needle assembly 100 can include the upper portion 110 and the lower portion 102. In at least one embodiment, the body 108 can be made of a thermoplastic material. The body 108 can be formed in a single plastic sheet, removed from the sheet and assembled with the needle 104 being installed. When formed in a single plastic sheet, the body 108 can be substantially flat before being assembled with the needle 104. Alternatively, the upper portion 110, lower portion 120, and hinge mechanism 130 can be formed in one or more plastic sheets and then assembled together. In some embodiments, the upper and lower portions 110, 120 can be formed by injection molding as single pieces with the needle 104 inside the hollow portion of the body 108. Alternatively, the upper and lower portions 110, 120 can be formed from separate pieces and assembled together by adhesive or welding. The assembly 100 with the needle 104 inside can be assembled in the closed configuration 175 for sterilization and shipping purposes.

The upper portion 110 can have an upper gripping portion 112 and the lower portion 120 can have a lower gripping portion 122, each configured for use by the technician when transitioning the device from the closed configuration 150 to the open configuration 175. The upper gripping portion 112 can include a portion on substantially opposing sides of the upper portion 110. The lower gripping portion 122 can include a portion on substantially opposing sides of the lower portion 120. In at least one embodiment, each side of each gripping portion 112, 122 is substantially loop shaped, such as circular, tear drop, or oval and having an aperture formed therein.

The hinge mechanism 130 can be configured to transition the needle 104 between the closed configuration 150 and the open configuration 175. In at least one embodiment, the hinge mechanism 130 can have three pivot points 133, 134, 137. A middle pivot point 134 can be a thinned area allowing the material to bend (or flex) and allow the upper portion 110 of the Huber needle assembly to non-retractably extend away from the bottom portion 120 of the Huber needle assembly. The upper and lower pivot points 133, 137 can be rotatable pin arrangements 135 configured to transition the needle assembly between configurations 150, 175. The rotatable pin can be configured to have at least one pivot point in substantially the same plane as the needle 104. The rotatable pin arrangement 135 can allow the pin to twist as the hinge mechanism 130 is transitioned from the closed configuration 150 to the open configuration 175. The rotatable pin arrangement 135 can shorten the overall length of the hinge mechanism 130 compared to traditional mechanisms, thus creating a lower profile. The hinge mechanism 130 can further include an attachment point 138 configured to secure the hinge mechanism 130 to the needle 104 when in an open configuration 175.

Alternatively, the rotatable pin arrangement 135 can have at least two pivot points 133, 137, each offset from the plane of the needle 104. Both pivot points 133, 137 can be on a same side of the plane of the needle 104. For example, both pivot points 133, 137 can be offset from the plane of the needle 104 by being positioned more towards a front of the assembly 100 relative to the plane of the needle by a distance within the range from $\frac{1}{32}$ of an inch to $\frac{1}{4}$ of an inch. Alternatively, one pivot point can be on one side of the plane of the needle 104, while the other pivot point can be on an opposite side of the plane of the needle 104. In some embodiments, the rotatable pin arrangement 135 can have at least two pivot points 133, 137, where one pivot point is in the same plane as the needle 104 and one is offset from the plane of the needle 104.

In at least one embodiment, the upper pivot point 133 can be a distance $C_U$ from the plane of the needle 104, and the lower pivot can be a distance $C_L$ from the plane of the needle 104. In at least one embodiment, $C_U$ is less than $C_L$ such that the upper portion 132 of the hinge mechanism 130 is shorter than the lower portion 136 of the hinge mechanism 130. For instance, $C_U$ can be $\frac{1}{32}$ of an inch more towards the front of the assembly 100 with respect to the plane of the needle 104, whereas $C_L$ can be $\frac{1}{16}$ of an inch more towards the front of the assembly 100 with respect to the plane of the needle 104. In other embodiments, $C_U$ is greater than $C_L$ such that the upper portion 132 of the hinge mechanism 130 is longer than the lower portion 136 of the hinge mechanism 130. For instance, $C_L$ can be $\frac{1}{32}$ of an inch more towards the front of the assembly 100 with respect to the plane of the needle 104, whereas $C_U$ can be $\frac{1}{16}$ of an inch more towards the front of the assembly 100 with respect to the plane of the needle 104. The rotatable pin arrangement 135 can increase leverage while minimizing the distance necessary for the locking mechanism to engage the needle 104, thus making the Huber safety needle assembly 100 capable of locking passively. Passive locking allows the Huber safety needle assembly 100 to automatically engage the needle 104 as the Huber safety needle assembly 100 transitions from the closed configuration 150 to the open configuration 175. The passive locking allows securing the needle 104 to be a single step process during transition from the closed configuration 150 to the open configuration 175. In at least one embodiment, the rotatable pin arrangement 135 can include a plurality of rotatable pins. The rotatable pin arrangement 135 can allow the pin to twist as the hinge mechanism 130 is transitions the assembly 100 from one configuration 150, 175 to the other. The rotatable pins can be formed at the same time with the other parts of the body 108 using the same material. Each pin can be a simple cylindrical cross section or any cross section that would allow and facilitate the rotation around its axial, e.g., X shaped or with a polarity of ribs.

The transition from a closed configuration 150 to an open configuration 175 can require a user, or technician, to apply a force non-retractably extending the sheath over the needle 104. The gripping portions 112, 122 being located on opposing sides of the needle assembly 100 and configured to facilitate the application of the force required to transition between configurations 150, 175 to be in axial alignment with the needle 104. For example, a user may transition the assembly 100 from a closed configuration 150 to an open configuration 175, causing the at least one attachment point 138 to engage the needle 104, thus preventing any further displacement of the upper portion 110 with respect to the lower portion 120. While in the open configuration 120, the needle tip 106 is sheathed in the lower portion 120, and being non-retractably locked in place by the engagement of the attachment point 138 can prevent rebounding of the needle 104 and thus prevent needlestick injuries.

Figure 1B:
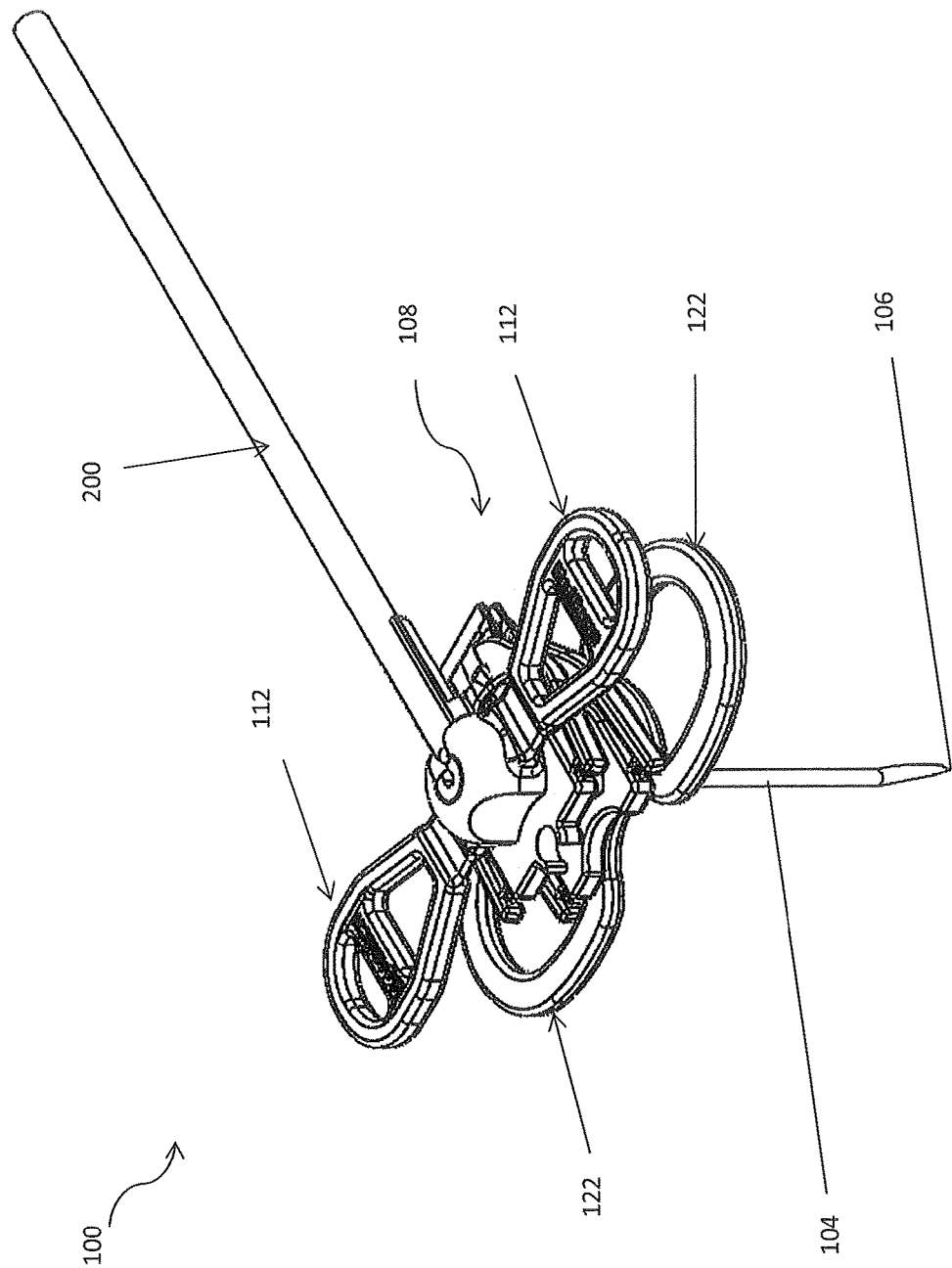

FIGS. 1A-1B illustrate isometric views of examples of a Huber safety needle assembly 100 in a closed configuration 150 in accordance with a first embodiment. The Huber safety needle assembly 100 can include a body 108 configured to secure a needle 104. The needle 104 can have a substantially hollow core configured to allow fluid flow therethrough and have a cross-sectional shape that is substantially circular, oval, triangular, rectangular, polygonal, or combinations thereof. In at least one embodiment, different gauge needles can be used for different applications and different delivery fluids. The needle 104 can be made of any suitable material, such as stainless steel. The body 108 can have an upper portion 110 and a lower portion 120. The body 108 can have any desired shape that provides a hollow portion configured to receive the needle 104. The upper portion 110 can be configured to detachably couple the needle assembly 100 to a catheter 200. For example, the body 108 can be configured to matingly receive the catheter 200. In at least one embodiment, the catheter 200 is in fluid communication with the body 108 and the needle 104 providing a pathway for drugs, solutions, compounds, blood, or some other substance to be delivered through the needle 104. The upper portion 110 can further be configured to secure the needle 104 within the body 108. The lower portion 120 can be configured to receive at least a portion of the needle 104. In at least one embodiment, the lower portion 120 can have an aperture formed therein configured to allow the needle 104 to extend through the lower portion 120. The aperture can be configured to accommodate various needle 104 sizes and gauges, as well as any beveled tip of the needle 104. The lower portion 120 can further include a skin plate 124 on the bottom surface of the lower portion 120. The upper portion 110 and the lower portion 120 can each include upper and lower gripping portions 112, 122, respectively. The upper gripping portion 112 and lower gripping portion 122 can each have opposing sides, each opposing side forming a substantially loop shape. The upper gripping portion 112 and the lower gripping portion 122 can assist a user, or technician, with insertion of the Huber safety needle assembly 100.

Figure 2A:
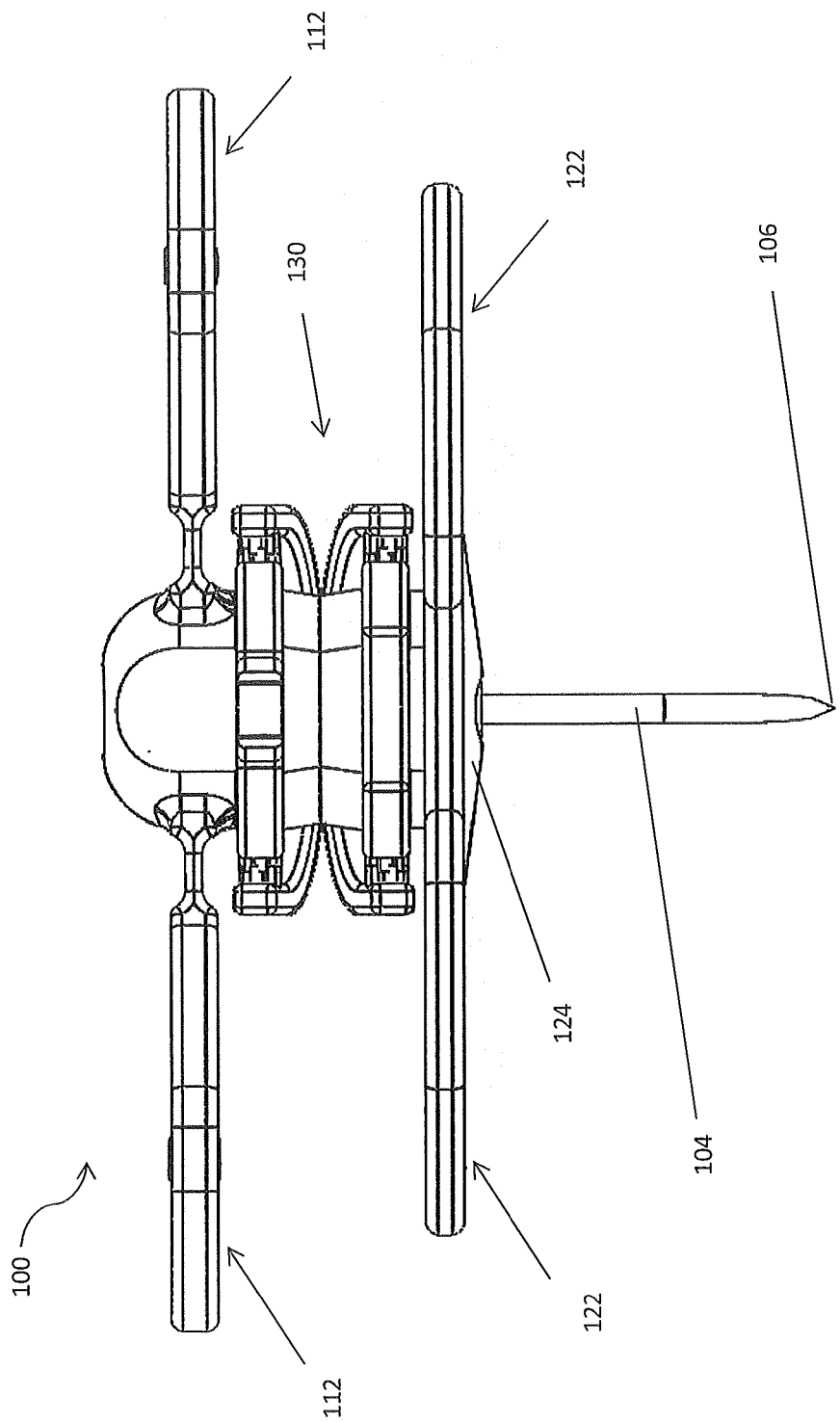
FIGS. 2A-2B are front views of example embodiments of a Huber safety needle in a closed configuration, showing a short hinge version and a long hinge version, respectively.
Figure 2B:
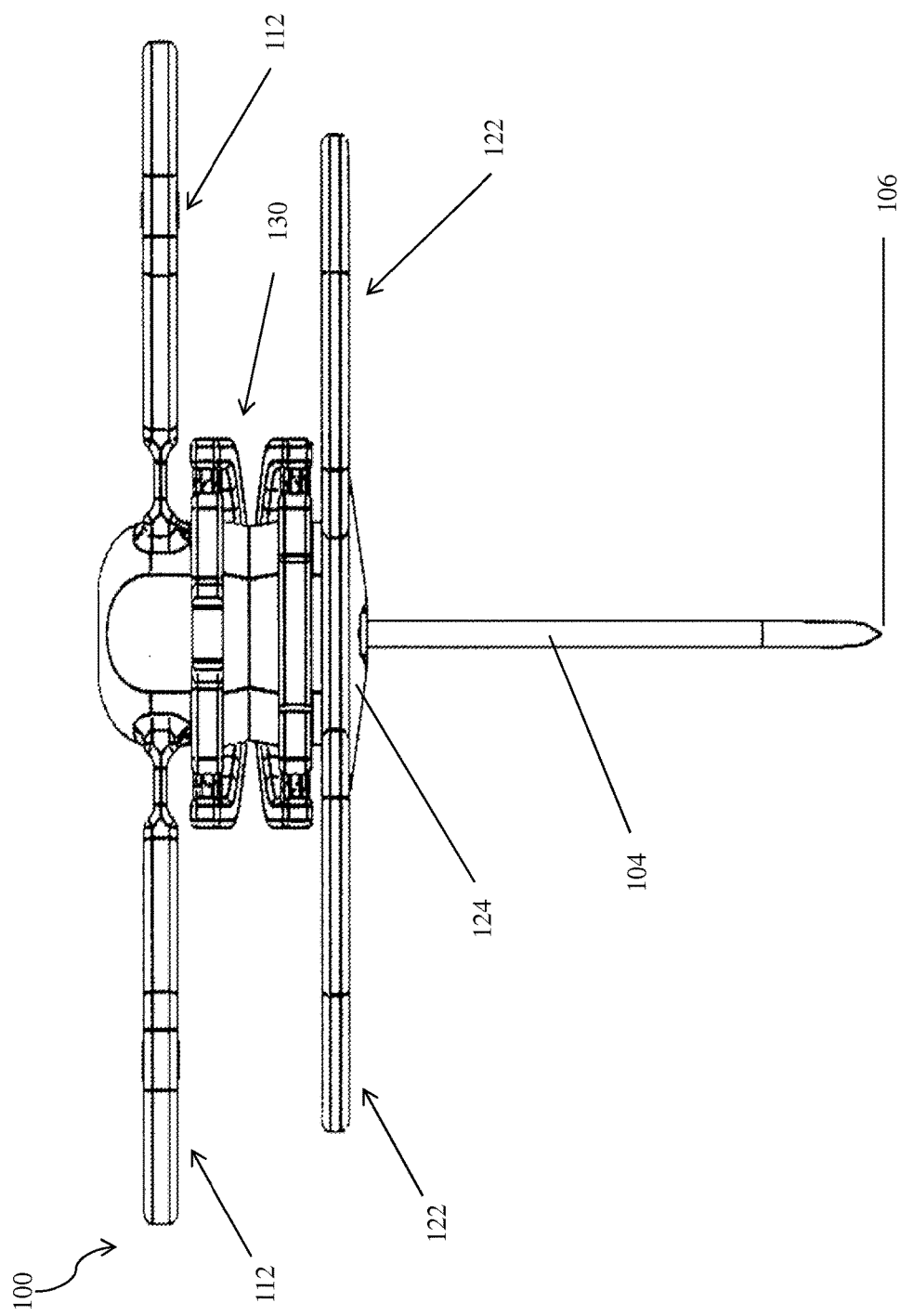

FIGS. 2A-2B illustrate front views of examples of a Huber safety needle assembly 100 in the closed configuration 150 in accordance with a first embodiment. The body 108 can further include a hinge mechanism 130. The hinge mechanism 130 can operably couple the upper portion 110 and the lower portion 120. The hinge mechanism 130 can allow the body 108 to transition from a closed configuration 150 to an open configuration 175 (see FIGS. 13A and 13B). The closed configuration 150 can allow at least a portion of the needle 104, specifically the needle tip 106, to be exposed from the lower portion 120, thus allowing insertion of the needle 104. In at least one embodiment, the needle 104 and needle tip 106 can extend beyond the bottom surface of the lower portion 120. In alternative embodiments, only the needle tip 106 can extend beyond the bottom surface of the lower portion 120.

As can be appreciated in FIGS. 2A and 2B, in the closed configuration 150, the upper portion 110 and the lower portion 120 can be touching or substantially close to touching. Additionally, the upper gripping portion 112 and the lower gripping portion 122 can be substantially parallel to one another and in a plane perpendicular to the needle 104. In alternative embodiments, the upper gripping portion 112 and the lower gripping portion 122 can be substantially perpendicular to one another with the lower portion 120 and lower gripping portion 122 configured to position the skin plate 124 against a patient and the upper gripping portion 112 being substantially perpendicular thereto. Alternatively, the upper gripping portion 112 can be positioned at any angle between parallel and perpendicular relative to the lower gripping portion 122.

Figure 3B:
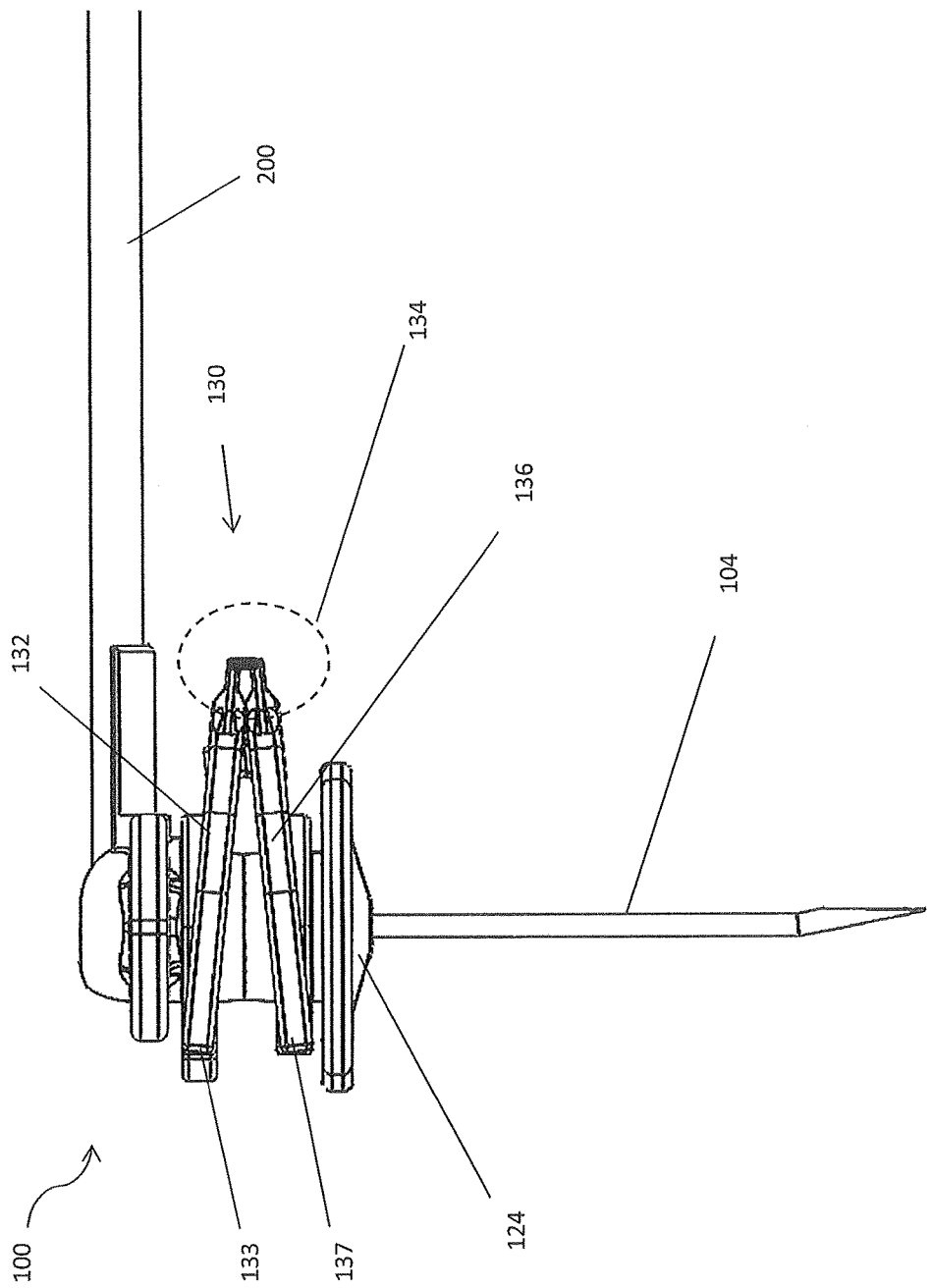
Figure 4A:
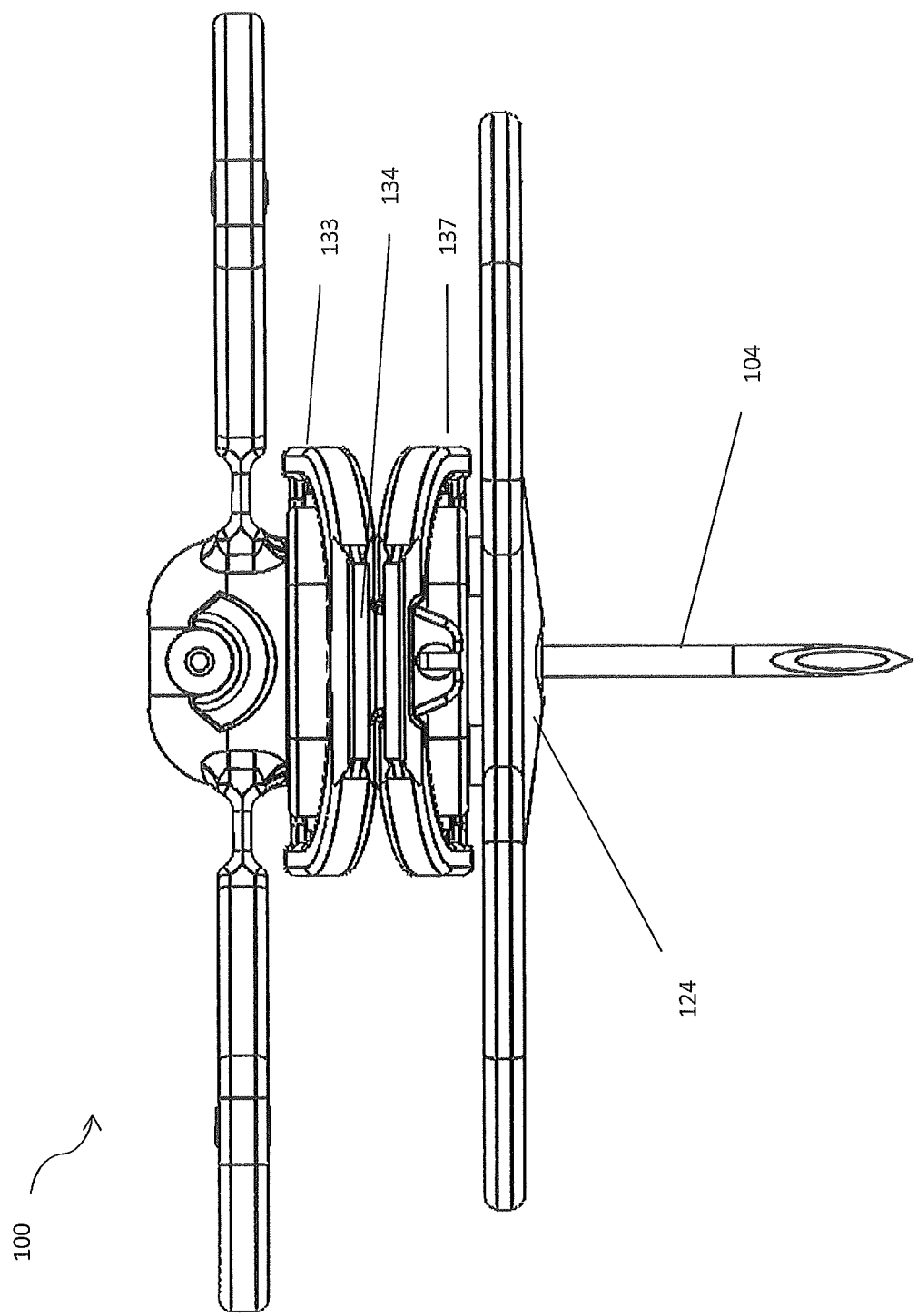
Figure 5B:
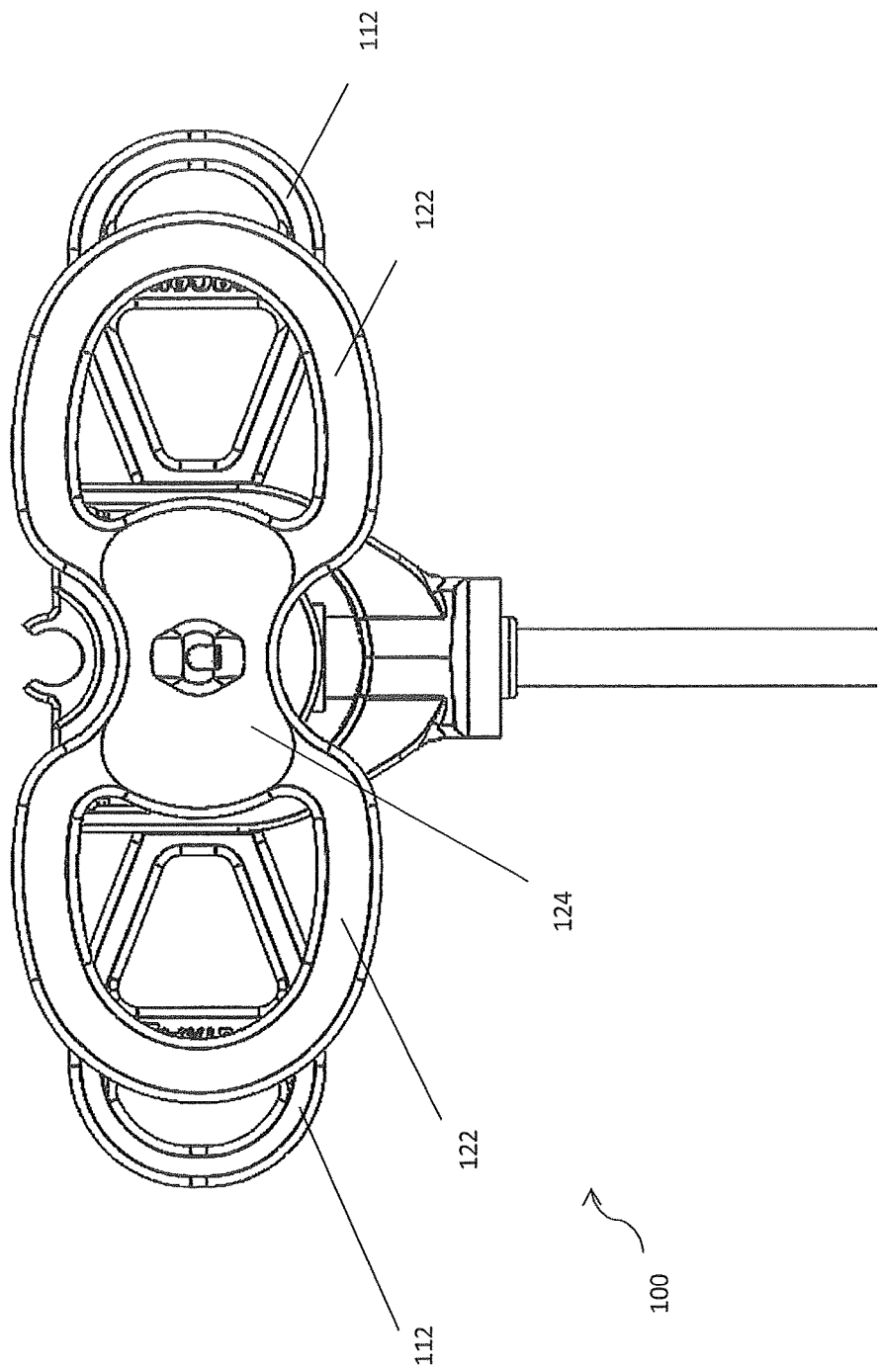
Figure 6A:
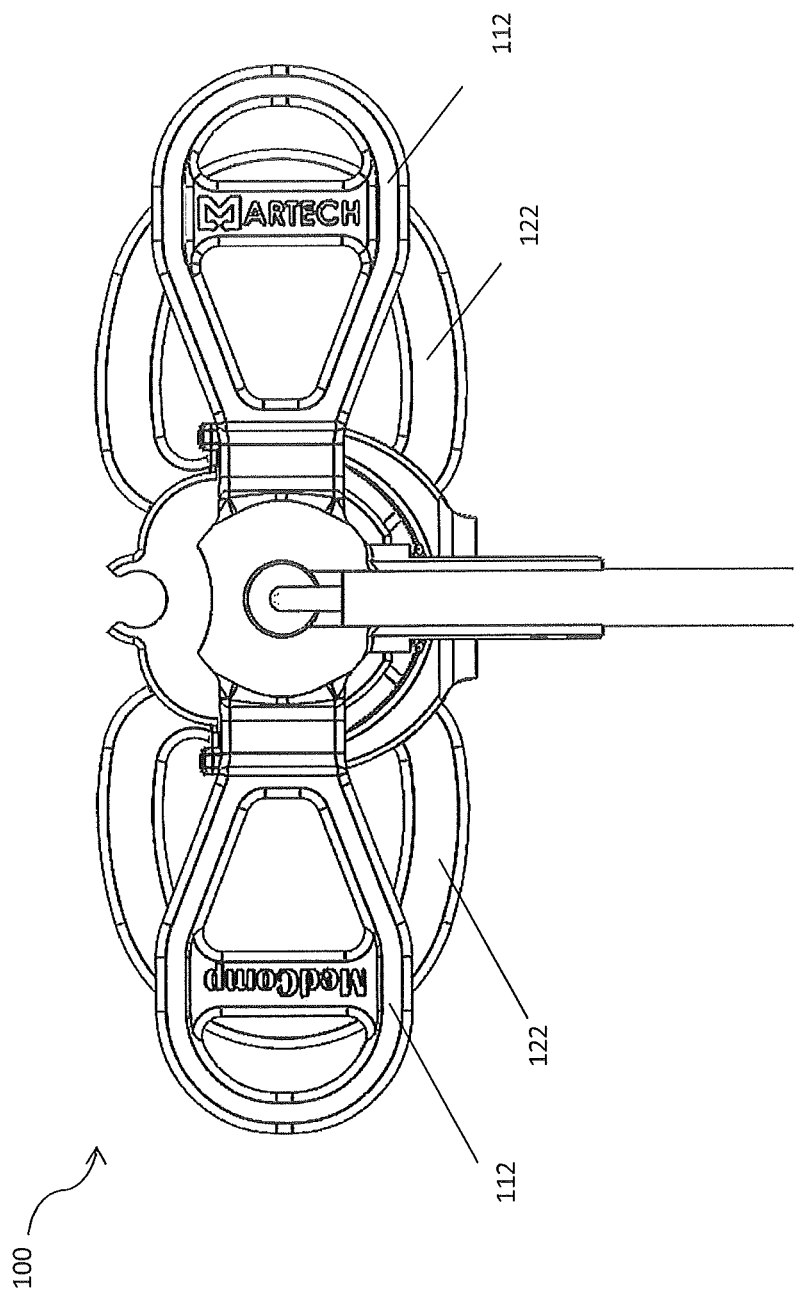
FIGS. 6A-6B are top views of example embodiments of a Huber safety needle in a closed configuration, showing a short hinge version and a long hinge version, respectively.
Figure 6B:
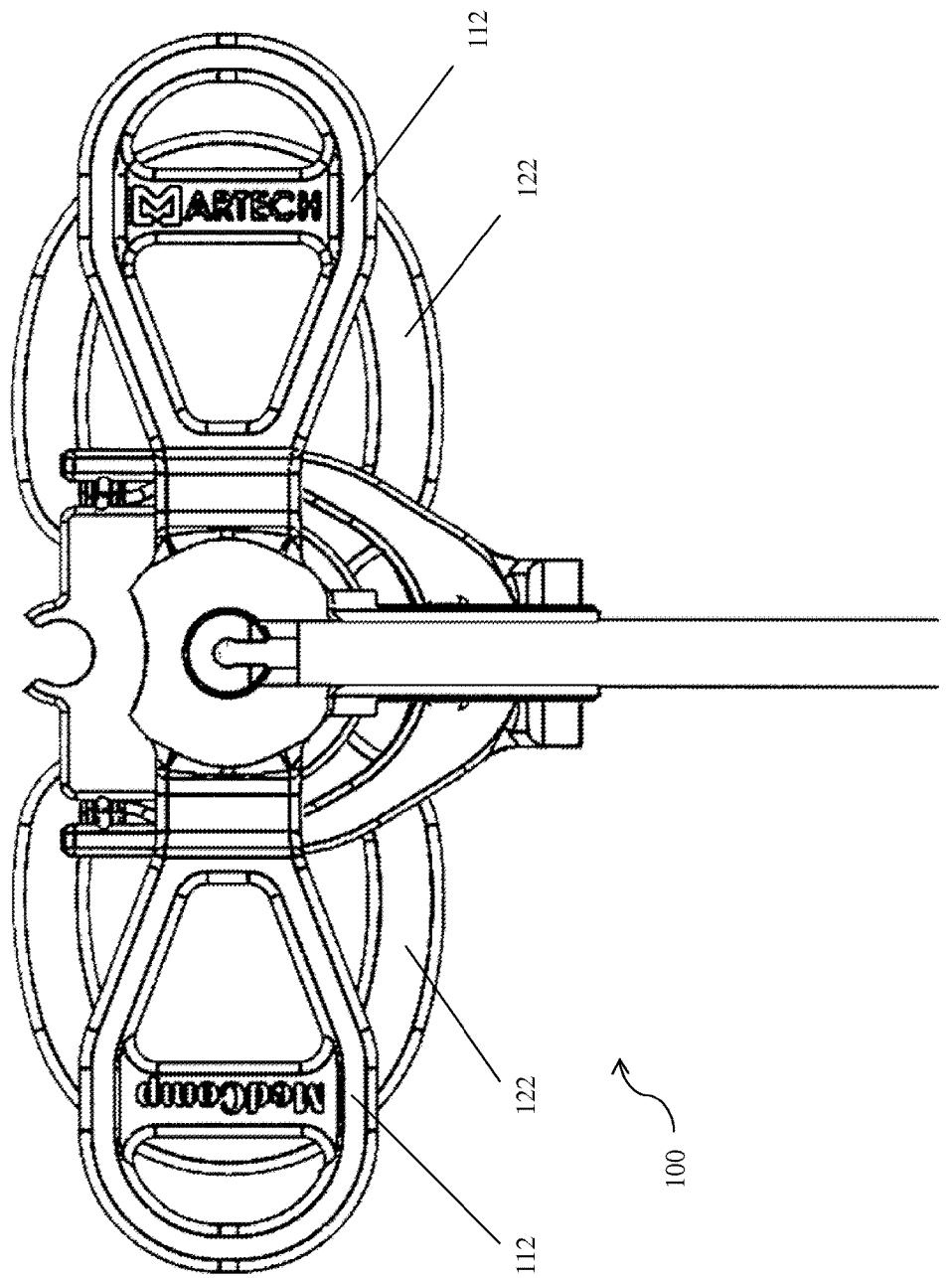

FIGS. 3A-3B illustrate side views of an example Huber safety needle assembly 100 in the closed configuration 150 in accordance with a first embodiment. FIGS. 14-15 illustrate cross-sectional views of an example Huber safety needle assembly 100 in accordance with a first embodiment. The hinge mechanism 130 can include an upper portion 132, a middle portion 134, and a lower portion 136. The upper portion 132 of the hinge mechanism 130 can be coupled to the upper portion 110 at an upper pivot point 133. The lower portion 136 of the hinge mechanism 130 can be coupled to the lower portion 120 at a lower pivot point 137. The middle portion 134 can couple the upper portion 132 and the lower portion 136 and can be configured to function as a middle pivot point. In at least one embodiment, the middle portion 134 can be a thinned area allowing the material to bend (or flex) as the Huber safety needle assembly 100 transitions from a closed configuration 150 to an open configuration 175 (see FIGS. 13A and 13B).

Figure 7A:
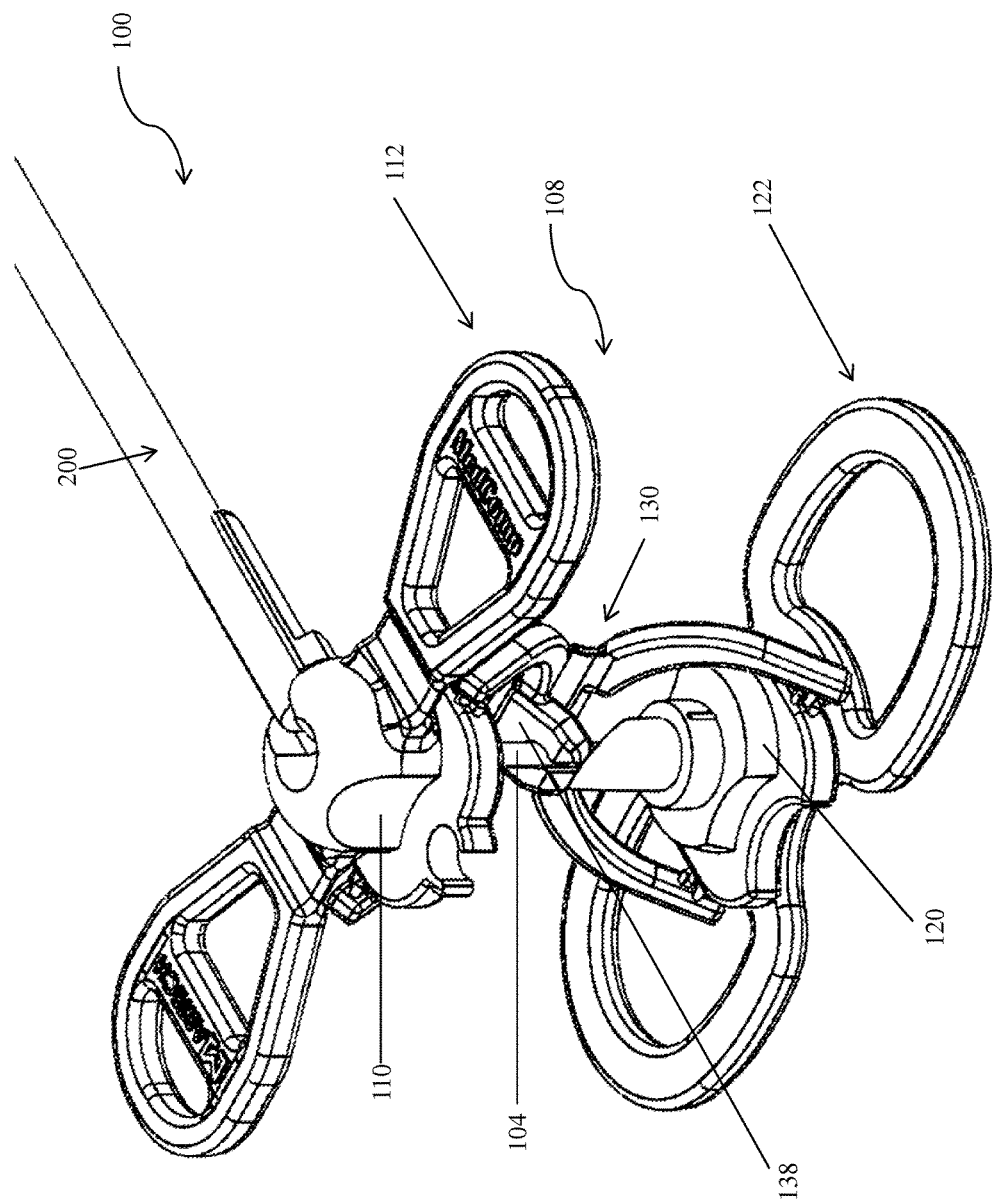
FIGS. 7A-7B are isometric views of example embodiments of a Huber safety needle in an open configuration, showing a short hinge version and a long hinge version, respectively.
Figure 7B:
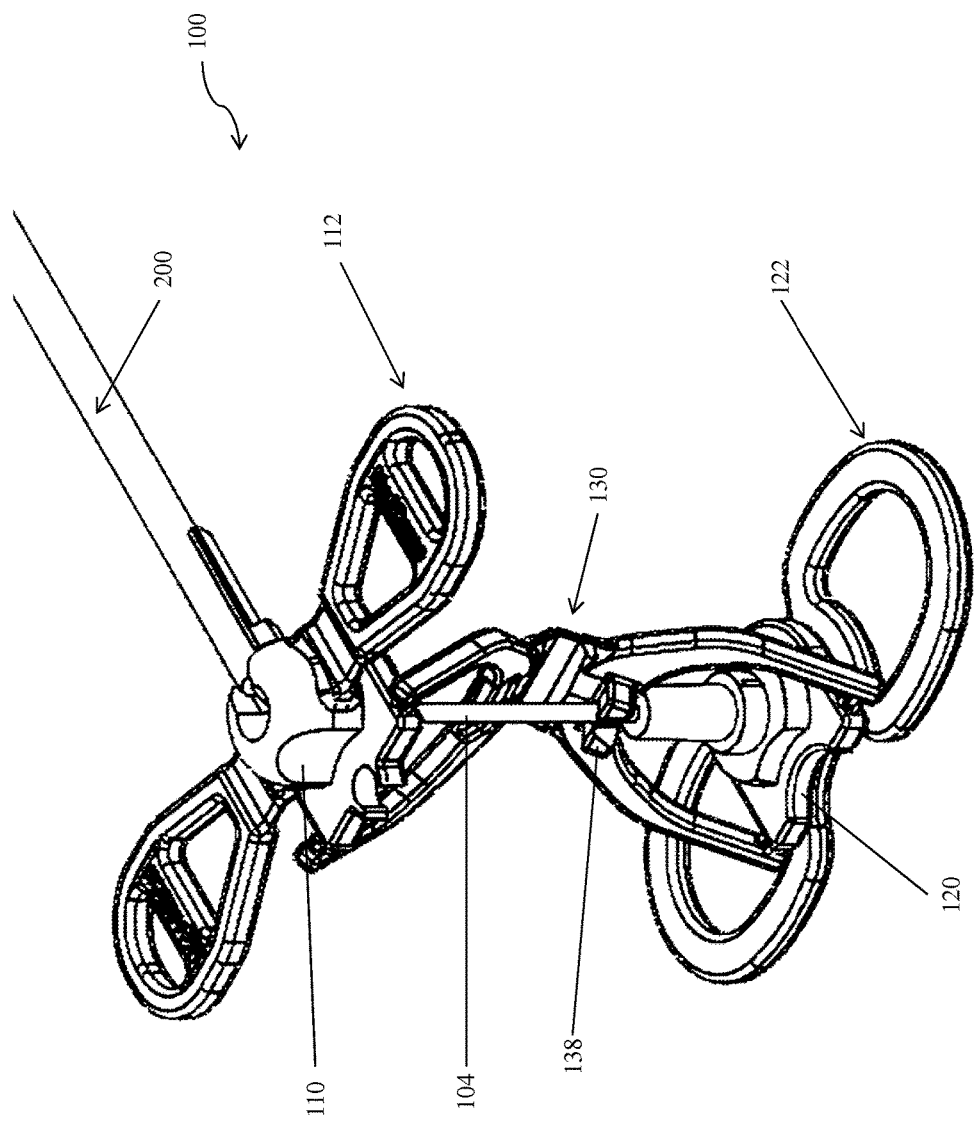
Figure 8A:
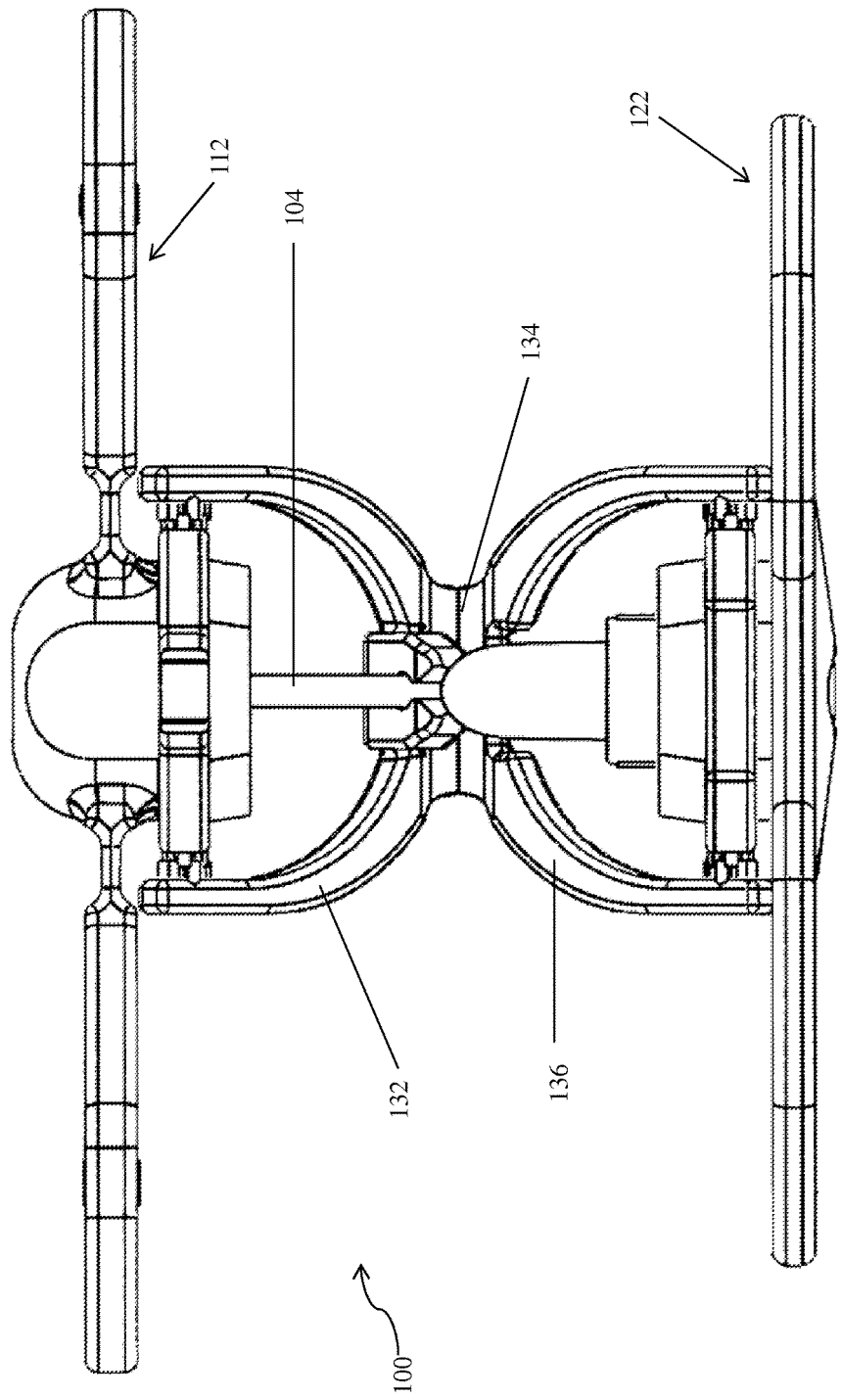
FIGS. 8A-8B are front views of example embodiments of a Huber safety needle in an open configuration, showing a short hinge version and a long hinge version, respectively.
Figure 8B:
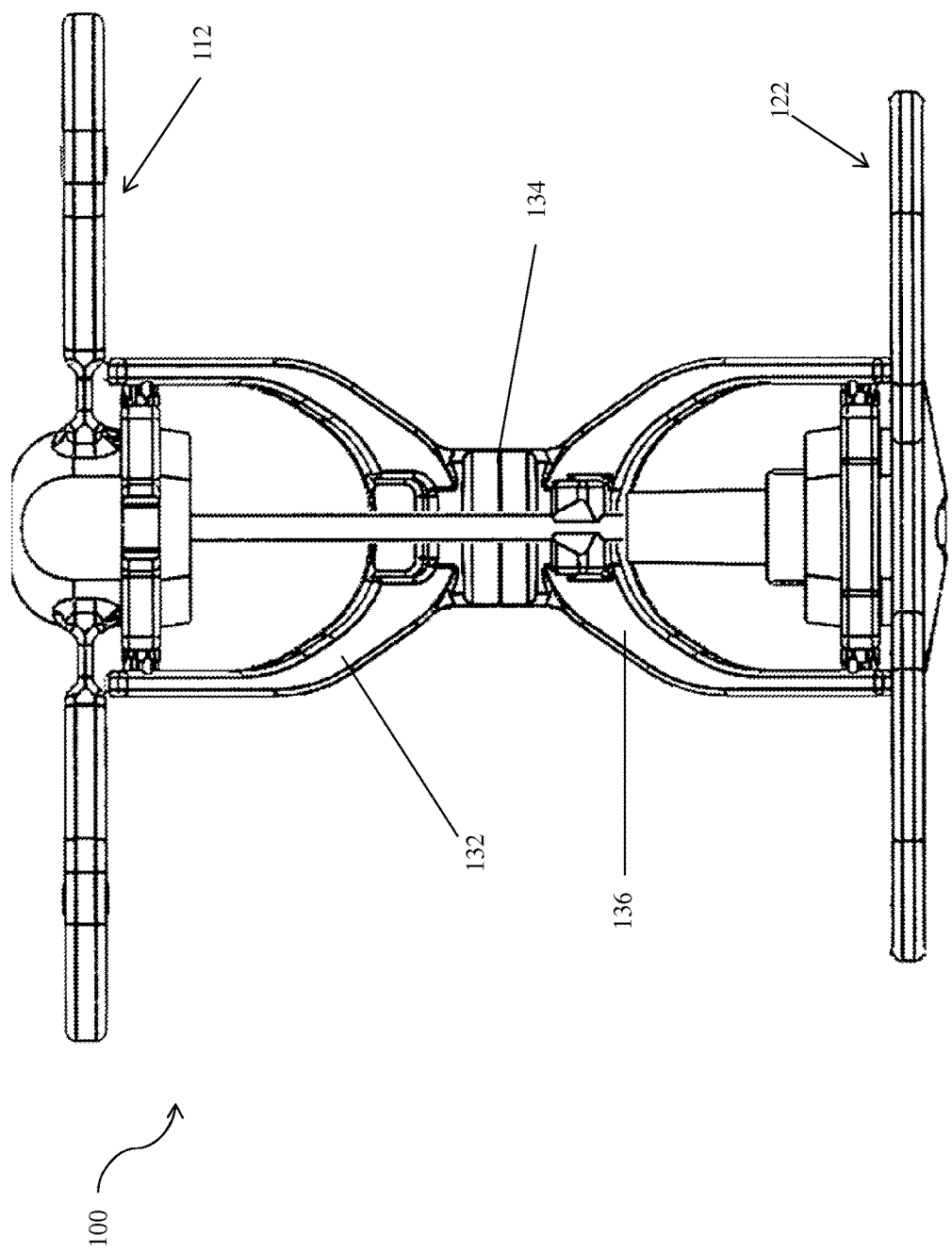

The hinge mechanism 130 can further include at least one attachment point 138 configured to secure the hinge mechanism 130 to the needle 104 when in the open configuration 175 (see FIGS. 7A-7B). The attachment point 138 can be any suitable means for securing the hinge mechanism 130 to the needle 104. In at least one embodiment, the at least one attachment point 138 can be a snap-fit configuration. In an alternative embodiment, the at least one attachment point 138 can be substantially L-shaped allowing the attachment point 138 to push past the needle 104 when transitioning from the closed configuration to the open configuration, thereby securing the needle 104 in the void formed in the substantially L-shaped attachment point 138. Depending on the configuration, the Huber safety needle assembly 100 can have a single attachment configuration or combination thereof.

FIGS. 14A-14B illustrate front cross-sectional views of an example Huber safety needle assembly 100 in a closed configuration 150 and an open configuration 175, respectively, in accordance with a first embodiment. These figures illustrate the transition from the closed configuration 150 to the open configuration 175. As can be appreciated in FIGS. 14A-14B, the lower portion 120 can be moved away from the upper portion 110 along the length of the needle 104. The movement of the lower portion 120 away from the upper portion 110 can allow the lower portion 120 to securely house the needle 104 and needle tip 106. In at least one embodiment, the needle 104 is fixed relative to the upper portion 110 allowing the lower portion 120 to slide along the longitudinal axis of the needle 104.

The upper and lower pivot points 133, 137 can be rotatable pin arrangements 135 configured to transition the needle assembly 100 between configurations (see FIGS. 14A-14B). In at least one embodiment, the middle portion 134 can function as a pin arrangement 135. The rotatable pin arrangement 135 can be configured to have a pivot point in substantially the same plane as the needle 104. The rotatable pin arrangement 135 can allow the pin to twist as the hinge mechanism 130 transitions the assembly 100 from one configuration 150, 175 to the other. The rotatable pin arrangement 135 can shorten the overall length of the hinge mechanism 130 compared to traditional mechanisms, thus creating a lower profile.

Figure 10A:
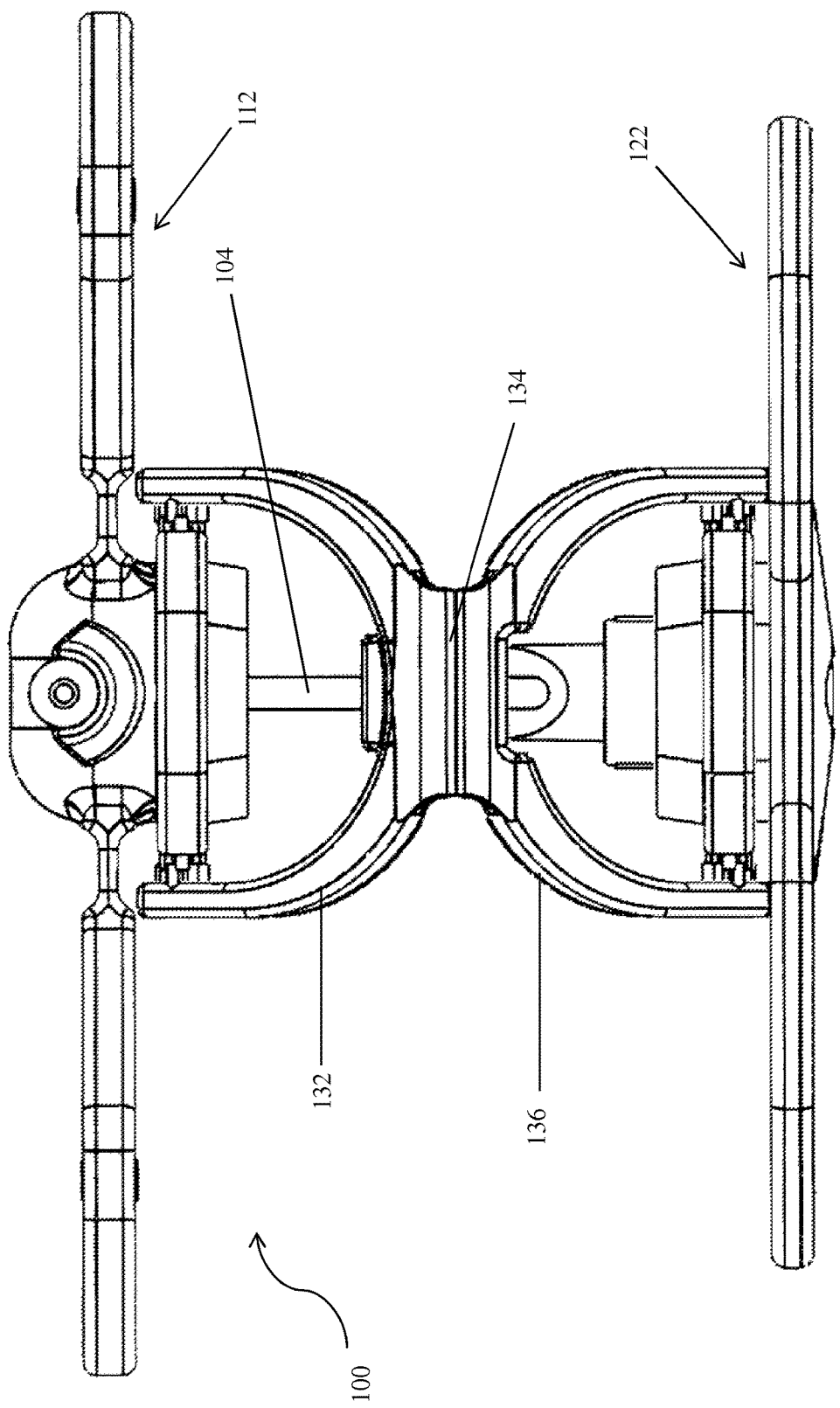
FIGS. 10A-10B are rear views of example embodiments of a Huber safety needle in an open configuration, showing a short hinge version and a long hinge version, respectively.
Figure 10B:
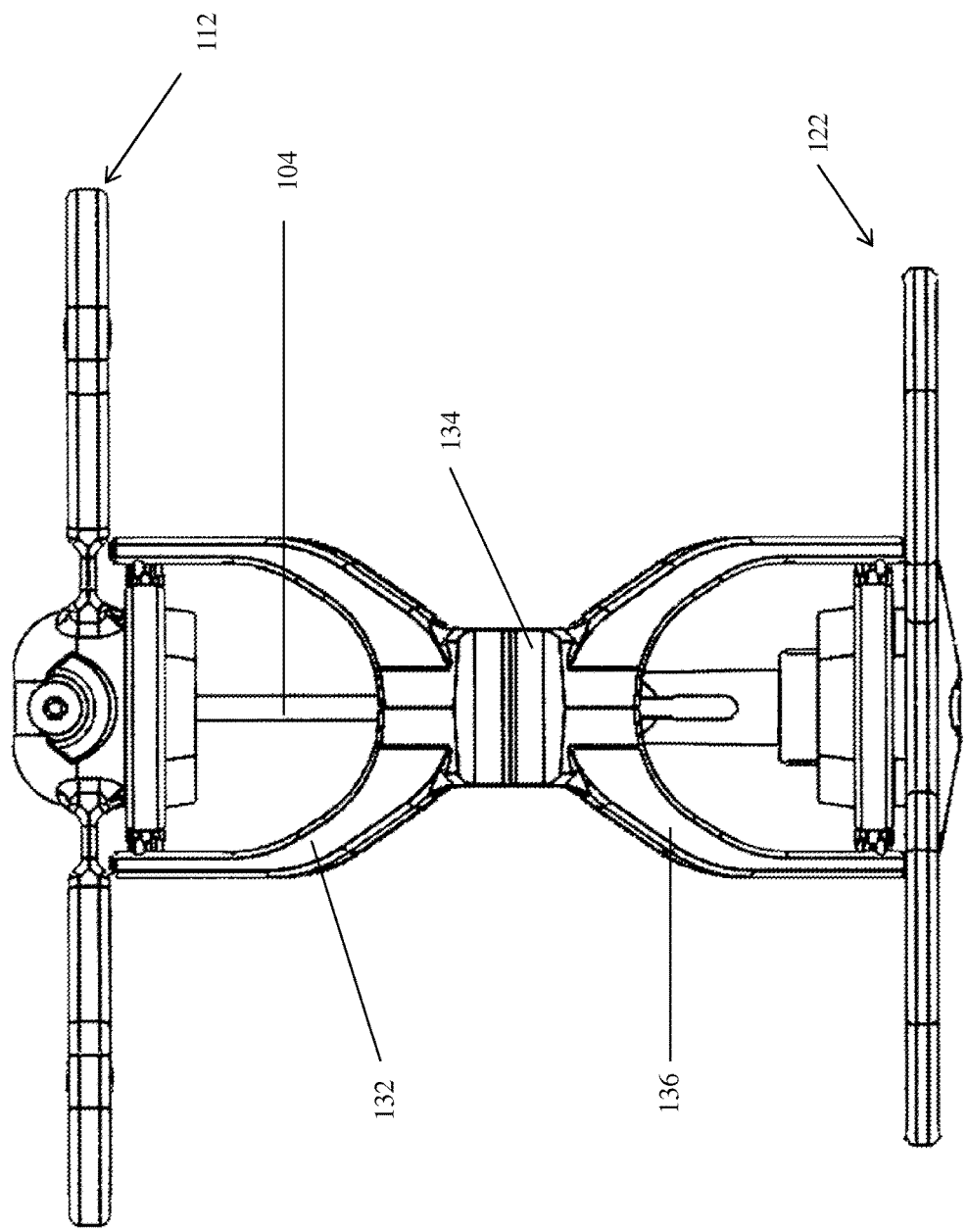
Figure 11B:
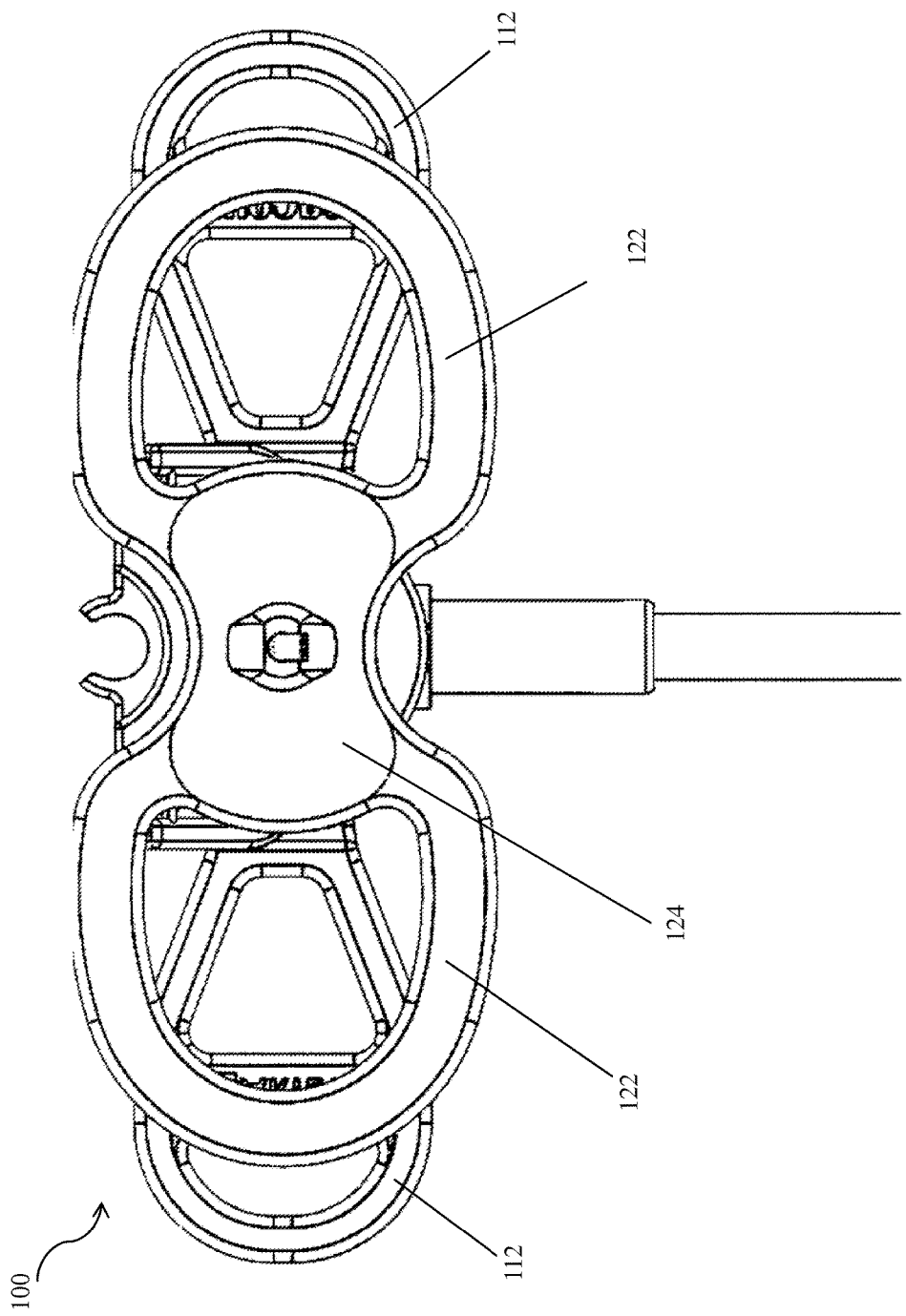
Figure 12A:
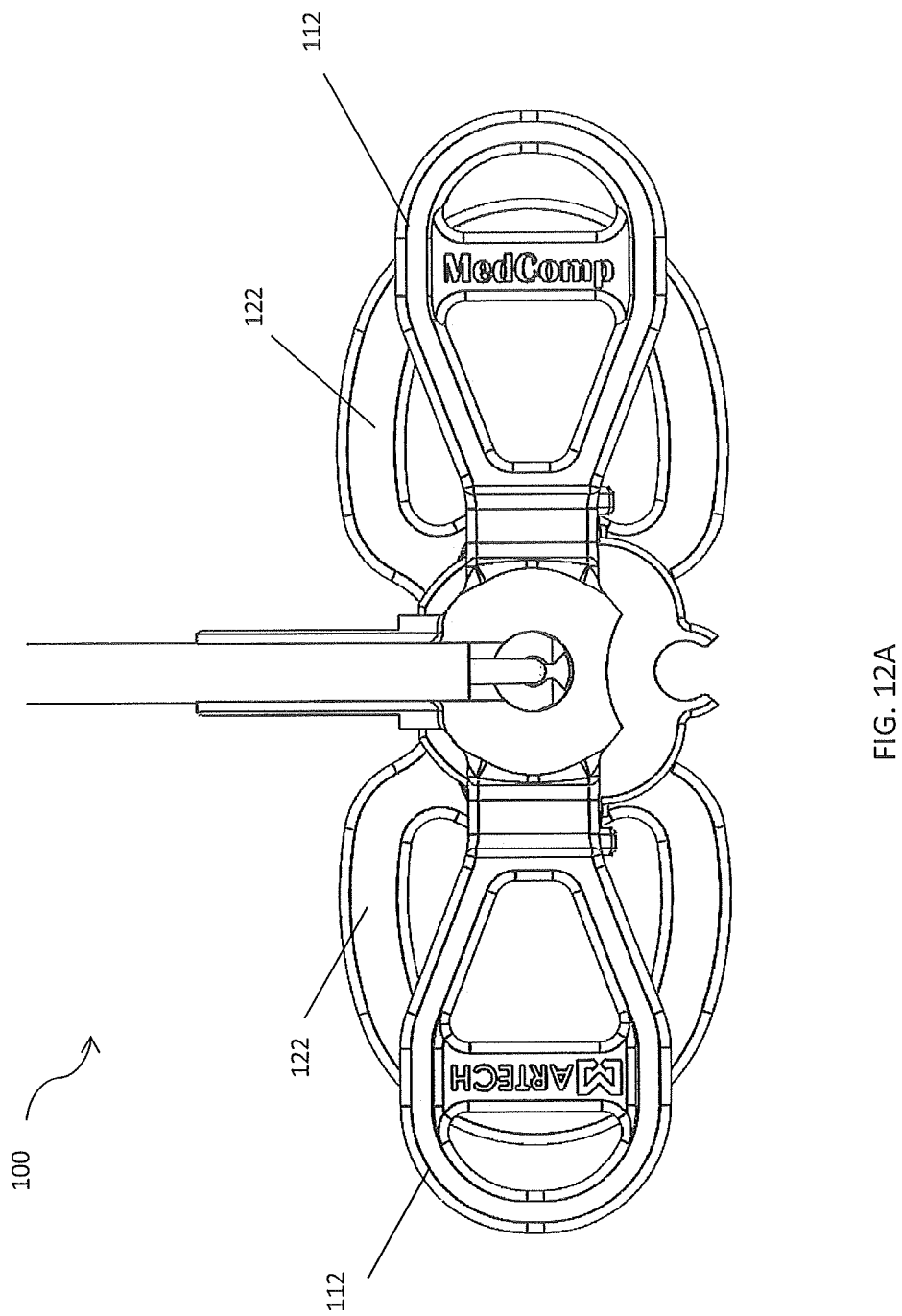
FIGS. 12A-12B are top views of example embodiments of a Huber safety needle in an open configuration, showing a short hinge version and a long hinge version, respectively.
Figure 12:
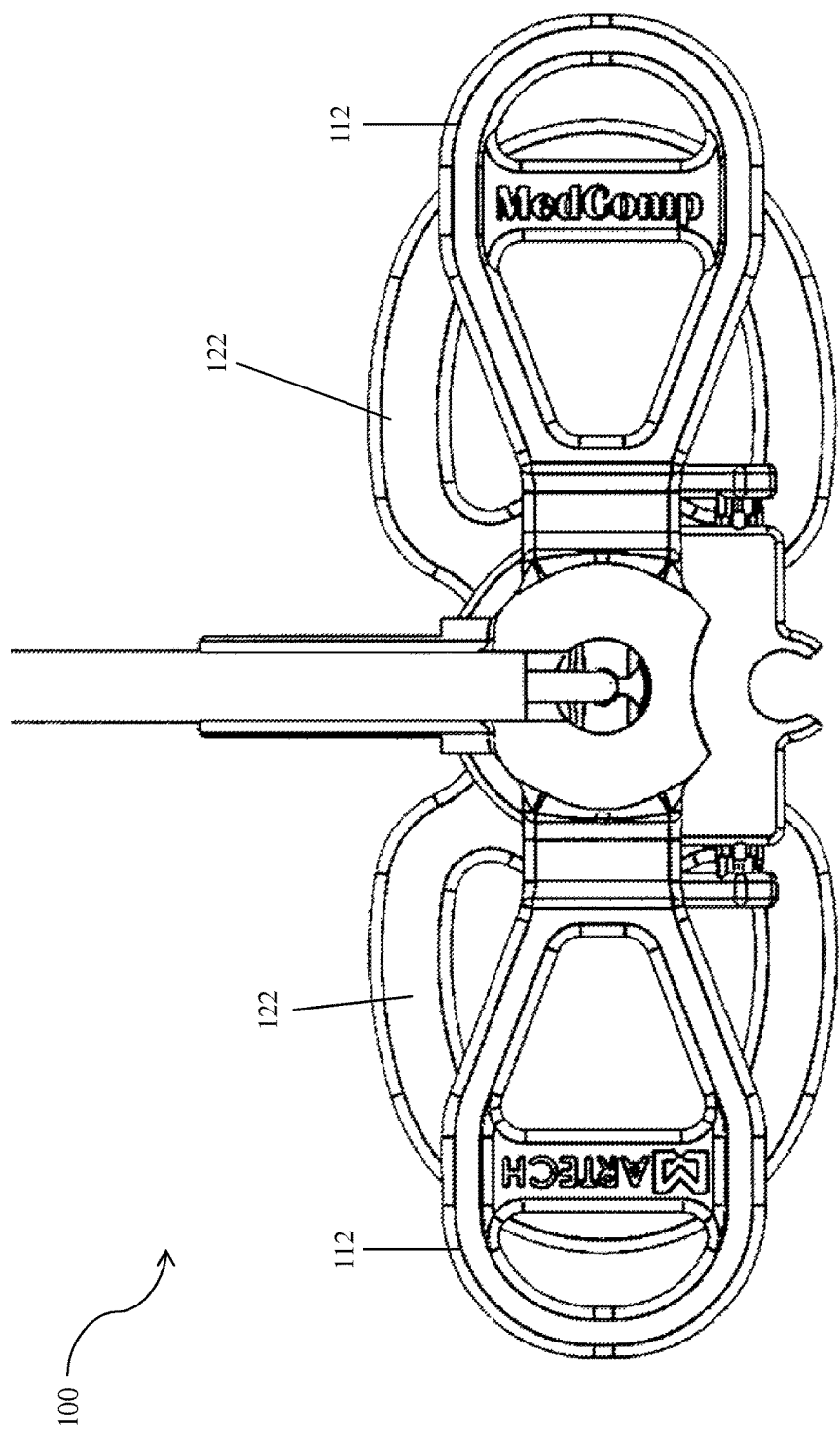

As can be appreciated in FIGS. 10A-10B, the upper and lower portion 132, 136 of the hinge mechanism 130 can be coupled to each side of the body 108 by a rotatable pin arrangement 135. The upper portion 132 of the hinge mechanism 130 can be substantially U-shaped and configured to couple to the upper portion 110 at each opposing end. Each opposing end can couple to the upper portion 110 using the rotatable pin arrangement 135 and be formed in substantially the same plane as the needle 104 (see FIGS. 14A-14B). The lower portion 136 of the hinge mechanism 130 can also form a substantially U-shape and be configured to couple the lower portion 120 at each opposing end. Each opposing end can couple to the lower portion 120 using the rotatable pin arrangement 135. The opposing ends and rotatable pin arrangement 135 can form a plane that substantially passes through the longitudinal axis of the needle 104. The rotatable pin arrangement 135 can couple the upper portion 132 of the hinge mechanism 130 to the upper portion 110 and the lower portion 136 of the hinge mechanism 130 to the lower portion 120. In at least one embodiment, the rotatable pin 135 can have a substantially square cross-section with respect to a plane perpendicular to the cross-sectional view shown in FIGS. 14A-14B. In alternative embodiments, the rotatable pin 135 can have a substantially circular, oval, triangular, or polygonal cross-section.

The Huber safety needle assembly 100 can be configured to transition from the closed configuration 150 to an open configuration 175 by applying a separating force along the longitudinal axis of the needle 104, or an axis or axes parallel thereto. The upper and lower gripping portions 112, 122 can be positioned on each side of the needle assembly 100 thereby keeping a transition force in axial alignment with the needle 104 when transitioning the needle assembly 100 between the closed 150 and open configurations 175. In at least one embodiment, the Huber safety needle assembly 100 is irreversibly transitionable from the closed configuration 150 to the open configuration 175. As the separation force is applied, the upper portion 110 and lower portion 120 are displaced with respect to one another and the needle 104 passes through the lower portion 120, such that the needle tip 106 does not extend beyond the bottom surface of the lower portion 120 (see FIG. 14A). The assembly 100 can then be secured in the open configuration 175 as the needle is secured by the at least one attachment point 138 (see FIG. 7B). In at least one embodiment, the user can apply a separating force by securing the lower portion 120 in a fixed position and applying the force at the upper portion 110 along the plane of the needle 104 in a direction away from the lower portion 120. In alternative embodiments, depending on the arrangement of the needle assembly 100, the separation force can be applied at both the lower portion 120 and the upper portion 110 or only at the lower portion 110.

Figure 9A:
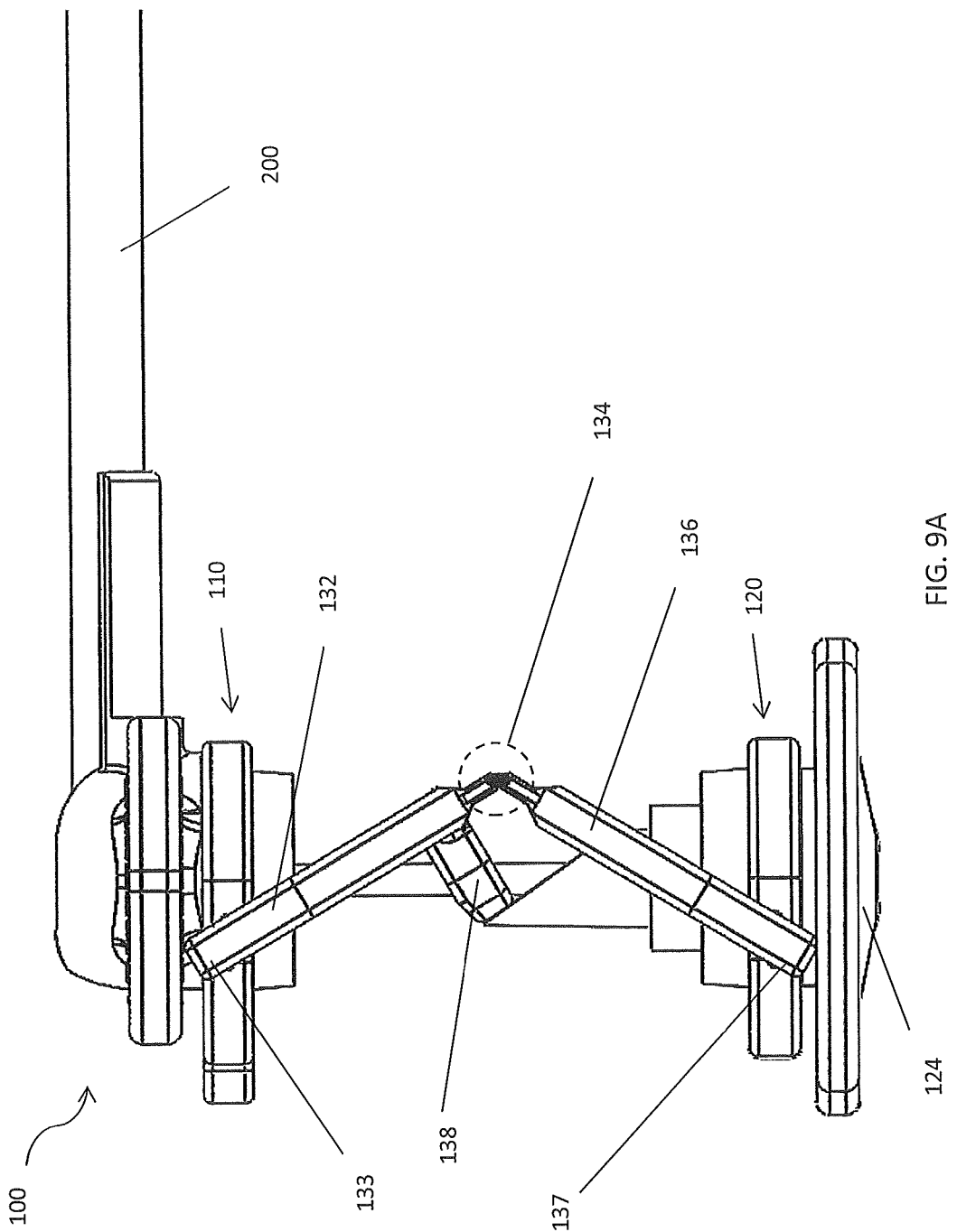
FIGS. 9A-9B are right side views of example embodiments of a Huber safety needle in an open configuration, showing a short hinge version and a long hinge version, respectively.
Figure 9B:
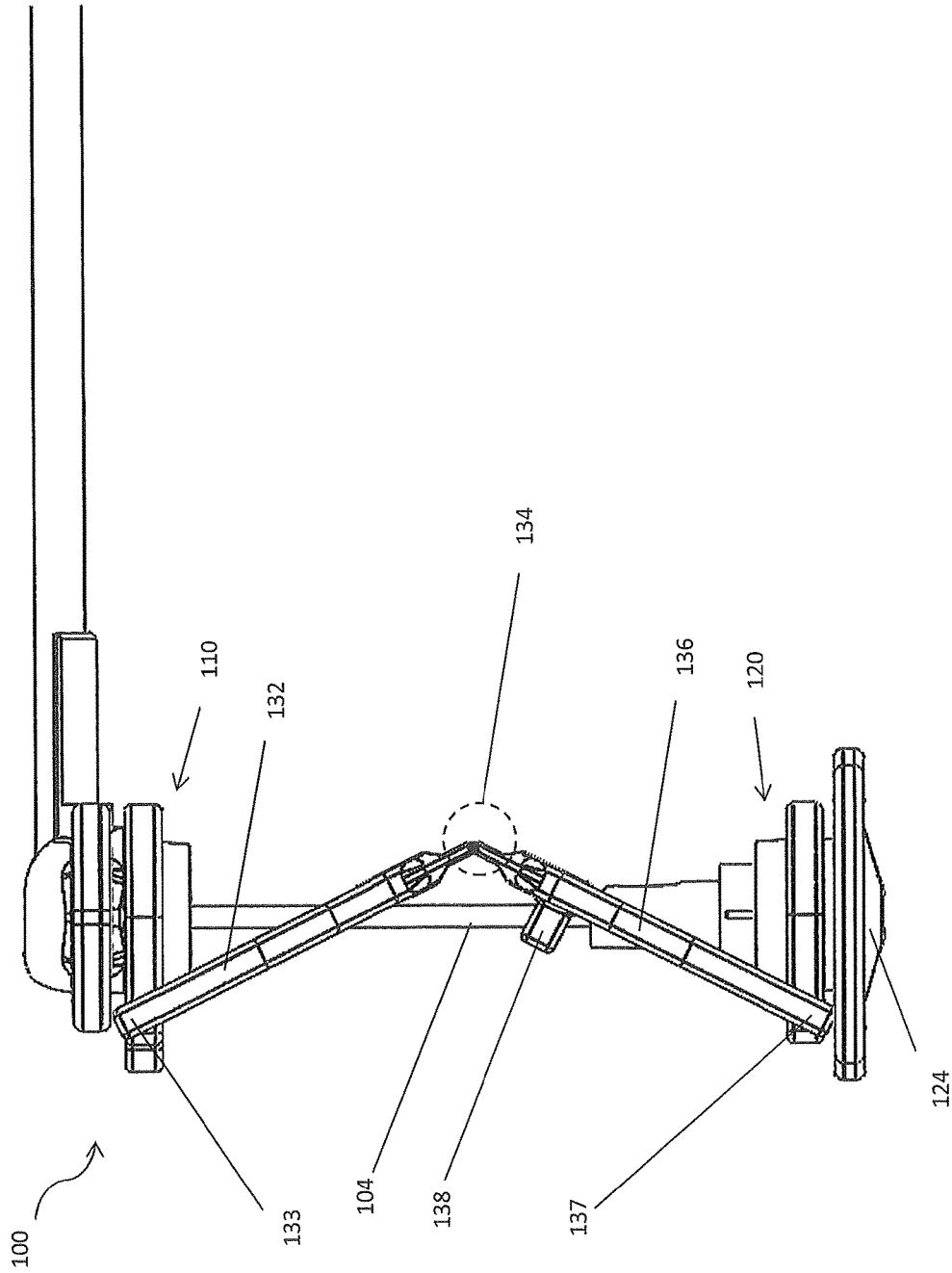

The separation force can operate the hinge mechanism 130, thereby separating the upper portion 110 and the lower portion 120 and securing the needle tip 106 within the lower portion 120. The attachment point 138 can secure the hinge mechanism 130 to the needle 104 further securing the needle assembly 100 in the open configuration 175. As can be appreciated in FIGS. 7A-7B, the upper portion 110 and the lower portion 120 are displaced along the length of the needle 104 and the needle 104 can be secured to the Huber safety needle assembly 100 at the attachment point 138. The upper portion 132 and lower portion 136 of the hinge mechanism 130 can be substantially perpendicular relative to their orientation in the closed configuration 150 (see FIG. 3B). In at least one embodiment, the hinge mechanism 130 can be substantially vertical in the open configuration 175 (see FIG. 9B).

In at least one embodiment, the bottom surface of the lower portion 120 can include a protrusion configured to ensure the entire needle tip 106 is secured within the lower portion 120.

FIGS. 16-19 illustrate various views of an example Huber safety needle assembly 500 in accordance with a second embodiment. The Huber safety needle assembly 500 can include a body 508 configured to secure a needle 504. The needle 504 can have a substantially hollow core configured to allow fluid flow therethrough and have a cross-sectional shape that is substantially circular, oval, triangular, rectangular, polygonal, or combinations thereof. In at least one embodiment, different gauge needles 504 can be used for different applications and different delivery fluids. The needle 504 can be made of any suitable material, such as stainless steel. The body 508 can have an upper portion 510 and a lower portion 520. The body 508 can have any desired shape that provides a hollow portion configured to receive the needle 504. The upper portion 510 can be configured to detachably couple needle assembly 500 to a catheter 600. For example, the body 508 can be configured to matingly receive the catheter 600. In at least one embodiment, the catheter 600 is in fluid communication with the body 508 and the needle 504 providing a pathway for drugs, solutions, compounds, blood, or some other substance to be delivered through the needle 504. The upper portion 510 can further be configured to secure the needle 504 within the body 508. The lower portion 520 can be configured to receive at least a portion of the needle 504. In at least one embodiment, the lower portion 520 can have an aperture formed therein configured to allow the needle 504 to extend through the lower portion 520. The aperture can be configured to accommodate various needle 504 sizes and gauges, as well as any beveled tip of the needle 504. The lower portion 520 can further include a skin plate 524 on the bottom surface of the lower portion 520. The upper portion 510 and the lower portion 520 can each include upper and lower gripping portions 512, 522 respectively. The upper gripping portion 512 and lower gripping portion 522 can each have opposing sides, each opposing side forming a substantially loop shape. The upper gripping portion 512 and the lower gripping portion 522 can assist a user, or technician, with insertion of the Huber safety needle assembly 500.

The body 508 can further include a hinge mechanism 530. The hinge mechanism 530 can operably couple the upper portion 510 and the lower portion 520. The hinge mechanism 530 can allow the body 508 to transition from a closed configuration 550 to an open configuration 575 (see FIGS. 16A-16B). The closed configuration 550 can allow at least a portion of the needle 504, specifically the needle tip 506, to be exposed from the lower portion 520, thus allowing insertion of the needle 504. In at least one embodiment, the needle 504 and needle tip 506 can extend beyond the bottom surface of the lower portion 520. In alternative embodiments, only the needle tip 506 can extend beyond the bottom surface of the lower portion 520.

Figures 16A, 16B:
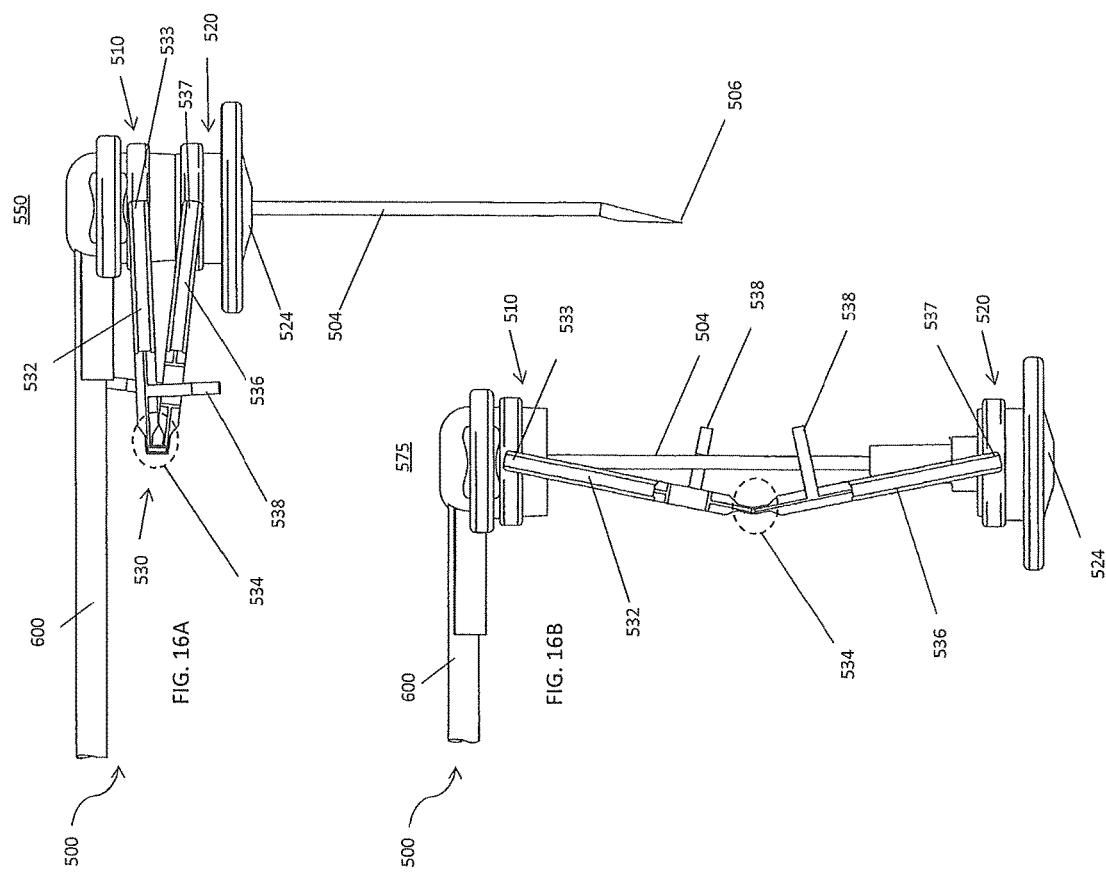
FIGS. 16A-16B are left side views of example second embodiments of a Huber safety needle in a closed configuration and an open configuration, respectively.

As can be appreciated in FIG. 16A, in the closed configuration 550, the upper portion 510 and the lower portion 520 can be touching or substantially close to touching. Additionally, the upper gripping portion 512 and the lower gripping portion 522 can be substantially parallel to one another and in a plane perpendicular to the needle 504. In alternative embodiments, the upper gripping portion 512 and the lower gripping portion 522 can be substantially perpendicular to one another with the lower portion 520 and lower gripping portion 522 configured to position the skin plate 524 against a patient and the upper gripping portion 512 being substantially perpendicular thereto. Alternatively, the first gripping portion 512 can be positioned at any angle between parallel and perpendicular relative to the lower gripping portion 522.

The hinge mechanism 530 can include an upper portion 532, a middle portion 534, and a lower portion 536. The upper portion 532 of the hinge mechanism 530 can be coupled to the upper portion 510 at an upper pivot point 533. The lower portion 536 of the hinge mechanism 530 can be coupled to the lower portion 520 at a lower pivot point 537. The middle portion 534 can couple the upper portion 532 and the lower portion 536 and can be configured to function as a third pivot point. In at least one embodiment, the middle portion 534 can be a thinned area allowing the material to bend (or flex) as the Huber safety needle assembly 500 transitions from a closed configuration 550 to an open configuration 575 (see FIGS. 16A-16B).

The hinge mechanism 530 can further include at least one attachment point 538 configured to secure the hinge mechanism 530 to the needle 504 when in the open configuration 575. The attachment point 538 can be any suitable means for securing the hinge mechanism 530 to the needle 504. In at least one embodiment, the at least one attachment point 538 can be a snap-fit configuration. In an alternative embodiment, the at least one attachment point 538 can be substantially L-shaped allowing the attachment point 538 to push past the needle 504 when transitioning from the closed configuration 550 to the open configuration 575, thereby securing the needle 504 in the void formed in the substantially L-shaped attachment point 538. As can be appreciated in the in FIGS. 16A and 16B, the Huber safety needle assembly 500 can include two attachment points 538, one disposed on each of the upper portion 532 and the lower portion 536. The Huber safety needle assembly 500 can have single attachment point 538. The single attachment point 538 can be on the upper portion 532, or on the lower portion 536 of the hinge mechanism 530. Depending on the configuration, the Huber safety needle assembly 500 can have a single attachment configuration or a combination thereof.

Figure 18:
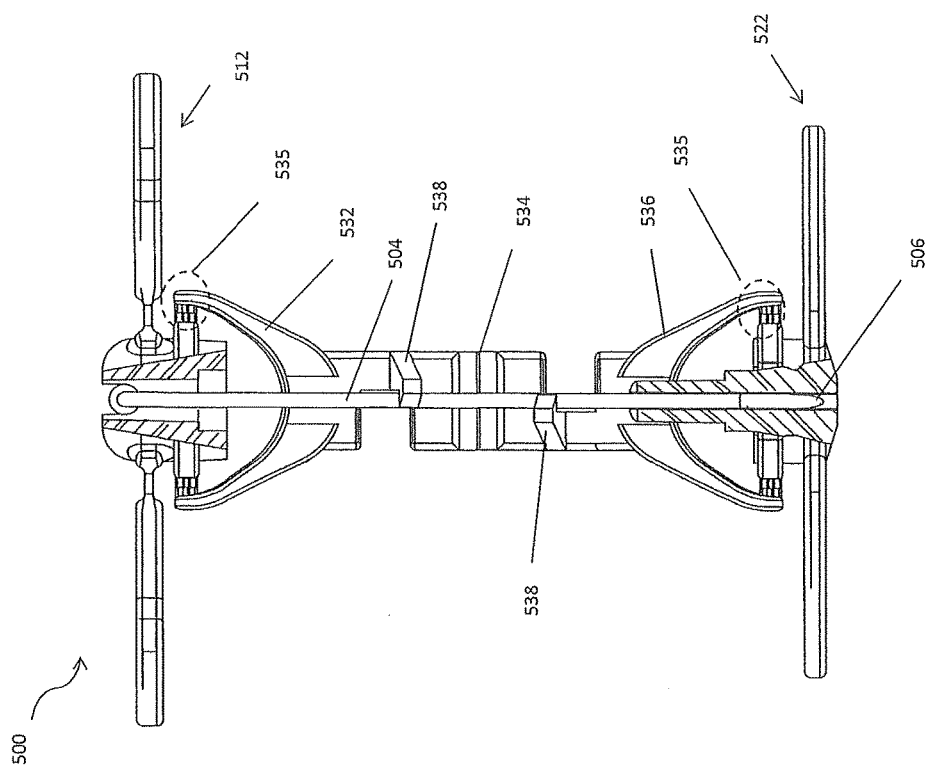
FIG. 18 is front a cross-sectional view of an example second embodiment of a Huber safety needle in an open configuration.
Figure 19:
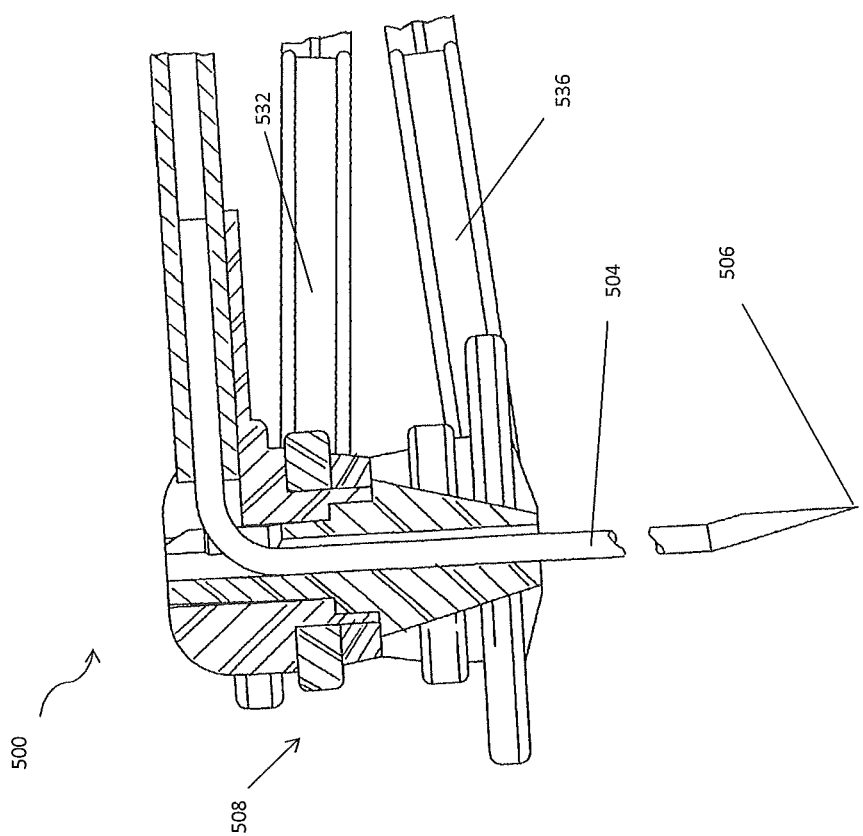
FIG. 19 is a right side view of an example second embodiment of a Huber safety needle in a closed configuration.
Figure 20A:
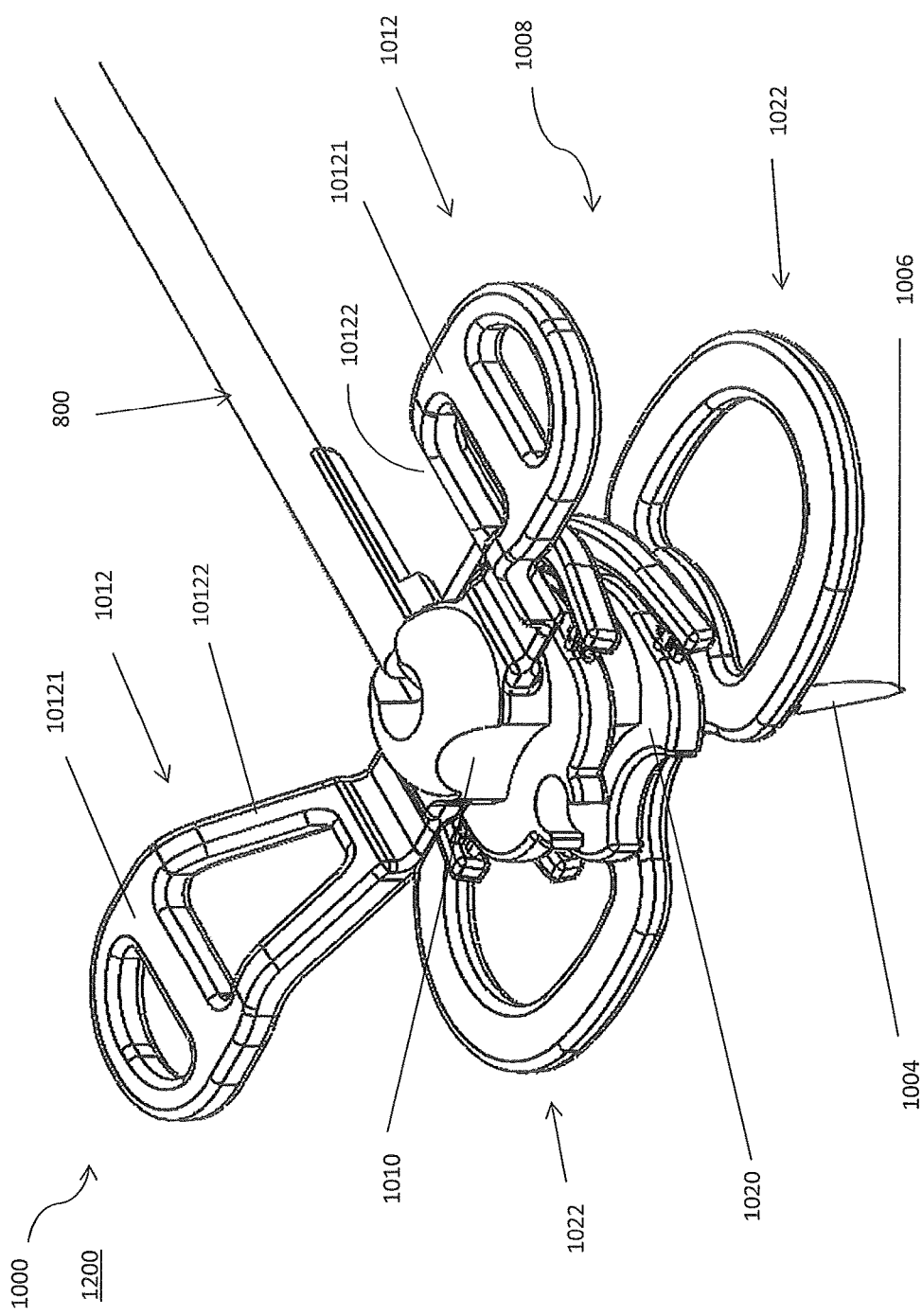
FIGS. 20A-20B are isometric views of example third embodiments of a Huber safety needle with the upper gripping portion in a first configuration, showing the assembly in a closed configuration and open configuration, respectively.
Figure 20B:
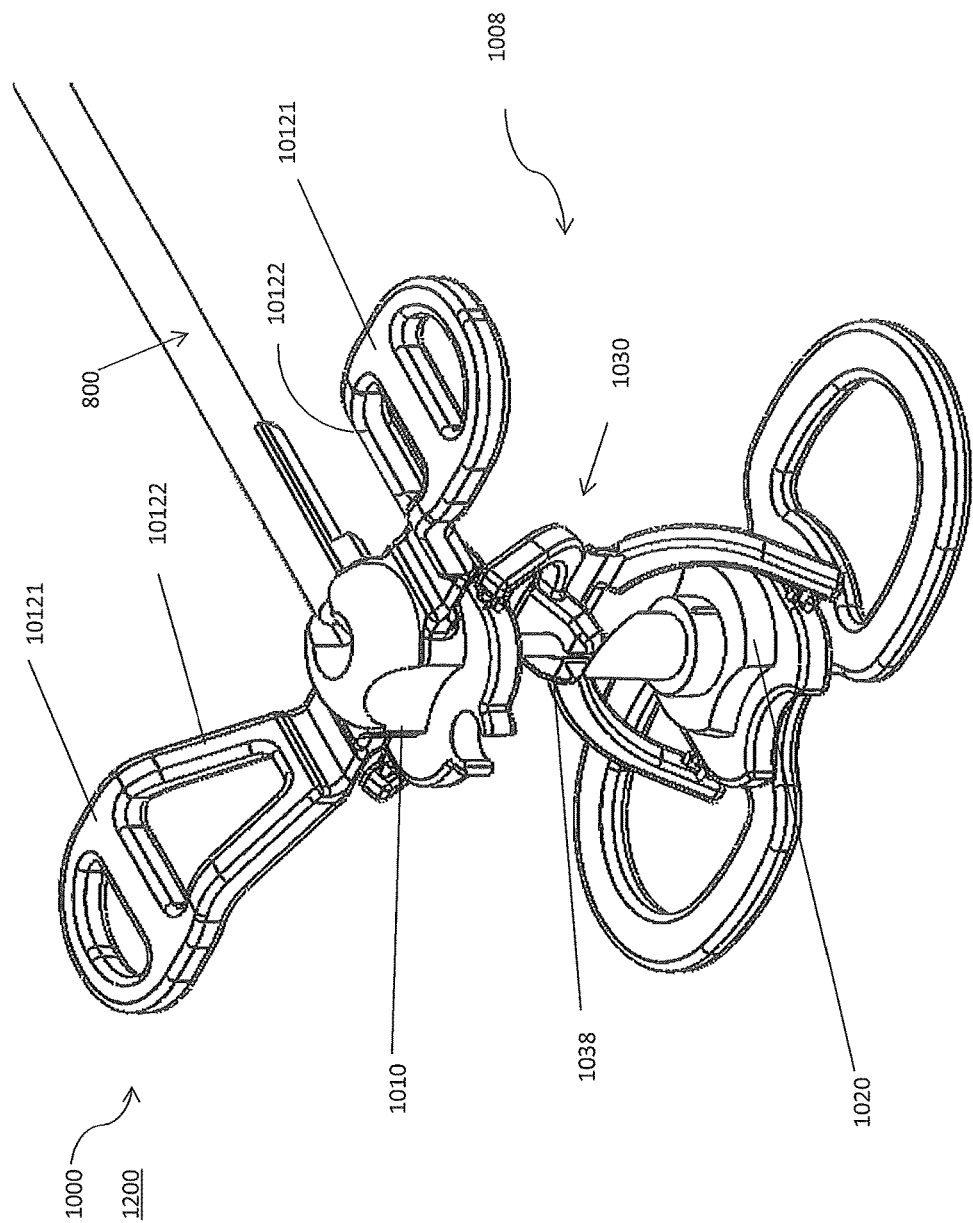
Figure 21A:
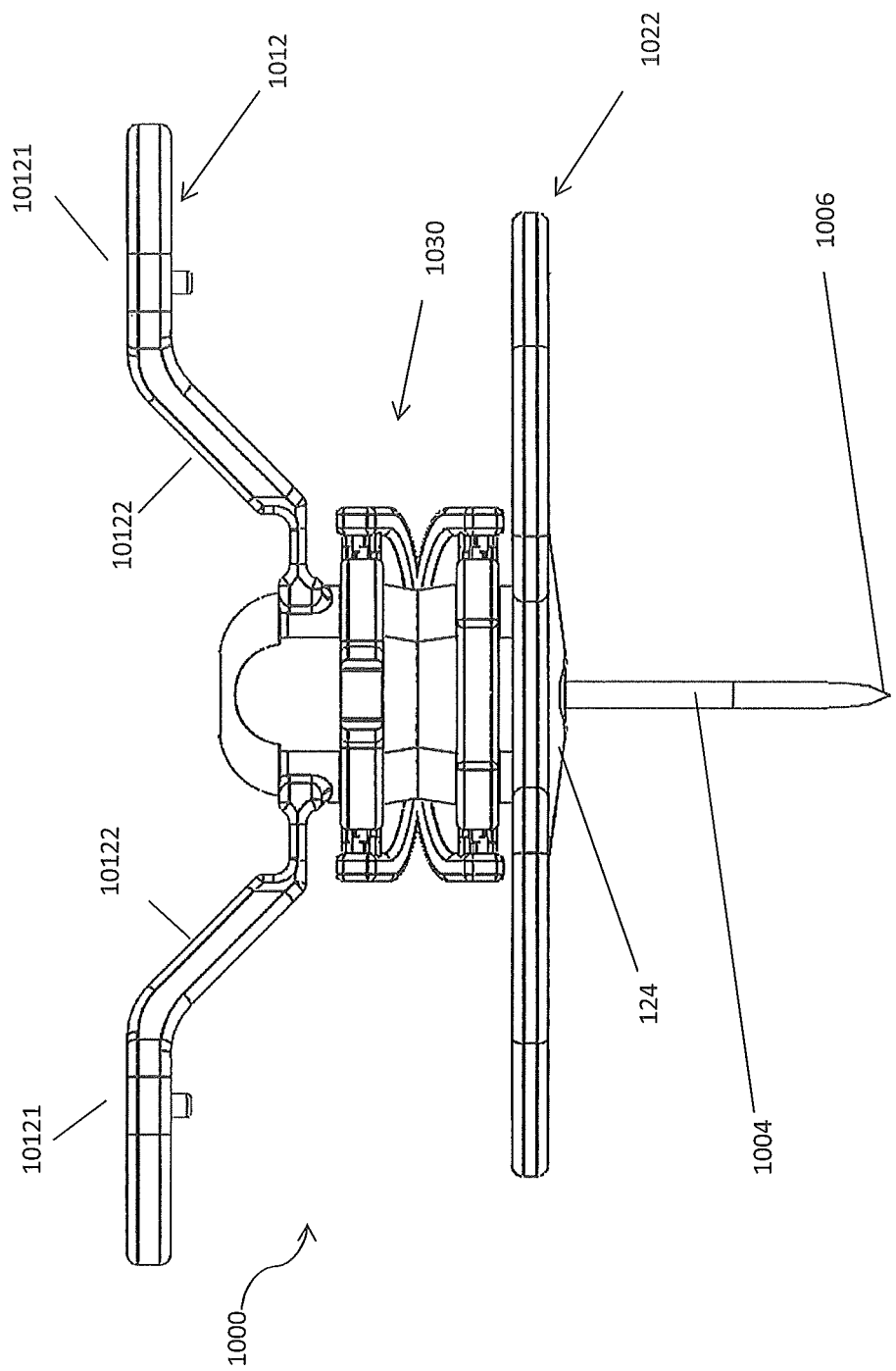
FIGS. 21A-21B are front views of example third embodiments of a Huber safety needle with the upper gripping portion in a first configuration, showing the assembly in a closed configuration and open configuration, respectively.
Figure 21B:
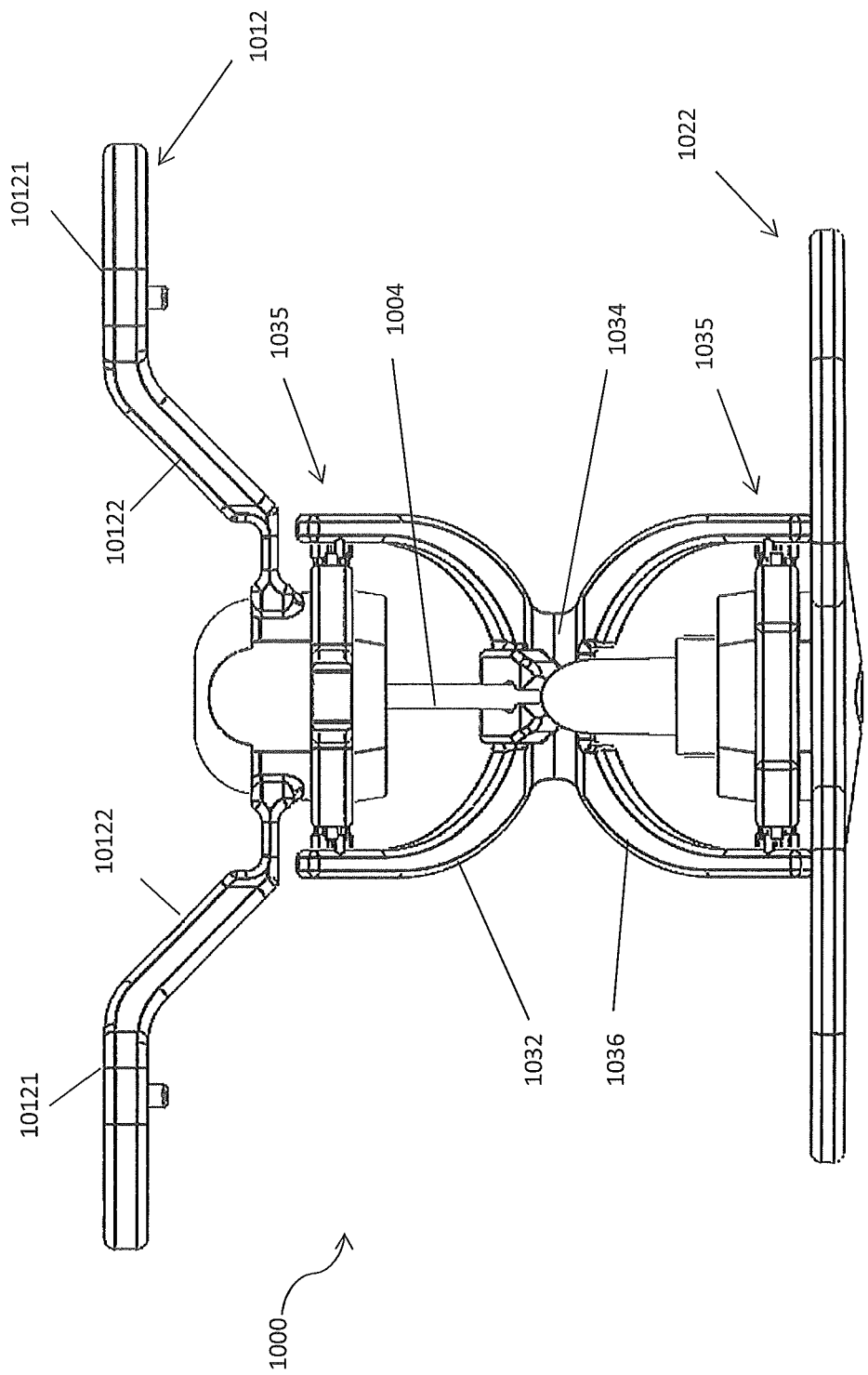
Figure 22A:
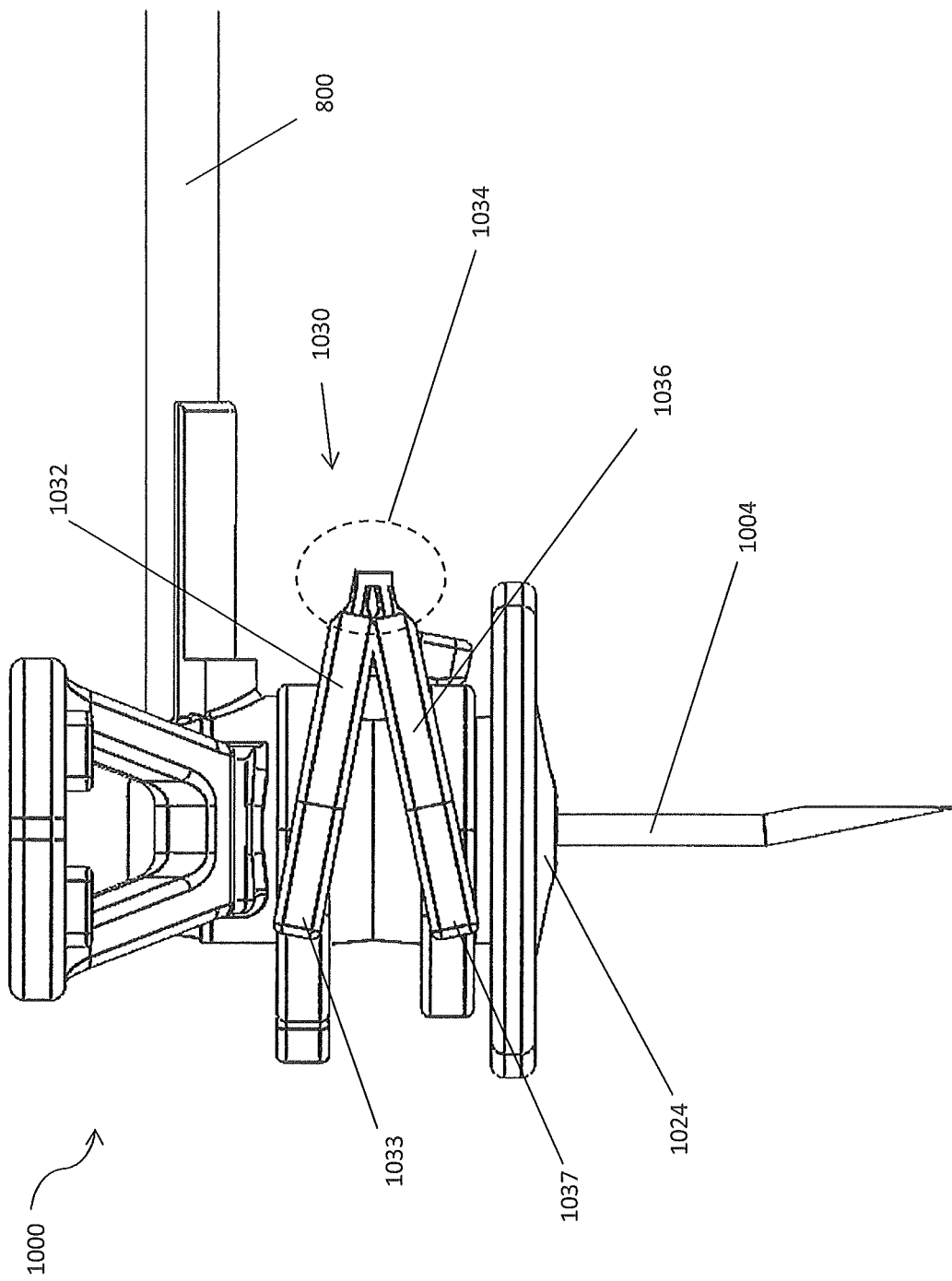
FIGS. 22A-22B are right side views of example third embodiments of a Huber safety needle with the upper gripping portion in a first configuration, showing the assembly in a closed configuration and open configuration, respectively.
Figure 22B:
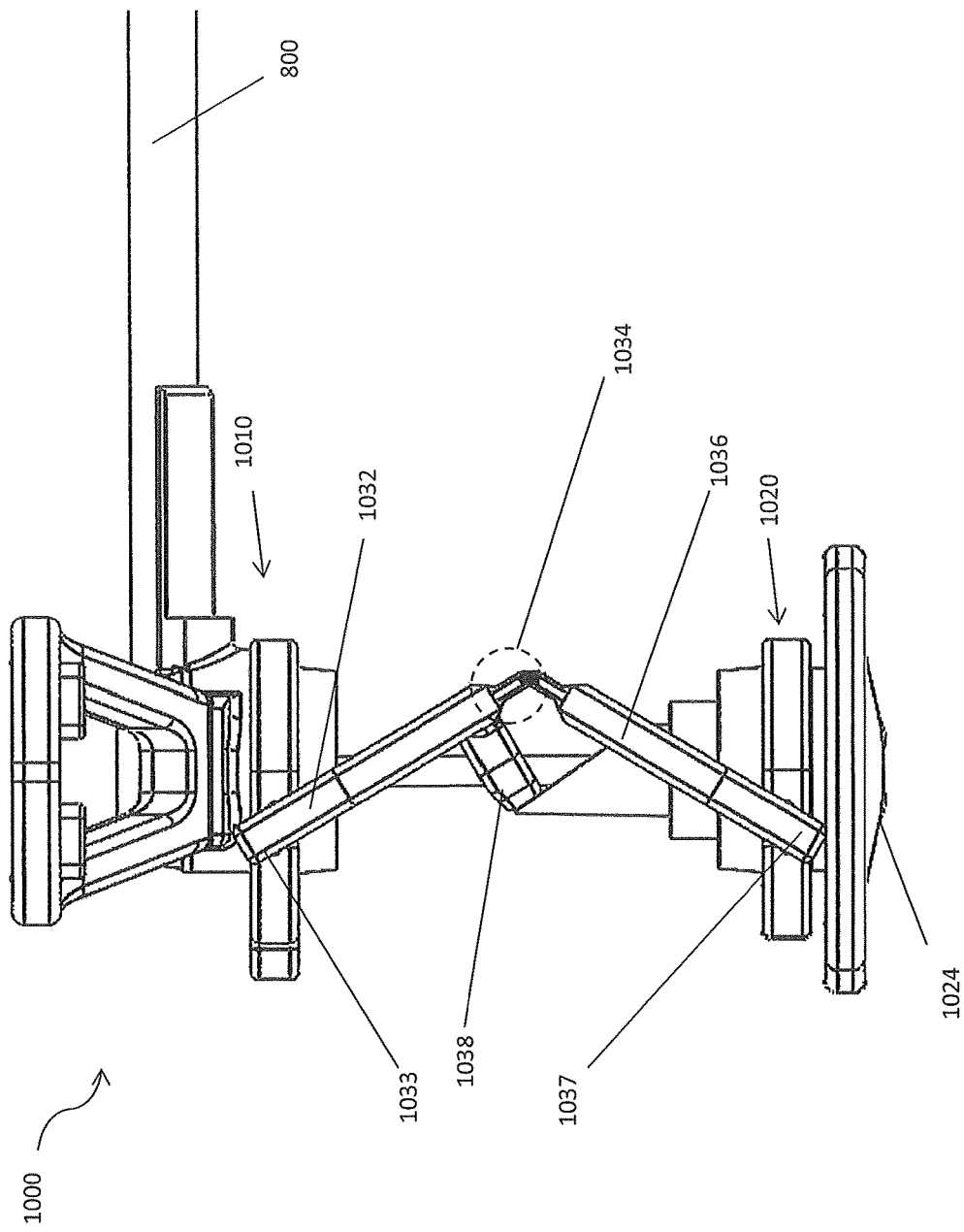
Figure 23A:
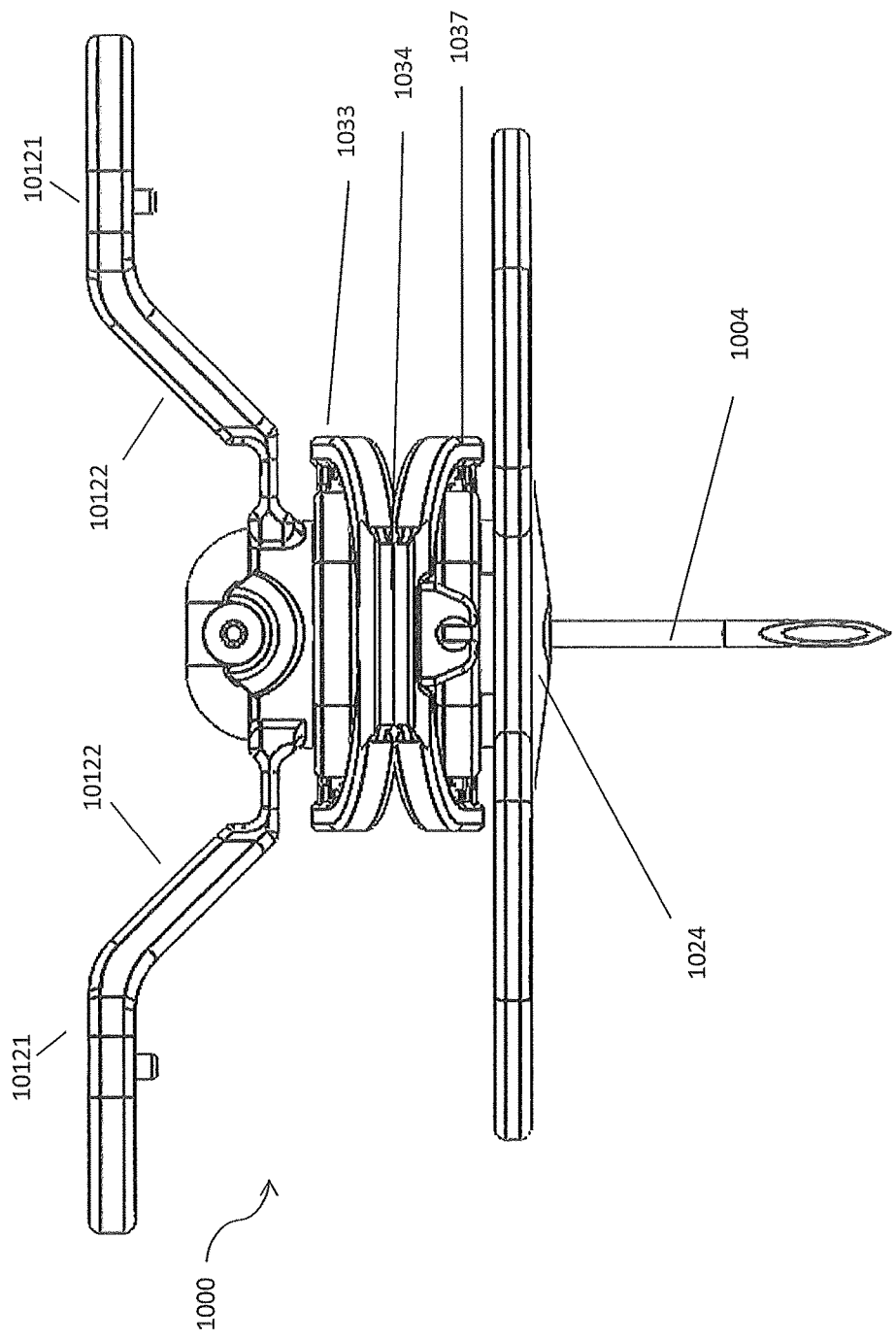
FIGS. 23A-23B are rear views of example third embodiments of a Huber safety needle with the upper gripping portion in a first configuration, showing the assembly in a closed configuration and open configuration, respectively.
Figure 23B:
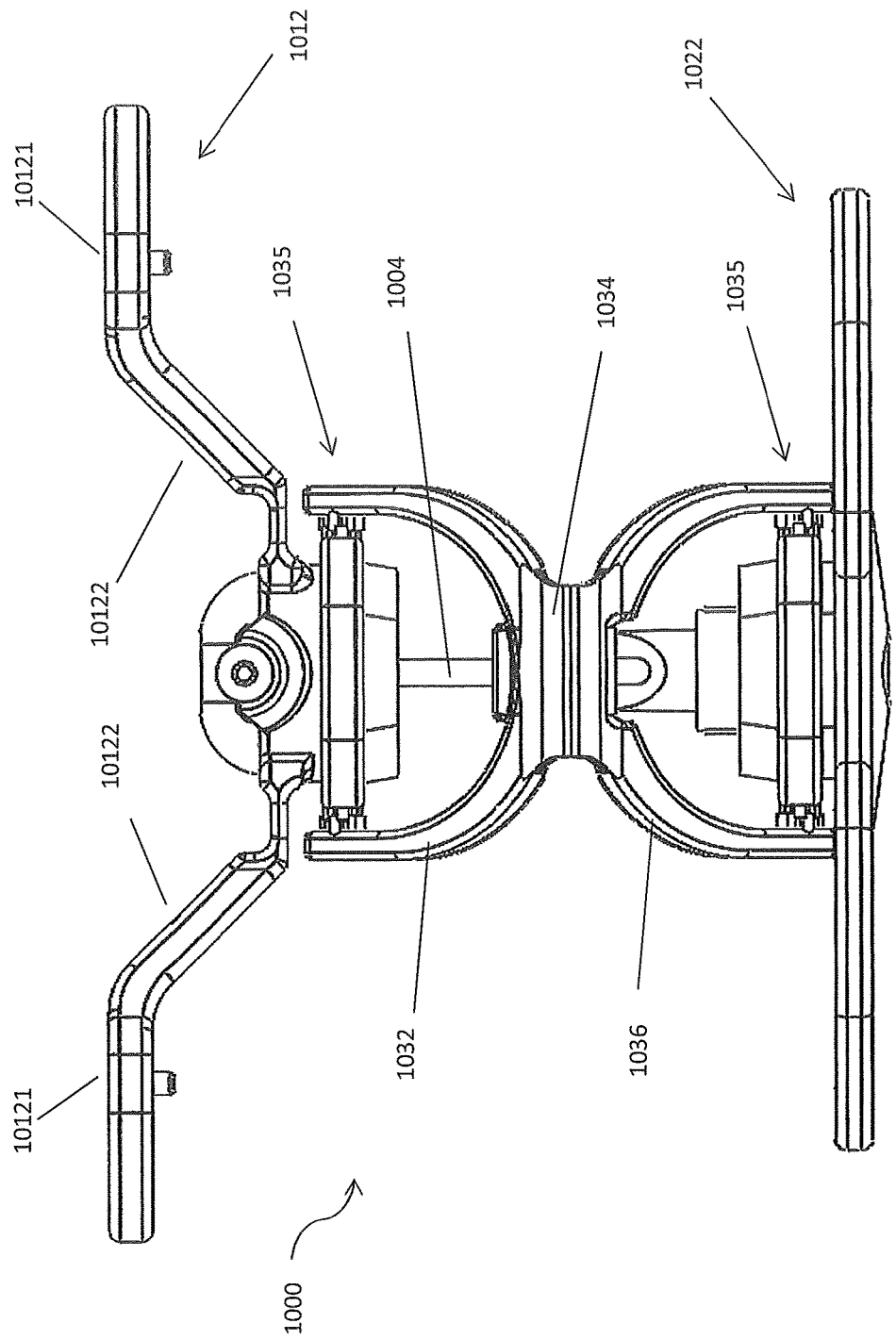
Figure 26A:
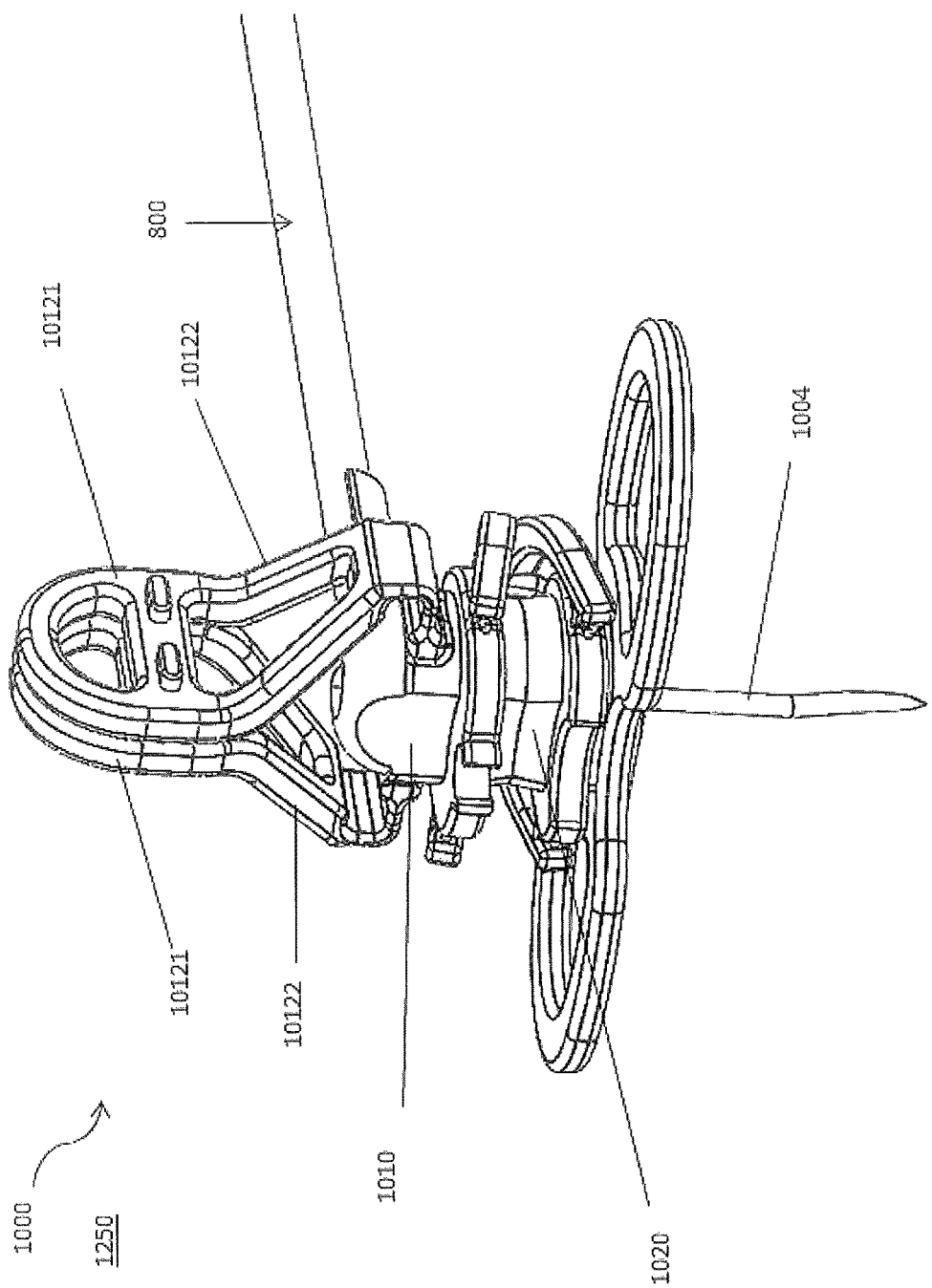
Figure 26B:
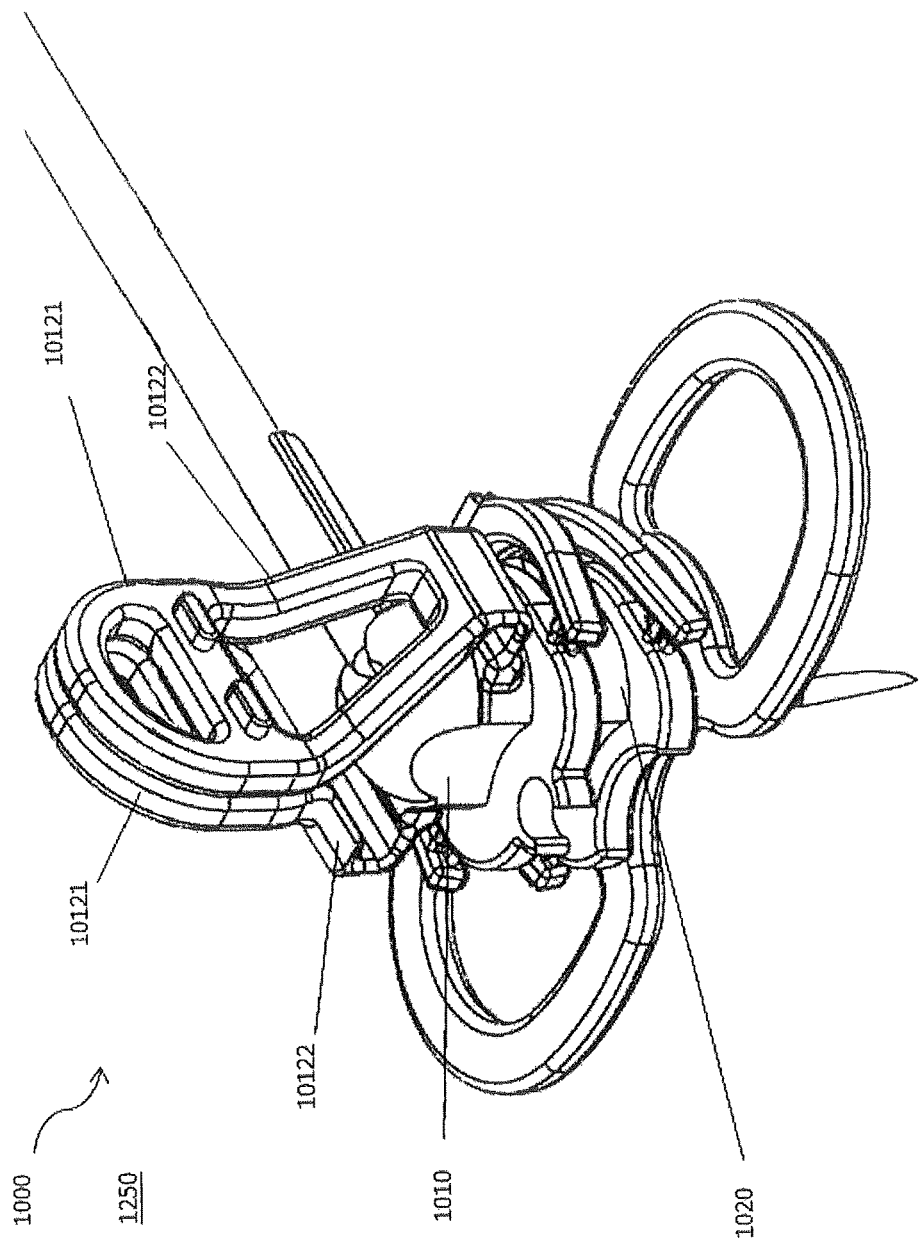
Figure 26C:
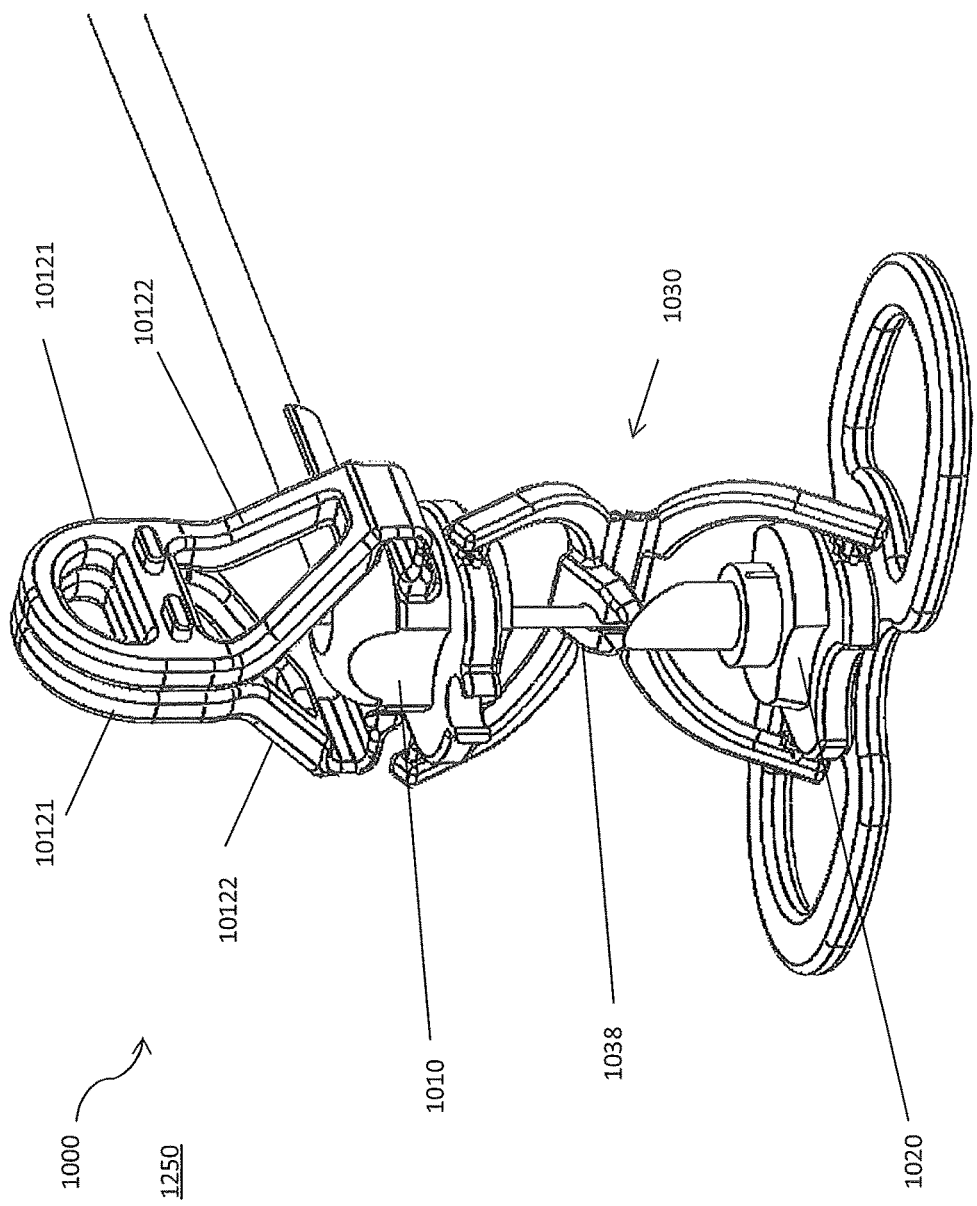

FIG. 17 illustrates a front view of an example Huber safety needle assembly 500 in an open configuration in accordance with a second embodiment. FIG. 18 illustrates a front cross-sectional view of an example Huber safety needle assembly 500 in an open configuration in accordance with a second embodiment. The lower portion 520 can be moved away from the upper portion 510 along the length of the needle 504. The movement of the lower portion 520 away from the upper portion 510 can allow the lower portion 520 to securely house the needle 504 and needle tip 506. In at least one embodiment, the needle 504 is fixed relative to the upper portion 510 allowing the lower portion to slide along the longitudinal axis of the needle 504.

As shown in FIG. 18, the upper and lower pivot points 533, 537 can be rotatable pin arrangements 535 configured to transition the needle assembly between configurations. In at least one embodiment, the middle portion 534 can function as a pin arrangement 535. The rotatable pin 535 can be configured to have a pivot point in substantially the same plane as the needle 504. The rotatable pin arrangement 535 can allow the pin to twist as the hinge mechanism 530 transitions the assembly 500 from one configuration 550, 575 to the other. The rotatable pin arrangement 535 can shorten the overall length of the hinge mechanism 530 compared to traditional mechanisms, thus creating a lower profile. In at least one embodiment, the rotatable pin arrangement 535 can include a plurality of rotatable pins. The rotatable pin arrangement 535 can allow the pin to twist as the hinge mechanism 530 is transitions the assembly 500 from one configuration 550, 575 to the other. The rotatable pins can be formed at the same time with the other parts of the body 508 using the same material. Each pin can be a simple cylindrical cross section or any cross section that would allow and facilitate the rotation around its axial, e.g., X shaped or with a polarity of ribs.

Alternatively, the rotatable pin arrangement 535 can have at least two pivot points 533, 537, each offset from the plane of the needle 504. For example, the upper pivot point 533 can be a distance $C_U$ from the plane of the needle 504, and the lower pivot can be a distance $C_L$ from the plane of the needle 504. In at least one embodiment, $C_U$ is less than $C_L$ such that the upper portion 532 of the hinge mechanism 530 is shorter than the lower portion 136 of the hinge mechanism 130. In other embodiments, $C_U$ is greater than $C_L$ such that the upper portion 532 of the hinge mechanism 530 is longer than the lower portion 536 of the hinge mechanism 530. The rotatable pin arrangement 535 can increase leverage while minimizing the distance necessary for the locking mechanism to engage the needle 504, thus making the Huber safety needle assembly 500 capable of locking passively. Passive locking allows the Huber safety needle assembly 500 to automatically engage the needle 504 as the Huber safety needle assembly 500 transitions from the closed configuration 550 to the open configuration 575. The passive locking allows securing the needle 504 to be a single step process during transition from the closed configuration 550 to the open configuration 575. In at least one embodiment, the rotatable pin arrangement 535 can include a plurality of rotatable pins. The rotatable pin arrangement 535 can allow the pin to twist as the hinge mechanism 530 is transitioned from one configuration to the other. As can be appreciated in FIGS. 17 and 18, the upper and lower portion 532, 536 of the hinge mechanism 530 can be coupled to each side of the body 508 by a rotatable pin arrangement 535. The upper portion 532 of the hinge mechanism 530 can be substantially U-shaped and configured to couple the upper portion 510 at each opposing end. Each opposing end can couple to the upper portion 510 using the rotatable pin arrangement 535 and be formed in substantially the same plane as the needle 504. The lower portion 536 of the hinge mechanism 530 can also be substantially U-shaped and be configured to couple the lower portion 520 at each opposing end. Each opposing end can couple to the lower portion 520 using the rotatable pin arrangement 535. The opposing ends and rotatable pin arrangement 535 can form a plane that substantially passes through the longitudinal axis of the needle 504.

The rotatable pin arrangement 535 can couple the upper portion 532 of the hinge mechanism 530 to the upper portion 510 and the lower portion 536 of the hinge mechanism 530 to the lower portion 520. In at least one embodiment, the rotatable pin 535 can have a substantially square cross-section with respect to a plane perpendicular to the cross-sectional view shown in FIG. 18. In alternative embodiments, the rotatable pin 535 can have a substantially circular, oval, triangular, or polygonal cross-section.

FIGS. 17-18 illustrate an example Huber safety needle assembly 500 in an open configuration 575 in accordance with a second embodiment. The Huber safety needle assembly 500 can be configured to transition from the closed configuration 550 to an open configuration 575 by applying a separating force along the longitudinal axis of the needle 504, or an axis or axes parallel thereto. The upper and lower gripping portions 512, 522 can be positioned on each side of the needle assembly 500 thereby keeping a transition force in axial alignment with the needle 504 when transitioning the needle assembly 500 between the closed 550 and open configurations 575. In at least one embodiment, the Huber safety needle assembly 500 is irreversibly transitionable from the closed configuration 550 to the open configuration 575. As the separation force is applied, the upper portion 510 and the lower portion 520 are displaced with respect to one another and the needle 504 passes through the lower portion 520, such that the needle tip 506 does not extend beyond the bottom surface of the lower portion 520. The assembly 500 can then be secured in the open configuration 575 as the needle 504 is secured by the attachment point 538. In at least one embodiment, the user can apply a separating force by securing the lower portion 520 in a fixed position and applying the force at the upper portion 510 along the plane of the needle 504 in a direction away from the lower portion 520. In alternative embodiments, depending on the arrangement of the needle assembly 500, the separation force can be applied at both the lower portion 520 and the upper portion 510 or only at the lower portion 510.

The separation force can operate the hinge mechanism 530, thereby separating the upper portion 510 and the lower portion 520 and securing the needle tip 506 within the lower portion 520. The attachment point 538 can secure the hinge mechanism 530 to the needle 504 further securing the needle assembly 500 in the open configuration 575. As can be appreciated in FIGS. 17-18, the upper portion 510 and the lower portion 520 are displaced along the length of the needle 504 and the needle 504 can be secured to the Huber safety needle assembly 500 at the attachment point 538. The upper portion 532 and lower portion 536 of the hinge mechanism 530 can be substantially perpendicular relative to their orientation in the closed configuration 550 (see FIG. 16A). In at least one embodiment, the hinge mechanism 530 can be substantially vertical in the open configuration 575 (see FIG. 16B). In at least one embodiment, the bottom surface of the lower portion 520 can include a protrusion configured to ensure the entire needle tip 506 is secured within the lower portion 520.

Referring to FIGS. 20-26, a third embodiment the Huber safety needle 1000 can include a body 1008 configured to secure a needle 1004. The needle 1004 can have a substantially hollow core configured to allow fluid flow therethrough and have a cross-sectional shape that is substantially circular, oval, triangular, rectangular, polygonal, or combinations thereof. In at least one embodiment, different gauge needles can be used for different applications and different delivery fluids. The needle 1004 can be made of any suitable material, such as stainless steel. The body 1008 can have an upper portion 1010 and a lower portion 1020.

The body 1008 can have any desired shape that provides a hollow portion configured to receive the needle 1004. The upper portion 1010 can be configured to detachably couple needle assembly 1000 to a catheter 800. For example, the body 1008 can be configured to matingly receive the catheter 800. In at least one embodiment, the catheter 800 is in fluid communication with the body 1008 and the needle 1004 providing a pathway for drugs, solutions, compounds, blood, or some other substance to be delivered through the needle 1004. The upper portion 1010 can further be configured to secure the needle 1004 within the body 1008. The lower portion 1020 can be configured to receive at least a portion of the needle 1004. In at least one embodiment, the lower portion 1020 can have an aperture formed therein to allow the needle 1004 to extend through the lower portion 1020. The lower portion 1020 can further include a skin plate 1024 on the bottom surface of the lower portion 1020.

The upper portion 1010 and the lower portion 1020 can each include upper and lower gripping portions 1012, 1022 respectively. The upper gripping portion 1012 and lower gripping portion 1022 can each have opposing sides. The upper gripping portion 1012 and the lower gripping portion 1022 can assist a user, or technician, with insertion of the Huber safety needle assembly 1000. The upper gripping 1012 can have a wing shape disposed on either side of the Huber safety needle assembly 1000, the wing like shape having to two surfaces 10121, 10122 angled relative to one another. The upper gripping portion 1012 can be pivotably attached to the upper portion 1010 allowing the opposing side upper gripping portion to be transition between a first configuration 1200 and a second configuration 1250. Alternatively, the upper gripping portion 1012 can be resiliently displaceable from the first configuration 1200 to the second configuration 1250. The first configuration 1200 can be each wing shape orientated substantially perpendicular relative to the longitudinal axis of the needle 1004, and the second configuration 1250 can be each wing shape orientated substantially parallel relative to the longitudinal axis of the needle 1004.

Each wing shape may comprise an angled structure such that when both wing shapes are in the second configuration 1250, a surface of each wing shape become substantially flush with each other. Grasping the upper gripping portion 1012 can cause the wing shapes to transition into the second configuration 1250, causing the substantially flush configuration described above. This may increase ergonomics and further ensure that the force applied to transition the assembly into the open configuration 1075 is substantially in line with the longitudinal axis of the needle 1004.

The body 1008 can further include a hinge mechanism 1030. The hinge mechanism 1030 can operably couple the upper portion 1010 and the lower portion 1020 and allow the body 1008 to transition from a closed configuration 1050 to an open configuration 1075. The closed configuration 1050 can allow at least a portion of the needle 1004, specifically the needle tip 1006, to be exposed from the lower portion 1020, thus allowing insertion of the needle 1004. In at least one embodiment, the closed configuration of the Huber safety needle assembly 1000 can be the same or substantially similar to the first and second embodiment Huber safety needle assemblies 100 and 500.

The hinge mechanism 1030 can include an upper portion 1032, a middle portion 1034, and a lower portion 1036. The upper portion 1032 of the hinge mechanism 1030 can be coupled to the upper portion 1010 at an upper pivot point 1033. The lower portion 1036 of the hinge mechanism 1030 can be coupled to the lower portion 1020 at a lower pivot point 1037. The middle portion 1034 can couple the upper portion 1032 and the lower portion 1036 and can be configured to function as a third pivot point. The upper and lower pivot points 1033, 1037 can be rotatable pin arrangements 1035 configured to transition the needle assembly between configurations 150, 175. In at least one embodiment, the middle portion 1034 can be a thinned area allowing the material to bend (or flex) as the Huber safety needle assembly 1000 transitions from a closed configuration 1050 to an open configuration 1075.

The hinge mechanism 1030 can further include at least one attachment point 1038 configured to secure the hinge mechanism 1030 to the needle 1004 when in the open configuration 1075. The attachment point 1038 can be any suitable means for securing the hinge mechanism 1030 to the needle 1004. In at least one embodiment, the at least one attachment point 1038 can be a snap-fit configuration. In an alternative embodiment, the at least one attachment point 1038 can be substantially L-shaped allowing the attachment point 1038 to push past the needle 1004 when transitioning from the closed configuration 1050 to the open configuration 1075, thereby securing the needle 1004 in the void formed in the substantially L-shaped attachment point 1038.

The Huber safety needle assembly 1000 can include two attachment points 1038, one disposed on each of the upper portion 1032 and the lower portion 1036. Depending on the configuration, the Huber safety needle assembly 1000 can have a single attachment configuration, more than two attachment points, or any combination thereof.

In a second example embodiment of an upper gripping portion 1012 of the Huber safety needle assembly 1000, the assembly 1000 can have an upper gripping portion 1012 disposed on either side of the upper portion 1010, approximately 180 degrees apart. Each upper gripping portion 1012 can have a wing-like shape formed by two surfaces 10121, 10122. The two surfaces 10121, 10122 can be approximately equal and coupled together at a midpoint. The upper gripping portion can have a first configuration 1200 and a second configuration 1250.

In the first configuration 1200, the upper gripping portion 1012 can extend laterally away from the body 1008 of the Huber safety needle assembly 1000. In the second configuration 1250, the upper gripping portion 1012 can pivot such as to extend vertically along the plane of the needle 1004. The upper gripping portion 1012 can pivot about the coupling between the upper gripping portion 1012 and the body 1008.

A first surface 10121 can be angled above a plane substantially perpendicular to the needle 1004, and a second surface 10122 can be angled approximately 45 degrees relative to a plane parallel to the needle 1004. The first surface 10121 can be angled between 0 and 45 degrees above the substantially perpendicular plane to the needle 1004 and the second surface can be angled between 20 and 70 degrees relative to the substantially parallel plane to the needle 10004. In at least one embodiment, the first surface 10121 is angle approximately 135 degrees relative to the second surface 10122. In other embodiments the first surface 10121 is angle approximately 90 degrees relative to the second surface 10122.

The upper gripping portion 1012 can be pivoted about the coupling to the body 1008 to a second position 1250. The first surface 10121 of each opposing upper gripping portion 1012 can be substantially flush against one other to allow a technician to apply a force directly in line with needle, thereby transition the Huber safety needle assembly 1000 from a closed configuration 1050 to an open configuration 1075.

Although illustrated with respect to the Huber safety needle assembly 1000, the upper gripping portion 1012 can be implemented with any of the embodiments of Huber safety needle assembly disclosed herein without limitation.

It is believed the exemplary embodiment and its advantages will be understood from the foregoing description, and it will be apparent that various changes may be made thereto without departing from the spirit and scope of the disclosure or sacrificing all of its advantages, the examples hereinbefore described merely being preferred or exemplary embodiments of the disclosure.

What is claimed is:

1. A Huber safety needle assembly comprising:
    a body having an upper portion, a lower portion, and a hinge mechanism;
    a needle configured to be received in the body, wherein the needle extends in a first direction from a rear of the assembly to a front of the assembly, makes a 90-degree bend, and extends in a second direction toward a bottom of the assembly which then leads to a needle tip; and
    an upper gripping portion coupled to the upper portion and a lower gripping portion coupled to the lower portion;
    wherein the hinge mechanism is configured to operably transition the body between a closed configuration and an open configuration by displacing the upper portion and the lower portion from each other relative to a longitudinal axis extending through the needle along the second direction, the closed configuration allowing at least a portion of the needle including the needle tip to extend below a bottom surface of the lower portion of the body, and the open configuration allowing the needle tip to be securely received within the lower portion such that it does not extend below the bottom surface of the lower portion;
    wherein the hinge mechanism includes an upper portion, a middle portion, and a lower portion and has a plurality of pivot points, wherein the upper portion of the hinge mechanism couples the hinge mechanism to the upper portion of the body and the lower portion of the hinge mechanism couples the hinge mechanism to the lower portion of the body,
    wherein the upper portion of the hinge mechanism is substantially U-shaped and the lower portion of the hinge mechanism is substantially U-shaped such that each of the upper portion of the hinge mechanism and the lower portion of the hinge mechanism can accommodate the needle, and
    wherein the hinge mechanism comprises:
        an upper pivot point comprising an upper rotatable pin arrangement having a plurality of rotatable pins and configured for coupling the upper portion of the hinge mechanism to each side of the upper portion of the body,
        a middle pivot point being a thinned area of material configured to allow the material to bend at the middle portion, and
        a lower pivot point comprising a lower rotatable pin arrangement having a plurality of rotatable pins and configured for coupling the lower portion of the hinge mechanism to each side of the lower portion of the body.

2. The Huber safety needle assembly of claim 1, further comprising at least one attachment point extending from the hinge mechanism, the at least one attachment point configured to secure the hinge mechanism to the needle.

3. The Huber safety needle assembly of claim 2, wherein the needle assembly non-retractably transitions from the closed configuration to the open configuration.

4. The Huber safety needle assembly of claim 2, wherein the at least one attachment point is a snap fit.

5. The Huber safety needle assembly of claim 2, wherein the at least one attachment point is a protrusion extending from the hinge mechanism and is configured to allow passing the needle in one direction thereby securing the needle after transitioning from the closed configuration to the open configuration.

6. The Huber safety needle assembly of claim 1, wherein each of the upper pivot point and the lower pivot point is positioned at the front of the assembly, and the middle pivot point is positioned at the rear of the assembly.

7. The Huber safety needle assembly of claim 1, wherein each pin of the plurality of rotatable pins of the upper pivot point and each pin of the-plurality of rotatable pins of the lower pivot point has a square, circular, oval, triangular, polygonal, cylindrical or X shaped cross section, or has a plurality of ribs.

8. The Huber safety needle assembly of claim 1, wherein the upper gripping portion comprises opposing sides, and each of the opposing sides is pivotably attached to the upper portion allowing the opposing sides of the upper gripping portion to be transitioned between a first configuration and a second configuration.

9. The Huber safety needle assembly of claim 1, wherein the upper and lower gripping portions are positioned on each side of the needle assembly keeping a transition force in axial alignment with the needle when transitioning the needle assembly between the closed and open configurations.

10. The Huber safety needle assembly of claim 1, wherein the body is configured to matingly receive a catheter.

11. The Huber safety needle assembly of claim 10, wherein the catheter is in fluid communication with the body and the needle.

12. The Huber safety needle assembly of claim 1, wherein the lower portion has an aperture formed therein configured to allow the needle to extend through the lower portion.

13. The Huber safety needle assembly of claim 1, further comprising a skin plate on the lower portion.

* * * * *